(12) United States Patent
Lee

(10) Patent No.: US 9,887,363 B2
(45) Date of Patent: *Feb. 6, 2018

(54) COMPOUND AND ORGANIC LIGHT EMITTING DEVICE COMPRISING THE SAME

(71) Applicant: Samsung Display Co., Ltd., Yongin, Gyeonggi-Do (KR)

(72) Inventor: Jung-Sub Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 834 days.

This patent is subject to a terminal disclaimer.

(21) Appl. No.: 14/139,773

(22) Filed: Dec. 23, 2013

(65) Prior Publication Data

US 2014/0239275 A1 Aug. 28, 2014

(30) Foreign Application Priority Data

Feb. 28, 2013 (KR) .................. 10-2013-0022443

(51) Int. Cl.
| | | |
|---|---|---|
| B32B 9/00 | (2006.01) | |
| B32B 19/00 | (2006.01) | |
| H01L 51/00 | (2006.01) | |
| C07D 487/04 | (2006.01) | |
| C07D 495/04 | (2006.01) | |
| H01L 51/50 | (2006.01) | |

(52) U.S. Cl.
CPC ........ *H01L 51/0058* (2013.01); *C07D 487/04* (2013.01); *C07D 495/04* (2013.01); *H01L 51/0071* (2013.01); *H01L 51/0072* (2013.01); *H01L 51/5012* (2013.01)

(58) Field of Classification Search
CPC . H01L 51/52; H01L 51/0051; H01L 51/0062; H01L 51/0052; H01L 51/005; H01L 51/0071; H01L 51/0072
USPC .......................................... 428/690
See application file for complete search history.

(56) References Cited

U.S. PATENT DOCUMENTS 9,082,988 B2 * 7/2015 Lee .................. H01L 51/5016
2011/0127513 A1 6/2011 Lee et al.

FOREIGN PATENT DOCUMENTS

KR 10-2011-0042127 A 4/2011
KR 10-2011-0066766 A 6/2011
(Continued)

*Primary Examiner* — Austin Murata
(74) *Attorney, Agent, or Firm* — Lewis Roca Rothgerber Christie LLP

(57) ABSTRACT

An organic light emitting compound includes the compound of Formula 1 below:

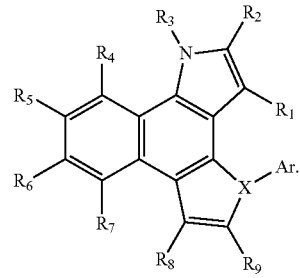

Formula 1

Descriptions of substituents of Formula 1 are as described in the detailed description.

20 Claims, 1 Drawing Sheet

(56) References Cited

FOREIGN PATENT DOCUMENTS

| | | |
|---|---|---|
| KR | 10-2011-0092262 A | 8/2011 |
| KR | 10-2012-0020816 A | 3/2012 |

\* cited by examiner

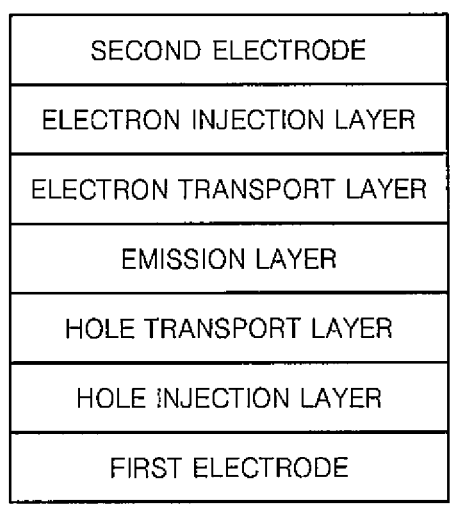

COMPOUND AND ORGANIC LIGHT EMITTING DEVICE COMPRISING THE SAME

CROSS-REFERENCE TO RELATED APPLICATION

This application claims priority to and the benefit of Korean Patent Application No. 10-2013-0022443, filed on Feb. 28, 2013, in the Korean Intellectual Property Office, the disclosure of which is incorporated herein in its entirety by reference.

BACKGROUND

1. Field

The following description relates to heterocyclic compounds and organic light emitting devices comprising the same.

2. Description of the Related Art

Organic light-emitting diodes (OLEDs), which are self-emitting diodes, have advantages such as wide viewing angles, excellent contrast, quick response, high brightness, excellent driving voltage characteristics, or can provide multicolored images.

A typical OLED has a structure including a substrate, and an anode, a hole transport layer, an emission layer, an electron transport layer, and a cathode which are sequentially stacked on the substrate. The hole transport layer, the emission layer, and the electron transport layer are organic thin films formed of organic compounds.

An operating principle of an OLED having the above-described structure is as follows.

When a voltage is applied between the anode and the cathode, holes injected from the anode move to the emission layer via the hole transport layer, and electrons injected from the cathode move to the emission layer via the electron transport layer. The holes and electrons recombine in the emission layer to generate excitons. When the excitons drop from an excited state to a ground state, light is emitted.

The most important factor determining the emission efficiency in the OLED is the emission materials. Fluorescent materials have been used as the emission materials until now; however, a development of phosphorescent materials is theoretically one of the best ways to improve the emission efficiency up to four times. Until now, iridium (III) complex-based materials have been used as phosphorescent emission materials, and with respect to each red, green and blue color (RGB), $(acac)Ir(btp)_2$, $Ir(ppy)_2$, Firpic, or the like are used.

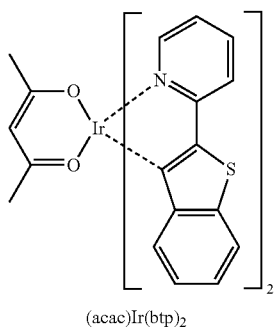

$(acac)Ir(btp)_2$

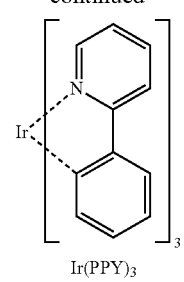

$Ir(PPY)_3$

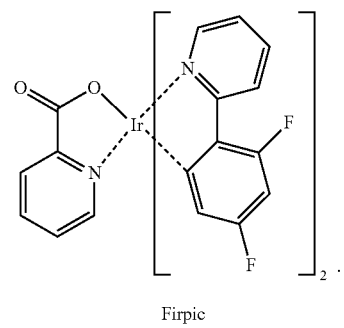

Firpic

In regards to materials for a phosphorescent illuminant, CBP is the most widely used until now. Also, high efficiency OLEDs including hole blocking layers such as BCP and BAlq are used, and high performance OLEDs using BAlq derivatives as hosts are used by Pioneer Co., or the like in Japan.

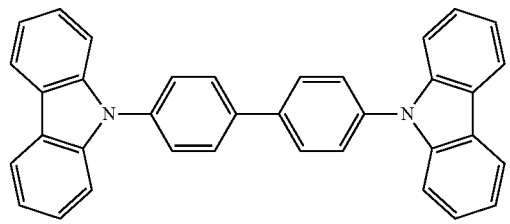

CBP

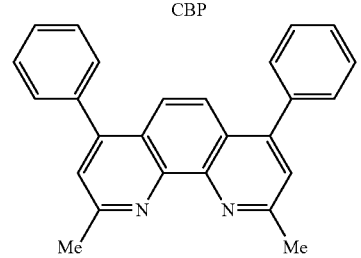

BCP

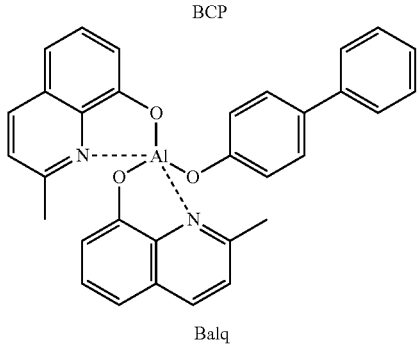

Balq

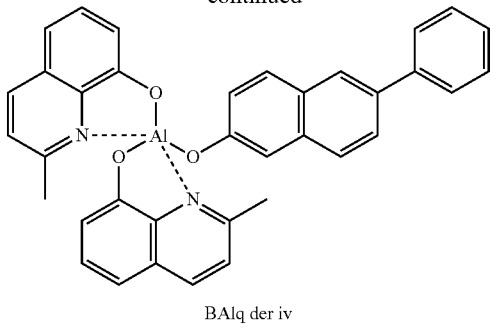

BAlq der iv

Although existing materials have good emission characteristics, the existing materials have a low glass transition temperature and a very poor thermal stability, causing problems such as changes in materials when the existing materials are subject to a high temperature deposition process under a vacuum condition. Since electric power efficiency of OLED=(π/voltage)×current efficiency, the electric power efficiency is inversely proportional to the voltage, and accordingly, the electric power efficiency must be great in order for an electric power consumption of the OLED to be low. An OLED using the phosphorescent materials actually has a substantially greater current efficiency (cd/A) compared to that of an OLED using fluorescent materials, but when materials, such as BAlq, CBP, or the like is used as the host for the phosphorescent materials, a driving voltage of the OLED using the phosphorescent materials is greater than that of the OLED using the fluorescent materials, and thus, there is no substantial enhancement in regards to the electric power efficiency (lm/w). Also, a lifespan of the OLED using the phosphorescent materials is not satisfactory. Thus, a host material having a better performance is required.

SUMMARY

Aspects of embodiments of the present invention are directed toward organic light emitting compounds having improved emission efficiency and device lifespan than existing host materials, desired color coordinates and excellent skeletal structures, and an organic light emitting device having high efficiency and long lifespan including the organic light emitting compounds.

Additional aspects will be set forth in part in the description which follows and, in part, will be apparent from the description, or may be learned by practice of the presented embodiments.

According to one or more embodiments of the present invention, there is provided a heterocyclic compound represented by Formula 1 below:

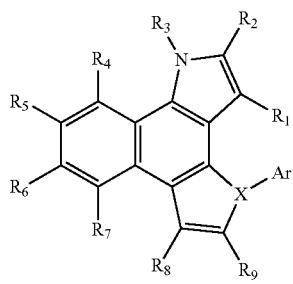

Formula 1 wherein, $R_1$ to $R_9$ may be, each independently, a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_6$-$C_{60}$ aryl group, a substituted or unsubstituted $C_3$-$C_{60}$ heteroaryl group, a $C_6$-$C_{60}$ arylsilyl group, or a substituted or unsubstituted $C_6$-$C_{60}$ condensed polycyclic group;

Ar is a non-bonding electron pair, a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group; and X is N or S.

According to one or more embodiments of the present invention, there is provided an organic light-emitting device including a first electrode; a second electrode; and an organic layer between the first electrode and the second electrode and including an emission layer, and the organic layer includes a heterocyclic compound.

According to one or more embodiments of the present invention, there is provided a flat display device including an organic light emitting device, wherein a first electrode of the organic light emitting device is electrically connected to a source electrode or a drain electrode of a thin film transistor.

BRIEF DESCRIPTION OF THE DRAWINGS

These and/or other embodiments will become apparent and more readily appreciated from the following description of the embodiments, taken in conjunction with the accompanying drawing of which:

The drawing schematically illustrates a structure of an organic light emitting device according to an embodiment of the present invention.

DETAILED DESCRIPTION

Reference will now be made in detail to embodiments, examples of which are illustrated in the accompanying drawing, wherein like reference numerals refer to the like elements throughout. In this regard, the present embodiments may have different forms and should not be construed as being limited to the descriptions set forth herein. Accordingly, the embodiments are merely described below, by referring to the drawing, to explain embodiments of the present description.

A compound according to an embodiment of the present invention is represented by Formula 1 below:

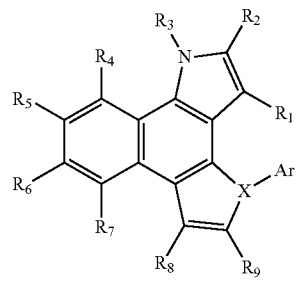

Formula 1 wherein in the Formula above, $R_1$ to $R_9$ may be, each independently, a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_6$-$C_{60}$ aryl group, a substituted or unsubstituted $C_3$-$C_{60}$ heteroaryl group, a $C_6$-$C_{60}$ arylsilyl group, or a substituted or unsubstituted $C_6$-$C_{60}$ condensed polycyclic group;

Ar is a non-bonding electron pair, a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group; and X is N or S.

The compound of Formula 1 according to the present invention has a function of a green phosphorescent material of an organic light emitting device (OLED). Also, the compound of Formula 1 has a high glass transition temperature (Tg) or a high melting point by integrating a heterocyclic group. Accordingly, thermal resistance increases with respect to Joule's heat arising between organic layers or between the organic layer and a metal electrode during an electroluminescence, and tolerance increases under a high temperature environment. The OLED manufactured by using heterocyclic compounds according to embodiments of the present invention has high durability during maintenance and driving.

Substituents of compounds of Formula 1 will be described in greater detail.

According to an embodiment of the present invention, $R_3$ of Formula 1 is any one of the structures below:

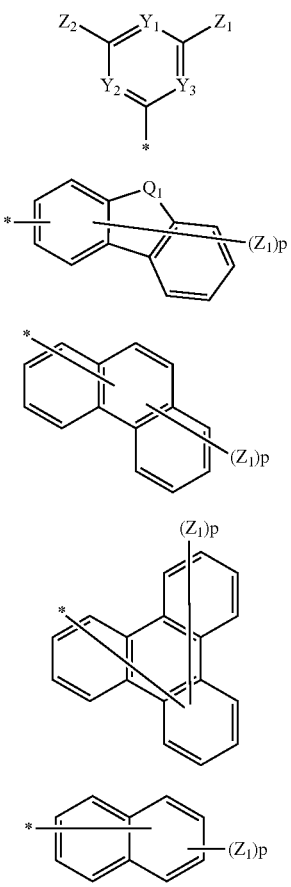

Wherein in the Formulae above,
$Y_1$, $Y_2$, and $Y_3$ are, each independently, CH or N;
$Q_1$ is a connecting group represented by —$CR_{50}R_{51}$— or —S—;

$Z_1$, $Z_2$, $R_{50}$ and $R_{51}$ are, each independently, a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group, a $C_3$-$C_{20}$ heteroaryl group, a halogen group, a cyano group, a nitro group, a hydroxyl group, or a carboxy group;

p is an integer of 1 to 11; and * represents a binding site.

According to another embodiment of the present invention, $R_6$ of Formula 1 is any one of the structures below:

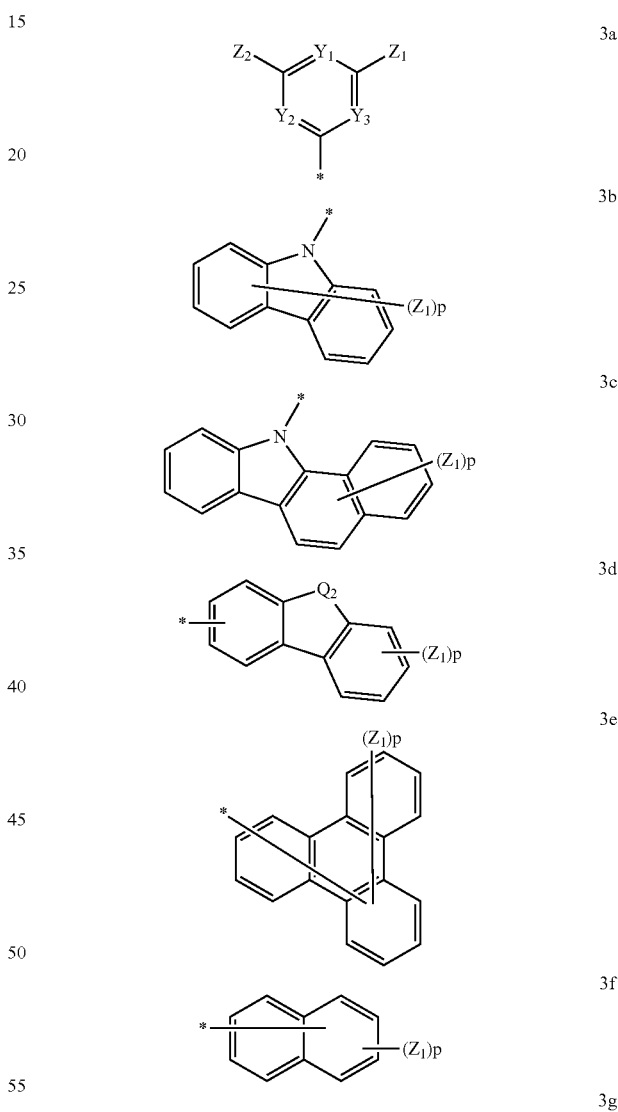

Wherein in the Formulae above, $Y_1$, $Y_2$, and $Y_3$ are, each independently, CH or N;

$Q_2$ is a connecting group represented by —O— or —S—;
$Z_1$, $Z_2$, $R_{10}$, $R_{11}$ and $R_{12}$ are, each independently, a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group, a $C_3$-$C_{20}$ heteroaryl group, a halogen group, a cyano group, a nitro group, a hydroxyl group, or a carboxy group;

p is an integer of 1 to 11; and * represents a binding site.

According to another embodiment of the present invention, $R_9$ of Formula 1 above is a hydrogen atom, a deuterium atom, or

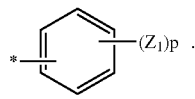

$Z_1$ is a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group, a $C_3$-$C_{20}$ heteroaryl group, a halogen group, a cyano group, a nitro group, a hydroxyl group, or a carboxy group; p is an integer of 1 to 5; and * represents a binding site.

According to another embodiment of the present invention, Ar of Formula 1 above is a non-bonding electron pair, or any one of the structures below:

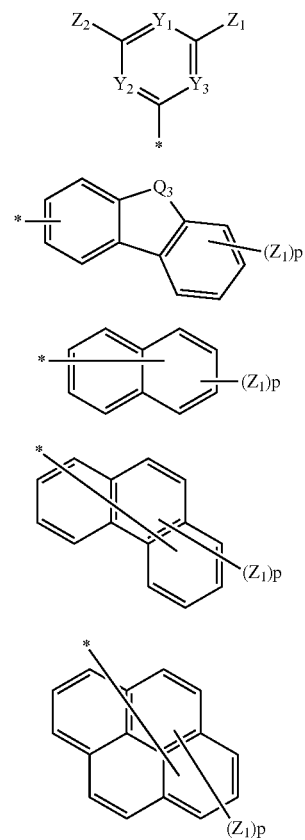

wherein, $Y_1$, $Y_2$, and $Y_3$ are, each independently, CH or N; $Q_3$ is a connecting group represented by —$CR_{50}R_{51}$—, —$NR_{52}$—, or —S—;

$Z_1$, $Z_2$, $R_{50}$, $R_{51}$ and $R_{52}$ are, each independently, a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group, a $C_3$-$C_{20}$ heteroaryl group, a halogen group, a cyano group, a nitro group, a hydroxyl group, or a carboxy group;

p is an integer of 1 to 9; and * represents a binding site.

According to another embodiment of the present invention, $R_1$, $R_2$, $R_4$, $R_5$, $R_7$, and $R_8$ of Formula 1 above are, each independently, represented by a hydrogen atom or a deuterium atom.

Hereinafter, representative substituents used in the present specification are as follows (carbon numbers limiting the substituents are non-limiting and do not limit the characteristics of the substituents, and substituents that are not described in the present specification are included if found in general definitions of the substituents).

The unsubstituted $C_1$-$C_{60}$ alkyl group may be linear or branched, and non-limiting examples of the unsubstituted $C_1$-$C_{60}$ alkyl group include methyl, ethyl, propyl, isobutyl, sec-butyl, pentyl, iso-amyl, hexyl, heptyl, octyl, nonanyl, dodecyl, or the like, and at least one hydrogen atom of the alkyl group may be substituted with a deuterium atom, a halogen atom, a hydroxy group, a nitro group, a cyano group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

As used herein, the unsubstituted $C_2$-$C_{60}$ alkenyl group is a hydrocarbon chain having a carbon-carbon double bond in the middle or at a terminal of the unsubstituted $C_2$-$C_{60}$ alkyl group. Examples of the alkenyl group are an ethenyl group, a propenyl group, a butenyl group, or the like. At least one hydrogen atom in the unsubstituted $C_2$-$C_{60}$ alkenyl group may be substituted with those substituents described above in conjunction with the substituted alkyl group.

The unsubstituted $C_2$-$C_{60}$ alkynyl group is a $C_2$-$C_{60}$ alkyl group having at least one carbon-carbon triple bond in the center or at a terminal thereof. Examples of the unsubstituted $C_2$-$C_{60}$ alkynyl group are acetylene, propylene, phenylacetylene, naphthylacetylene, isopropyl acetylene, t-butyl acetylene, diphenyl acetylene, or the like. At least one hydrogen atom in the alkynyl group may be substituted with those substituents described above in conjunction with the substituted alkyl group.

The unsubstituted $C_3$-$C_{60}$ cycloalkyl group is a $C_3$-$C_{60}$ cyclic alkyl group, and at least one hydrogen atom of the cycloalkyl group may be substituted with those substituents described above in conjunction with the $C_1$-$C_{60}$ alkyl group.

The unsubstituted $C_1$-$C_{60}$ alkoxy group may be a group represented by —OA, wherein A is an unsubstituted $C_1$-$C_{60}$ alkyl group described above. Non-limiting examples of the unsubstituted $C_1$-$C_{60}$ alkoxy group are a methoxy group, an ethoxy group, an isopropyloxy group, a butoxy group, or a pentoxy group. At least one hydrogen atom of the alkoxy group may be substituted with those substituents described above in conjunction with the substituted $C_1$-$C_{60}$ alkyl group.

The unsubstituted $C_6$-$C_{60}$ aryl group is a monovalent group having a carbocyclic aromatic system including at least one aromatic ring, and when the aryl group has at least two rings, they may be fused or connected to each other via a single bond. The term "aryl" as used herein includes an aromatic system such as phenyl, naphthyl or anthracenyl. At least one hydrogen atom in the aryl group may be substituted with those substituents described above in conjunction with the $C_1$-$C_{60}$ alkyl group.

The $C_6$-$C_{60}$ arylsilyl group refers to those with one, two, or three of the $C_6$-$C_{60}$ aryl groups substituted with Si.

Examples of a substituted or unsubstituted $C_6$-$C_{60}$ aryl group include a phenyl group, a $C_1$-$C_{10}$ alkyl phenyl group (for example, an ethyl phenyl group), a halophenyl group (for example, an o-, m- and p-fluorophenyl group and a dichlorophenyl group), a cyanophenyl group, a dicyanophenyl group, trifluoromethoxy phenyl group, biphenyl group, halobiphenyl group, cyanobiphenyl group, a $C_1$-$C_{10}$ alkylbiphenyl group, a $C_1$-$C_{10}$ alkoxybiphenyl group, an o-, m-, and p-tolyl group, an o-, m- and p-cumenyl group, a mesityl group, a phenoxyphenyl group, an (α,α-dimethyl benzene) phenyl group, an (N,N'-dimethyl) amino phenyl group, an (N,N'-diphenyl) amino phenyl group, a pentalenyl group, an indenyl group, a naphthyl group, a halonaphthyl group (for example, a fluoronaphthyl group), a $C_1$-$C_{10}$ alkyl naphthyl group (for example, a methyl naphthyl group), a $C_1$-$C_{10}$ alkoxy naphthyl group (for example, a methoxy naphthyl group), a cyanonaphthyl group, an anthracenyl group, an azulenyl group, a heptalenyl group, an acenaphthylenyl group, a phenalenyl group, a fluorenyl group, an anthraquinolyl group, a methyl anthryl group, a phenanthryl group, a triphenylene group, a pyrenyl group, a chrysenyl group, an ethyl-chrysenyl group, a picenyl group, a pherylenyl group, a chloropherylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, an ovalenyl group, and the like.

The unsubstituted $C_3$-$C_{60}$ heteroaryl group includes one, two, or three heteroatoms selected from N, O, P, or S, and when the unsubstituted $C_3$-$C_{60}$ heteroaryl group has at least two rings, they may be fused or connected to each other via a single bond. Examples of the unsubstituted $C_4$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolyl group, an isoquinolyl group, a dibenzothiophene group, and the like. Also, at least one hydrogen atom of the heteroaryl group may be substituted with those substituents described in conjunction with the $C_1$-$C_{60}$ alkyl group.

The substituted or unsubstituted $C_6$-$C_{60}$ aryloxy group is represented by —$OA_1$ (where $A_1$ is a substituted or unsubstituted $C_6$-$C_{60}$ aryl group described above). Examples of the aryloxy group include a phenoxy group, and the like. At least one hydrogen atom in the aryloxy group may be substituted with those substituents described in conjunction with the $C_1$-$C_{60}$ alkyl group.

The substituted or unsubstituted $C_6$-$C_{60}$ arylthio group is represented by —$SA_1$ (where $A_1$ is a substituted or unsubstituted $C_6$-$C_{60}$ aryl group described above). Examples of the arylthio group include a benzenethio group, a naphthylthio group, and the like. At least one hydrogen atom in the arylthio group may be substituted with those substituents described in conjunction with the $C_1$-$C_{60}$ alkyl group.

The expression "the unsubstituted $C_6$-$C_{60}$ condensed polycyclic group" as used herein refers to a substituent including two or more rings, wherein at least one aromatic ring and at least one non-aromatic ring are fused, or a substituent having an unsaturated group that is incapable of having a conjugated structure. The condensed polycyclic group is distinguished from the aryl group, or the heteroaryl group in that the condensed polycyclic group does not have aromaticity.

Examples of the compounds represented by Formula 1 are as follows, but are not limited thereto:

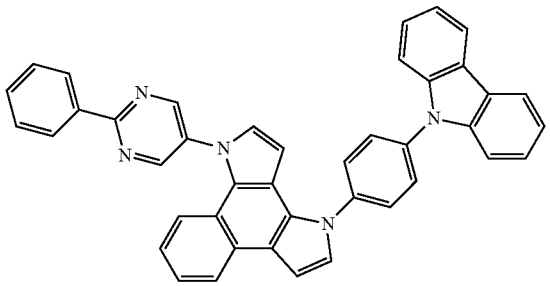

1

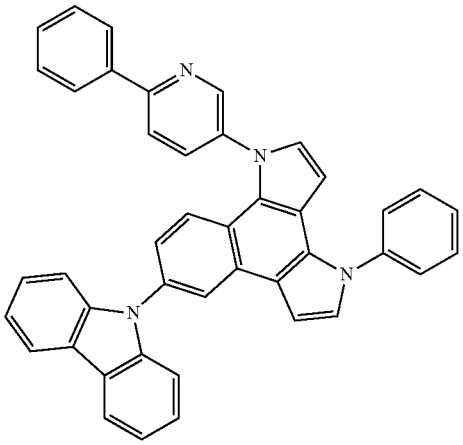

2

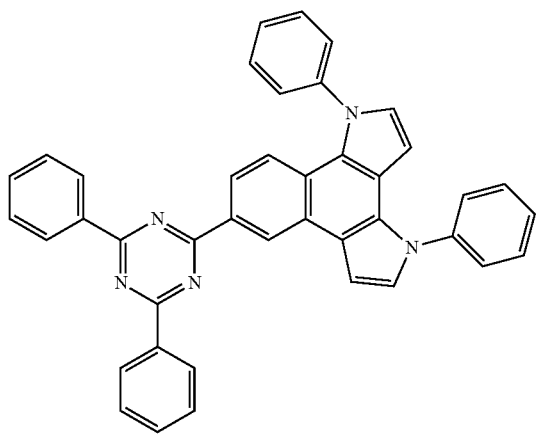

3

4
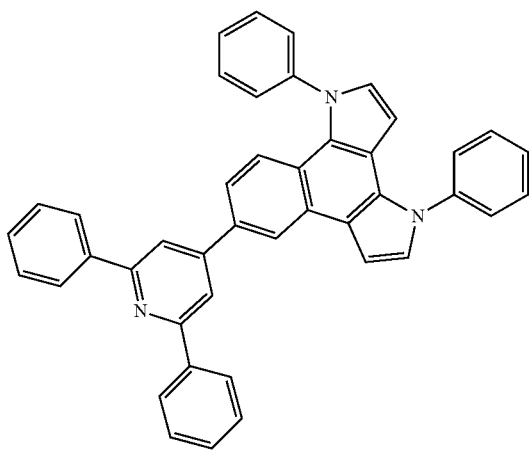
5
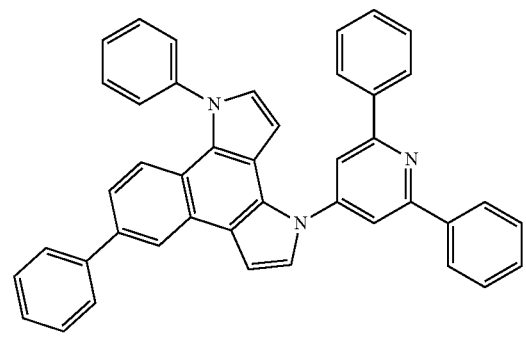
6
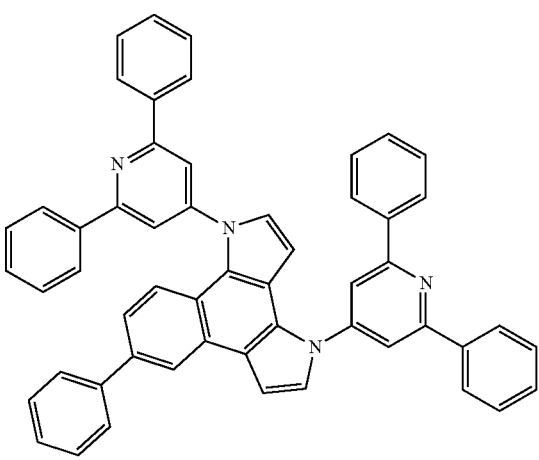
7
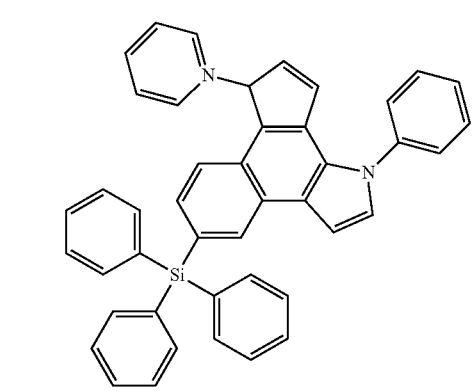
8
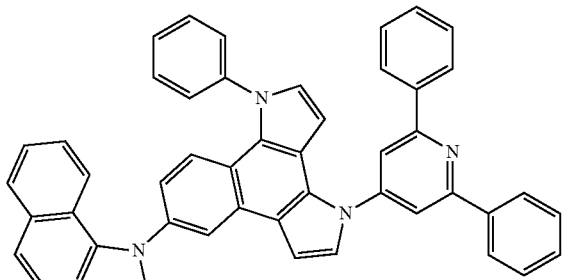
9
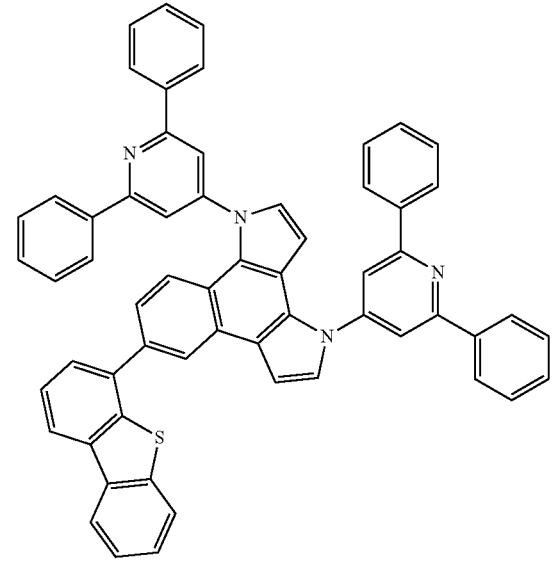
10
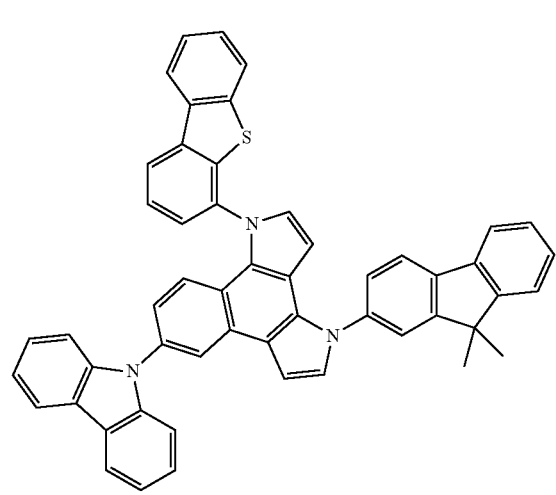

11
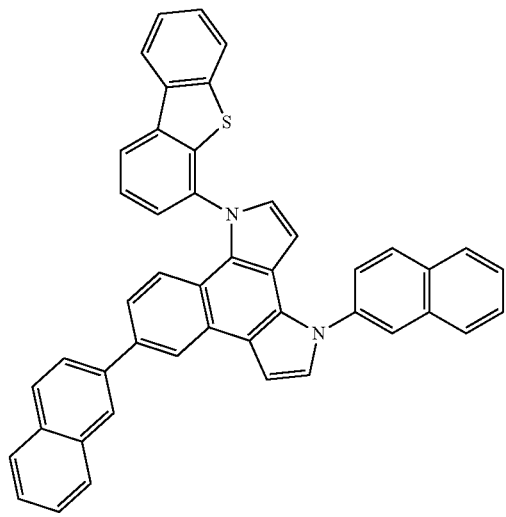
12
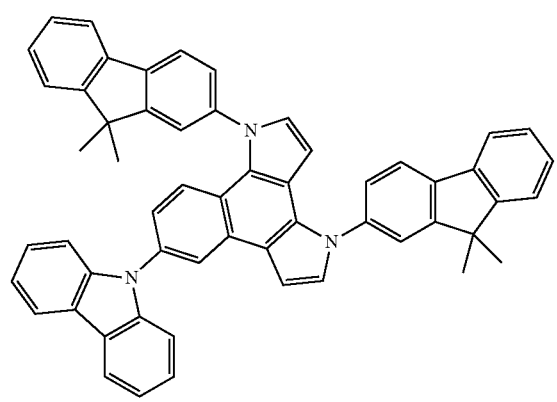
13
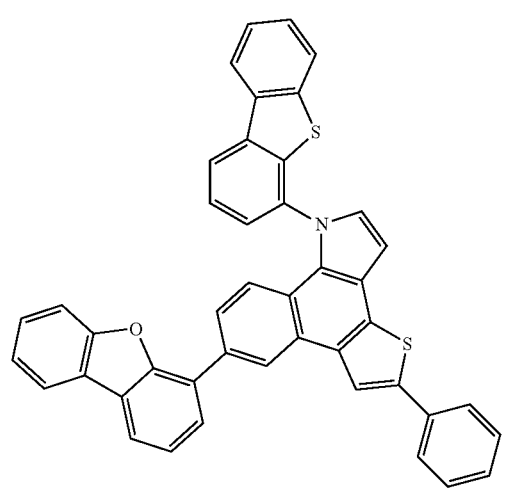
14
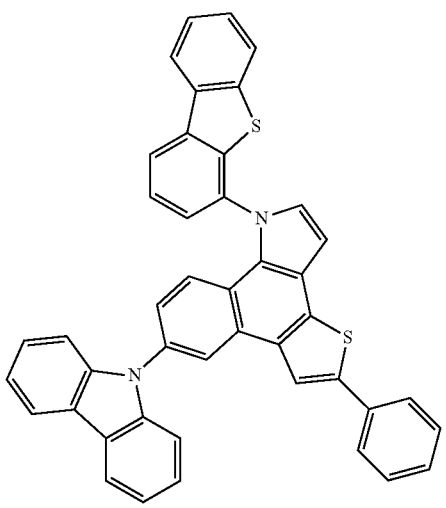
15
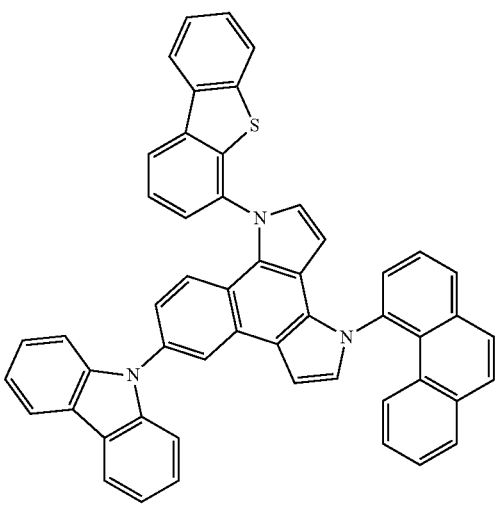
16
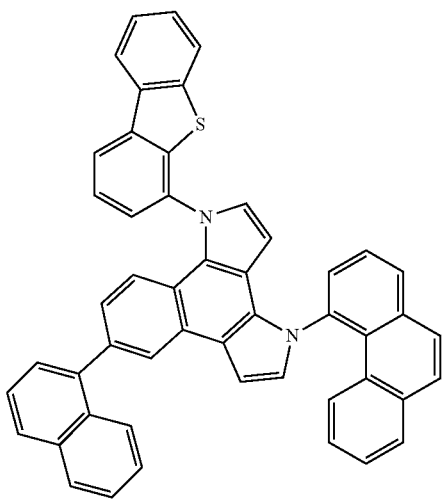

17

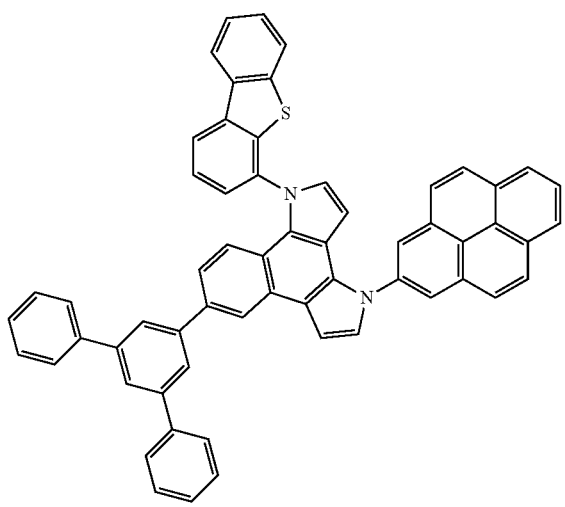

18

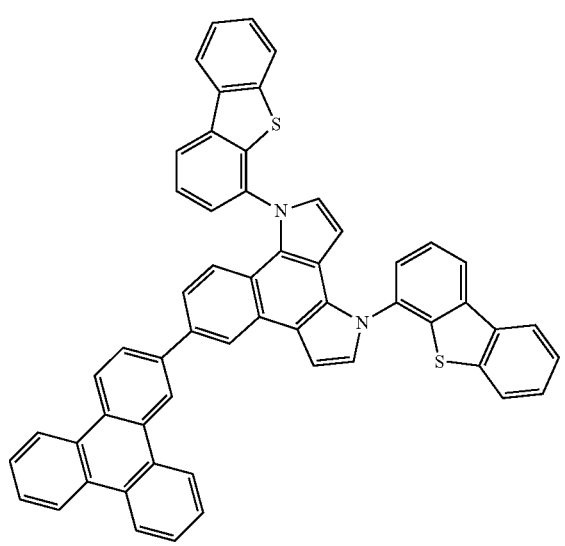

19

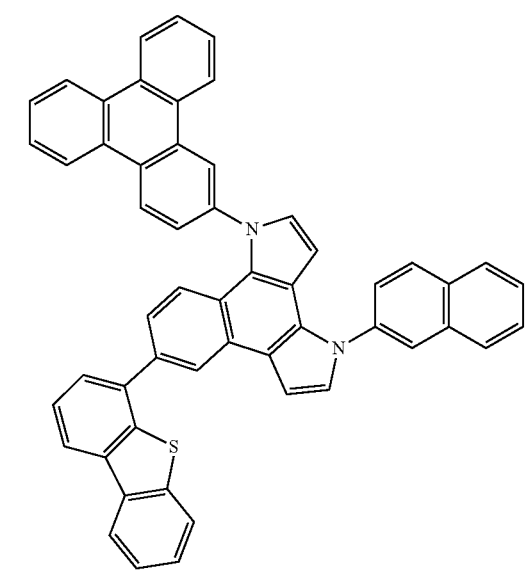

20

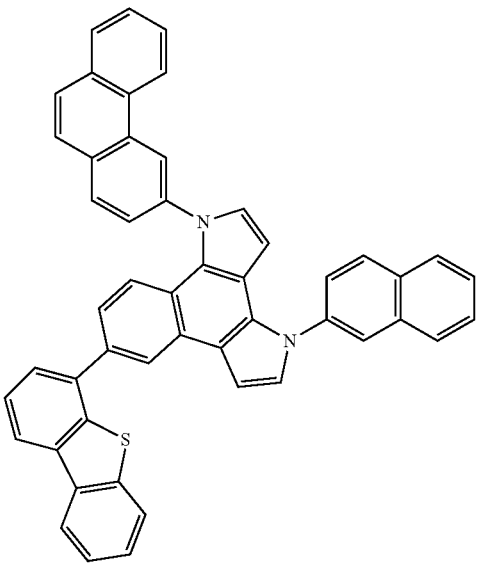

21

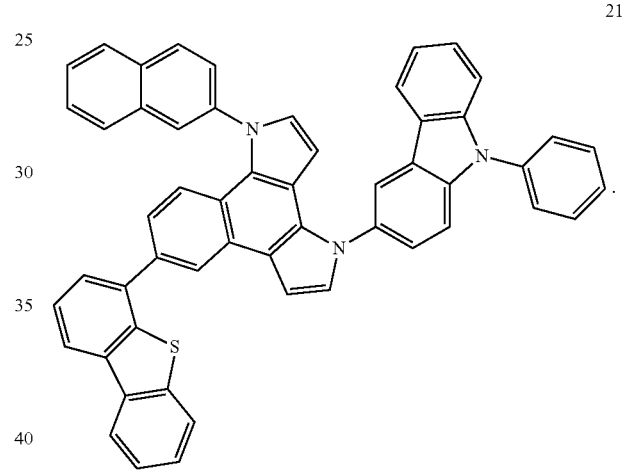

According to another embodiment of the present invention, an organic light-emitting device includes a first electrode, a second electrode, and an organic layer between the first electrode and the second electrode, wherein the organic layer includes at least one of the compounds of Formula 1 described above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

In greater detail, the organic layer may be used as an emission layer, for example, may be used in a green phosphorescent layer.

According to an embodiment of the present invention, the organic light emitting device includes an electron injection layer, an electron transport layer, an emission layer, a hole injection layer, a hole transport layer, and an H-functional layer. The emission layer includes a compound according to an embodiment of the present invention, and the emission layer may further include an anthracene-based compound, an arylamine-based compound, or a styryl-based compound.

According to another embodiment of the present invention, the organic light emitting device includes an emission layer, and may further include an electron injection layer, an electron transport layer, a hole injection layer, a hole transport layer, or an H-functional layer. Any one layer of a red layer, a green layer, a blue layer, and a white layer in the emission layer may include a phosphorescent compound, and the hole injection layer, the hole transport layer, and the H-functional may include a charge generating material. The charge-generating material may be, for example, a p-dopant, and the p-dopant may be one of quinone derivatives, metal oxides, and cyano group-containing compounds.

According to another embodiment of the present invention, the organic layer includes an electron transport layer, and the electron transport layer may further include a metal complex. The metal complex may be a lithium (Li) complex.

The term "organic layer" as used herein refers to a single and/or multiple layers interposed between the first electrode and the second electrode of the OLED.

The organic layer includes an emission layer, and the emission layer may include the compound represented by Formula 1. In some embodiments, the organic layer may include at least one of the hole injection layer, the hole transport layer, and the H-functional layer, and the compound described above may be included in at least one of the hole injection layer, the hole transport layer, and the H-functional layer.

The drawing schematically illustrates cross-section of an OLED according to an embodiment of the present invention. Hereinafter, a structure and a method of manufacturing the OLED according to an embodiment of the present invention will be described in more detail with reference to the drawing.

A substrate (not shown) may be any substrate that is used in existing OLEDs. In some embodiments, the substrate is a glass substrate or a transparent plastic substrate with strong mechanical strength, thermal stability, transparency, surface smoothness, ease of handling, and/or water resistance.

A first electrode may be formed by depositing or sputtering a first electrode-forming material onto a surface of the substrate. When the first electrode is an anode, a material having a high work function may be used as the first electrode-forming material to facilitate hole injection. The first electrode may be a reflective electrode or a transmission electrode. ITO, IZO, SnO$_2$, ZnO, or the like, which is transparent and has excellent conductivity may be used as the first electrode-forming material. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layer structure or a multi-layer structure including at least two layers. For example, the first electrode may have a three-layered structure of ITO/Ag/ITO, but is not limited thereto.

An organic layer may be disposed on the first electrode.

The organic layer may include a hole injection layer, a hole transport layer, a buffer layer (not shown), an emission layer, an electron transport layer, an electron injection layer, and/or the like.

The hole injection layer may be formed on the first electrode by using various methods such as vacuum deposition, spin coating, casting, Langmuir-Blodgett (LB) deposition, or the like.

When the hole injection layer is formed using vacuum deposition, vacuum deposition conditions may vary according to the compound that is used to form the hole injection layer, and the desired structure and thermal properties of the hole injection layer to be formed. For example, the vacuum deposition may be performed at a temperature of about 100° C. to about 500° C., a pressure of about $10^{-8}$ torr to about $10^{-3}$ torr, and a deposition rate of about 0.01 Å/sec to about 100 Å/sec. However, the deposition conditions are not limited thereto.

When the hole injection layer is formed using spin coating, the coating conditions may vary according to the compound that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The hole injection material layer may be formed of any material that is commonly used to form a hole injection layer. Non-limiting examples of the material that may be used to form the hole injection layer are N,N'-diphenyl-N,N'-bis-[4-(phenyl-m-tolyl-amino)-phenyl]-biphenyl-4,4'-diamine, (DNTPD), a phthalocyanine compound such as copper phthalocyanine, 4,4',4''-tris(3-methylphenylphenylamino)triphenylamine (m-MTDATA), N,N'-di(1-naphthyl-N,N'-diphenylbenzidine) (NPB), TDATA, 2-TNATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonic acid (Pani/CSA), and (polyaniline)/poly(4-styrenesulfonate) (PANI/PSS):

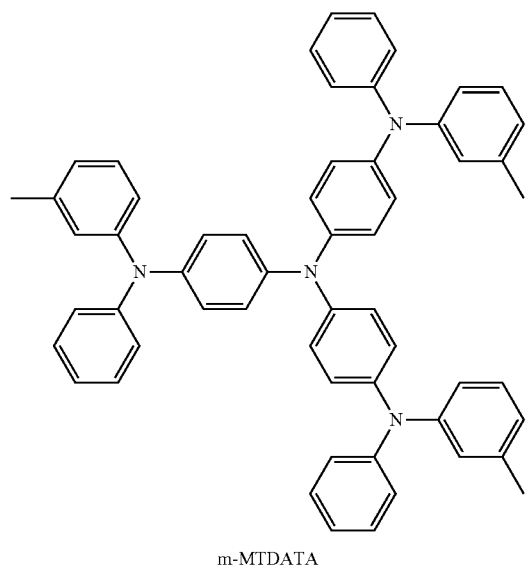

m-MTDATA

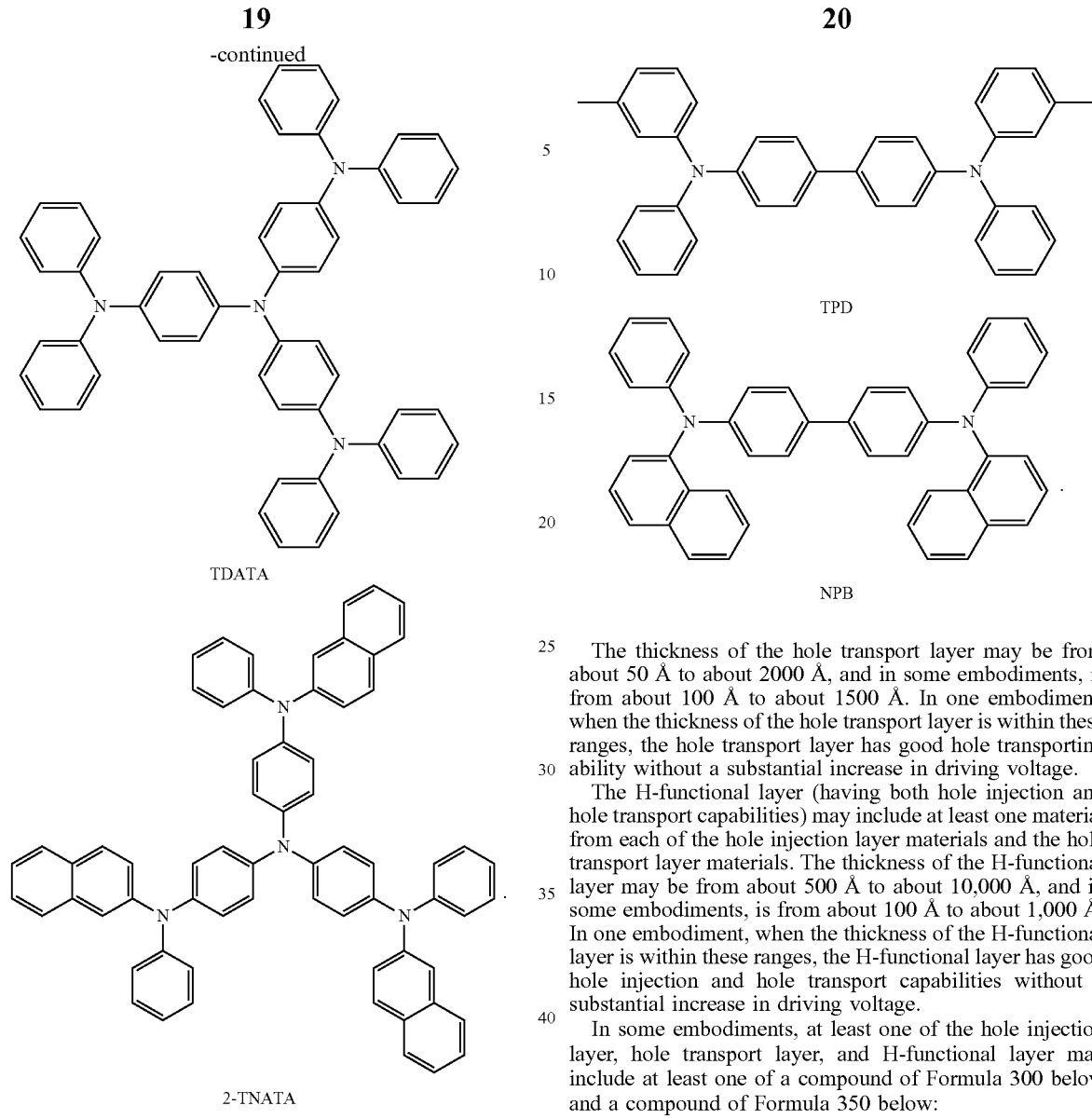

TDATA

2-TNATA

TPD

NPB

The thickness of the hole injection layer may be from about 100 Å to about 10000 Å, and in some embodiments, is from about 100 Å to about 1000 Å. In one embodiment, when the thickness of the hole injection layer is within these ranges, the hole injection layer has good hole injecting ability without a substantial increase in driving voltage.

Then, the hole transport layer may be formed on the hole injection layer by using various methods such as vacuum deposition, spin coating, casting, Langmuir-Blodgett (LB) deposition, or the like. When the hole transport layer is formed using vacuum deposition or spin coating, the conditions for deposition and coating may be similar to those for the formation of the hole injection layer, though the conditions for the deposition and coating may vary according to the compound that is used to form the hole transport layer.

Any suitable hole transport material may be used as the hole transport material. Non-limiting examples of suitable hole transport material are carbazole derivatives, such as N-phenylcarbazole or polyvinylcarbazole, N,N'-bis(3-methylphenyl-N,N'-diphenyl-[1,1-biphenyl]-4,4'-diamine (TPD), 4,4',4''-tris(N-carbazolyl grouptriphenylamine (TCTA), and N,N'-di(1-naphthyl-N,N'-diphenylbenzidine) (NPB).

The thickness of the hole transport layer may be from about 50 Å to about 2000 Å, and in some embodiments, is from about 100 Å to about 1500 Å. In one embodiment, when the thickness of the hole transport layer is within these ranges, the hole transport layer has good hole transporting ability without a substantial increase in driving voltage.

The H-functional layer (having both hole injection and hole transport capabilities) may include at least one material from each of the hole injection layer materials and the hole transport layer materials. The thickness of the H-functional layer may be from about 500 Å to about 10,000 Å, and in some embodiments, is from about 100 Å to about 1,000 Å. In one embodiment, when the thickness of the H-functional layer is within these ranges, the H-functional layer has good hole injection and hole transport capabilities without a substantial increase in driving voltage.

In some embodiments, at least one of the hole injection layer, hole transport layer, and H-functional layer may include at least one of a compound of Formula 300 below and a compound of Formula 350 below:

Formula 300

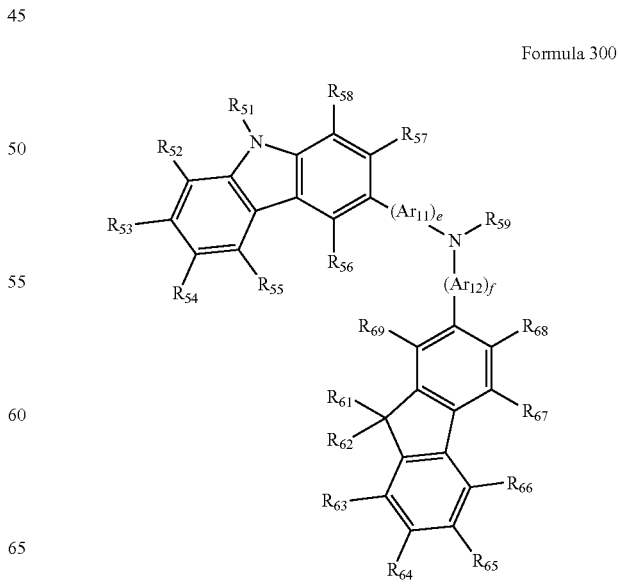

-continued

Formula 350

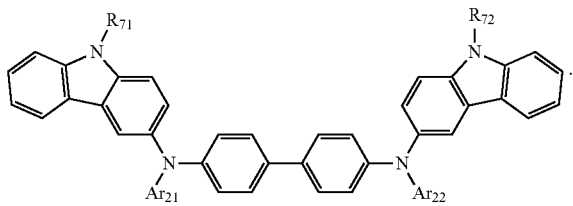

In Formulae 300 and 350 above, $Ar_{11}$, $Ar_{12}$, $Ar_{21}$ and $Ar_{22}$ may be, each independently, a substituted or unsubstituted $C_5$-$C_{60}$ arylene group.

In Formula 300 above, e and f may be, each independently, an integer of 0 to 5, or 0, 1, or 2. For example, e may be 1, and f may be 0, but are not limited thereto.

In Formulae 300 and 350 above, $R_{51}$ to $R_{58}$, $R_{61}$ to $R_{69}$, $R_{71}$, and $R_{72}$ may be, each independently, a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$ and $R_{71}$ and $R_{72}$ may be, each independently, a hydrogen atom; a deuterium atom; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group (for example, a methyl group, an ethyl group, a propyl group, a butyl group, a pentyl group, a hexyl group, or the like);

a $C_1$-$C_{10}$ alkoxy group (for example, a methoxy group, an ethoxy group, a propoxy group, a butoxy group, a pentoxy group, or the like);

a $C_1$-$C_{10}$ alkyl group or a $C_1$-$C_{10}$ alkoxy group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid or a salt thereof;

a phenyl group; a naphthyl group; an anthryl group; a fluorenyl group; a pyrenyl group; or a phenyl group, a naphthyl group, an anthryl group, a fluorenyl group or a pyrenyl group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group and a $C_1$-$C_{10}$ alkoxy group, but are not limited thereto.

In Formula 300 above, $R_{59}$ may be one of a phenyl group; a naphthyl group; an anthryl group; a biphenyl group; a pyridyl group; and a phenyl group, a naphthyl group, an anthryl group, a biphenyl group and a pyridyl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{20}$ alkyl group, and a substituted or unsubstituted $C_1$-$C_{20}$ alkoxy group.

According to an embodiment of the present invention, the compound of Formula 300 above is a compound represented by Formula 300A below, but is not limited thereto:

Formula 300A

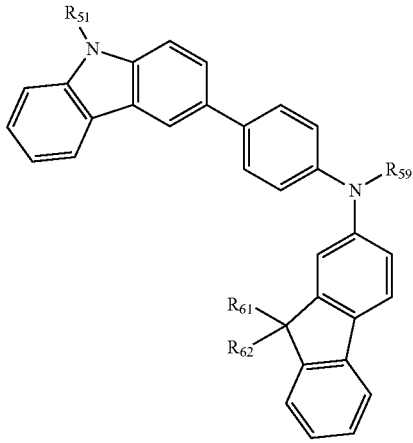

In Formula 300A, a detailed description of $R_{51}$, $R_{59}$, $R_{61}$ and $R_{62}$ may be as defined above.

In some non-limiting embodiments, at least one of the hole injection layer, hole transport layer, and H-functional layer may include at least one of the compounds represented by Formulae 301 to 320 below, but is not limited thereto:

301

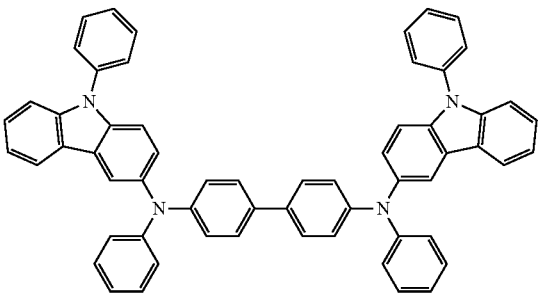

302

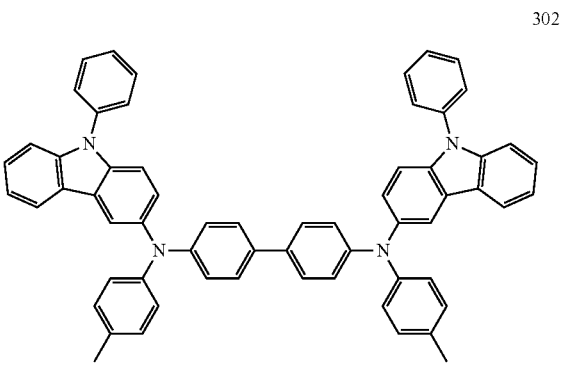

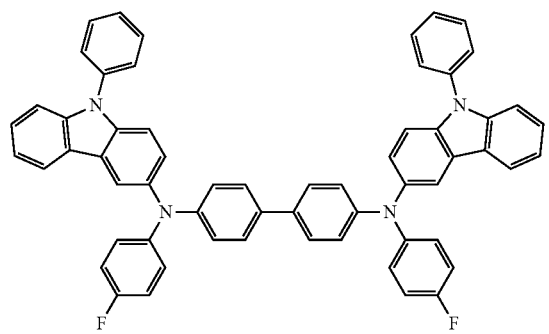
303
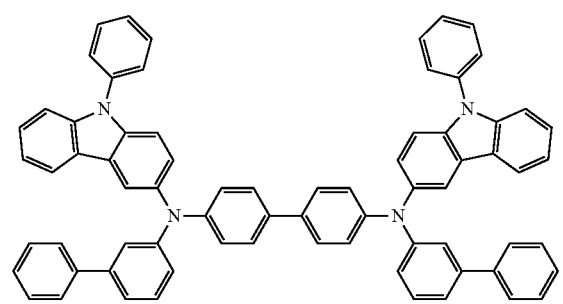
307
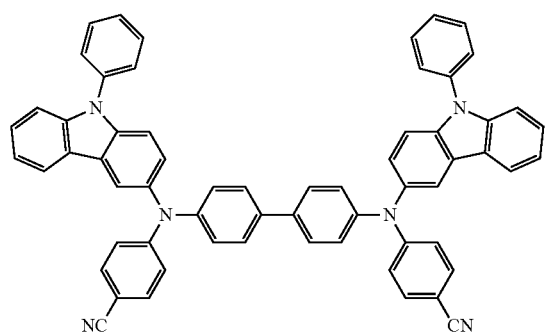
304
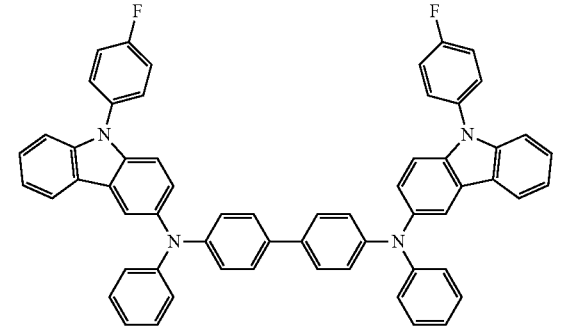
308
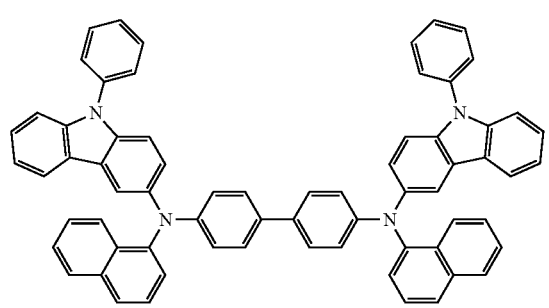
305
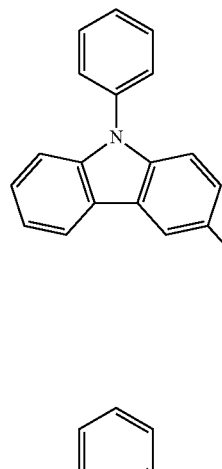
309
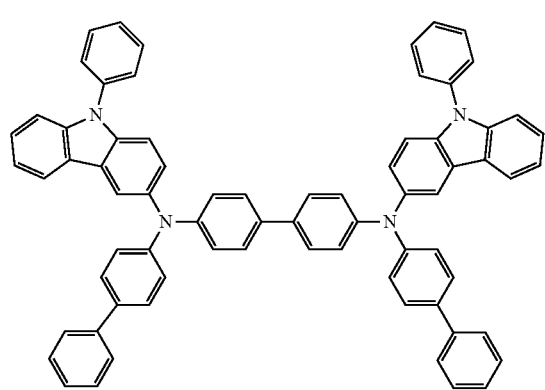
306
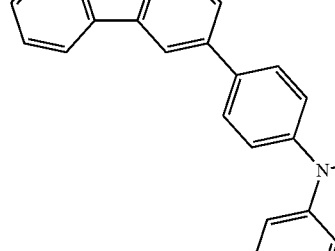
310

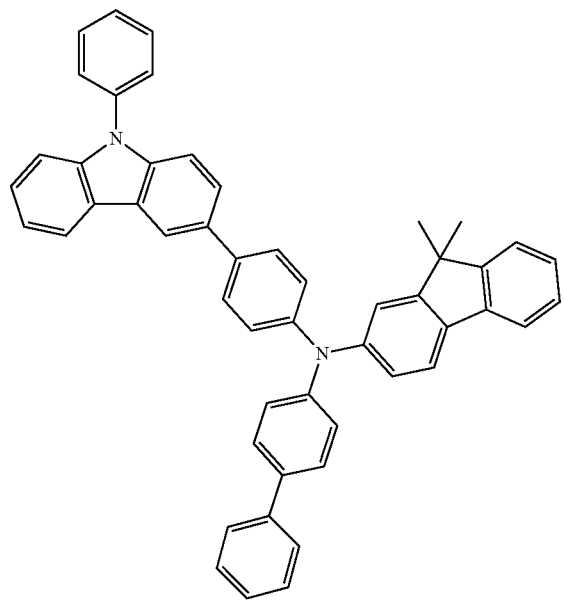
311
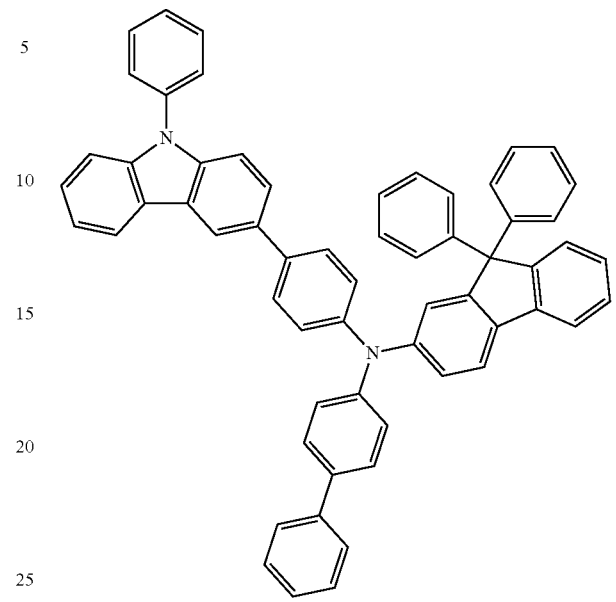
313
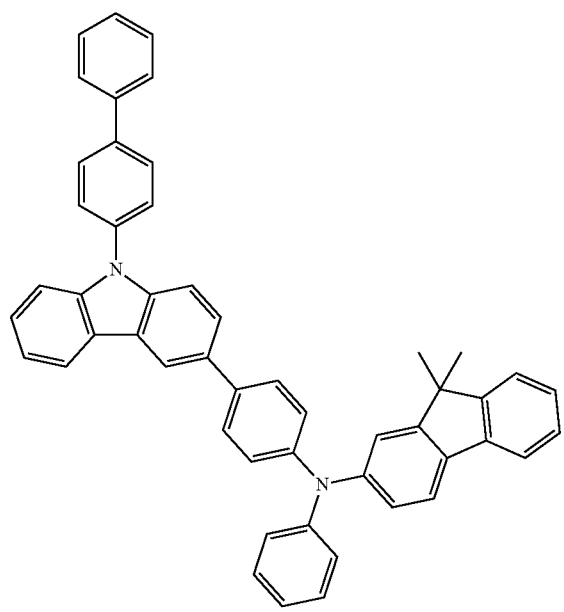
312
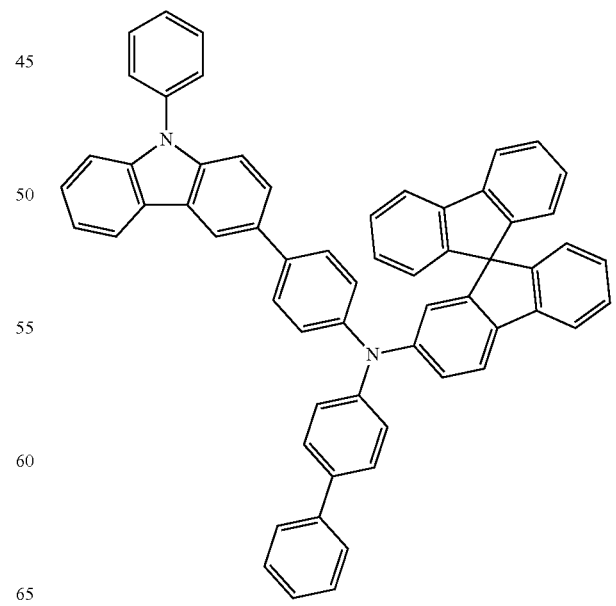
314

315
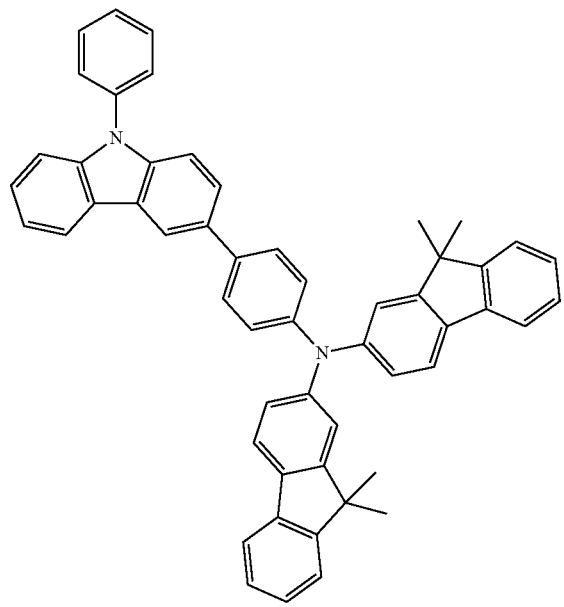
316
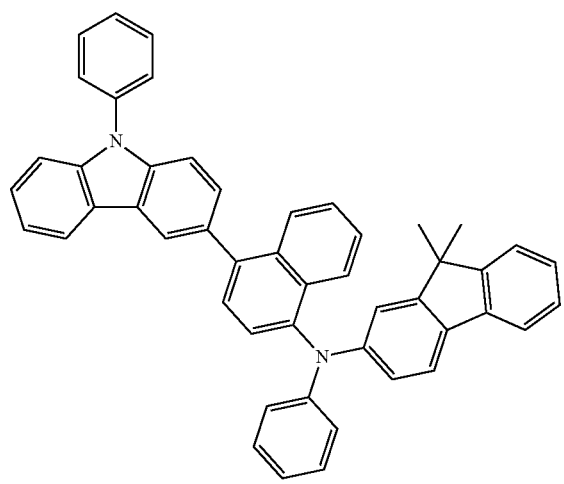
317
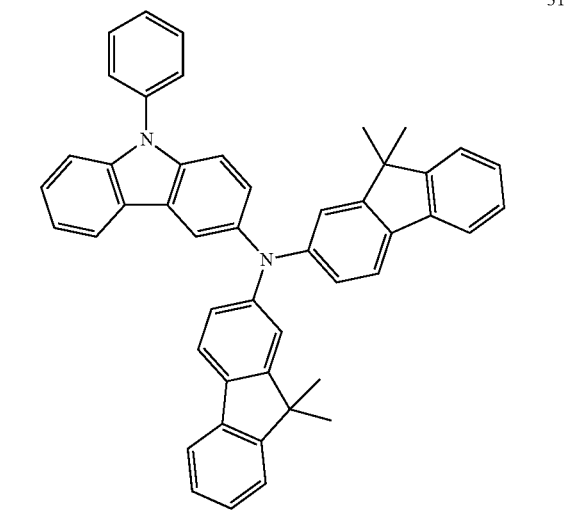
318
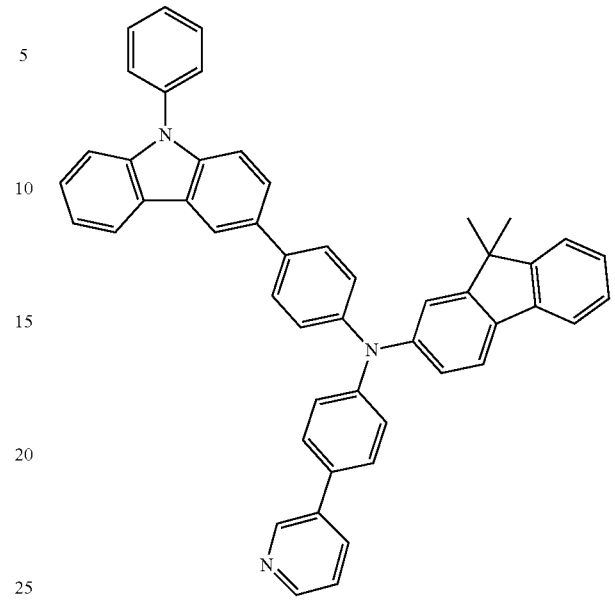
319
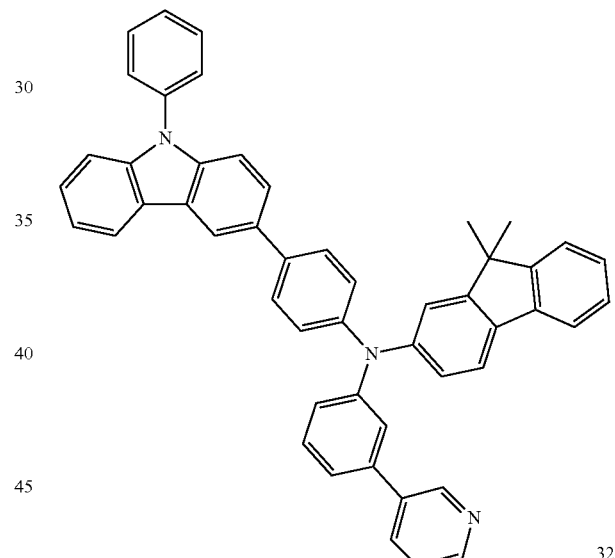
320
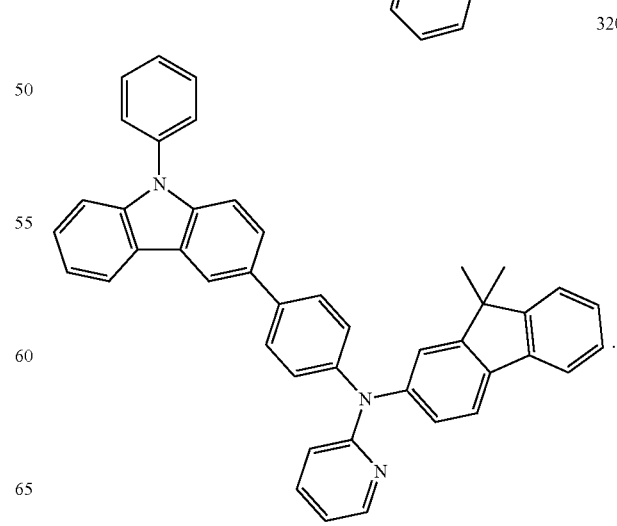

At least one of the hole injection layer, the hole transport layer, and the H-functional layer may further include a charge-generating material to improve layer conductivity, in addition to a suitable hole injection material, hole transport material, and/or material having both hole injection and hole transport capabilities as described above.

The charge-generating material may be, for example, a p-dopant. The p-dopant may be one of quinone derivatives, metal oxides, and cyano-containing compounds, but is not limited thereto. Non-limiting examples of the p-dopant include quinone derivatives such as tetracyanoquinonedimethane (TCNQ), 2,3,5,6-tetrafluoro-tetracyano-1,4-benzoquinonedimethane (F4-TCNQ), or the like; metal oxides such as tungsten oxide, molybdenum oxide, or the like; and cyano-containing compounds such as Compound 200 below.

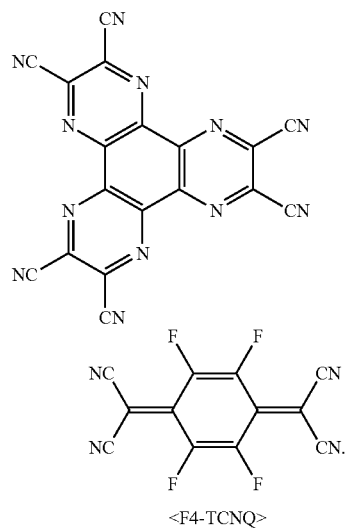

When the hole injection layer, the hole transport layer, or the H-functional layer further include a charge-generating material, the charge-generating material may be homogeneously dispersed or inhomogeneously distributed in the hole injection layer, the hole transport layer, or the H-functional layer.

A buffer layer may be between the emission layer and at least one of the hole injection layer, hole transport layer, and H-functional layer. The buffer layer may compensate for an optical resonance distance of light according to a wavelength of the light emitted from the emission layer, and thus may increase efficiency. The buffer layer may include any suitable hole injection material or hole transport material. In some other embodiments, the buffer layer includes the same material as one of the materials included in the hole injection layer, the hole transport layer, and the H-functional layer that underlay the buffer layer.

Then, the emission layer (EML) may be formed on the hole transport layer, H-functional layer, or buffer layer by vacuum deposition, spin coating, casting, LB deposition, or the like. When the emission layer is formed using vacuum deposition or spin coating, the deposition and coating conditions may be similar to those for the formation of the hole injection layer, though the conditions for deposition and coating may vary according to the material that is used to form the emission layer.

The emission layer may be formed by using various suitable emission materials, in addition to a compound according to an embodiment of the present invention and may be formed by a host and a dopant. As a dopant, a suitable fluorescent dopant and a suitable phosphorescent dopant may both be used.

For example, as a suitable host, Alq$_3$, CBP(4,4'-N,N'-dicarbazole-biphenyl), PVK(poly(n-vinylcabazole)), 9,10-di(naphthalene-2-yl)anthracene (ADN), TCTA, TPBI (1,3,5-tris(N-phenylbenzimidazole-2-yl)benzene(1,3,5-tris(N-phenylbenzimidazole-2-yl)benzene)), TBADN (3-tert-butyl-9,10-di(naphth-2-yl) anthracene), E3, DSA (distyrylarylene), dmCBP (in Formula below), or Compounds 501 to 509 below may be used, but the host is not limited thereto.

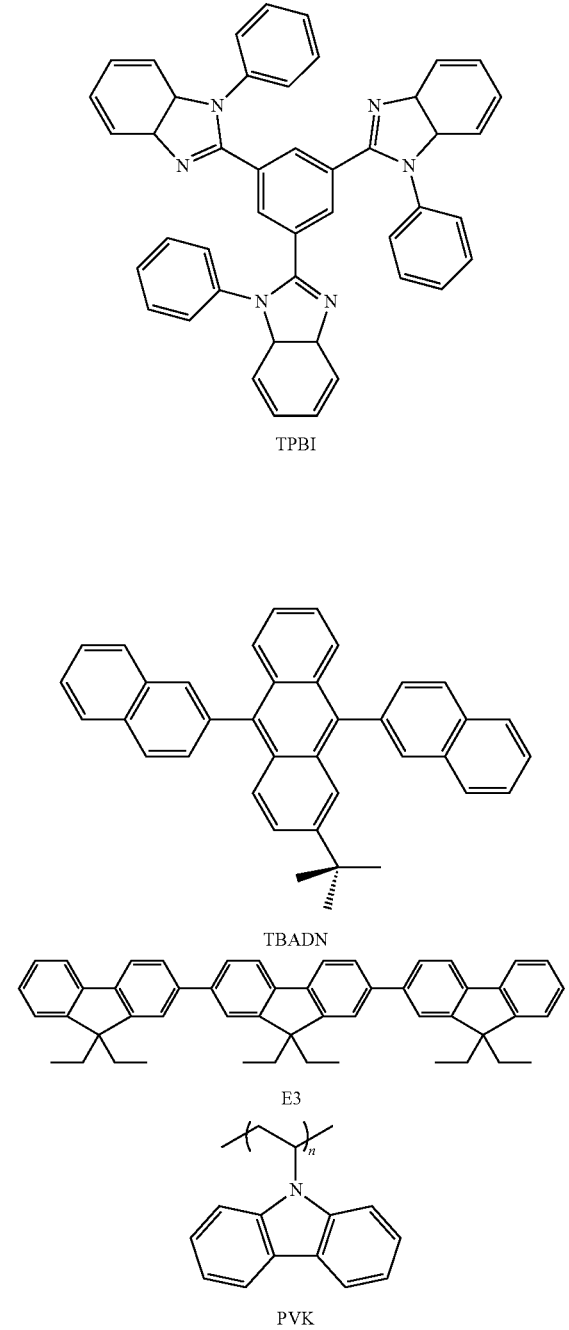

-continued
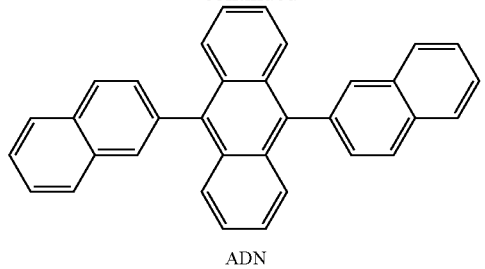
ADN
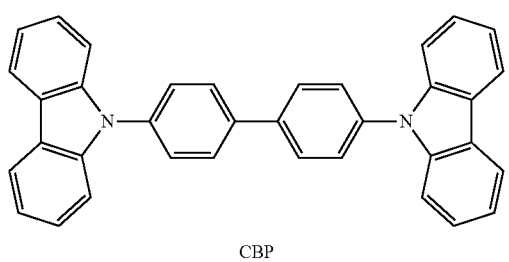
CBP
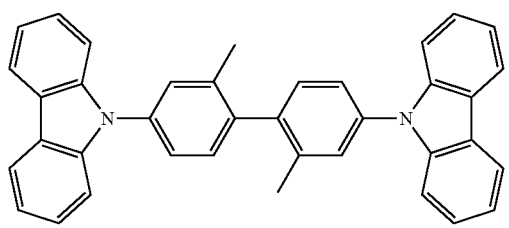
dmCBP
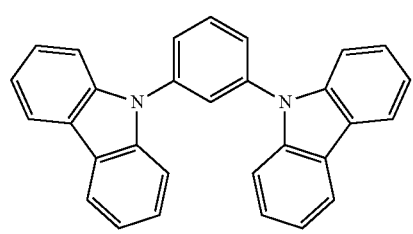
501
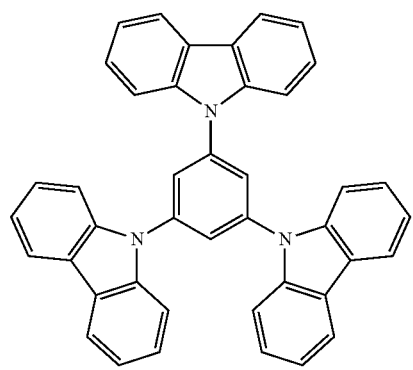
502
-continued
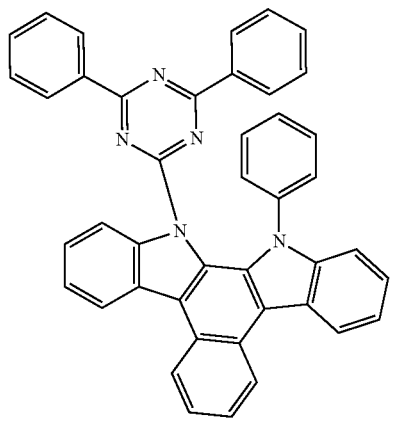
503
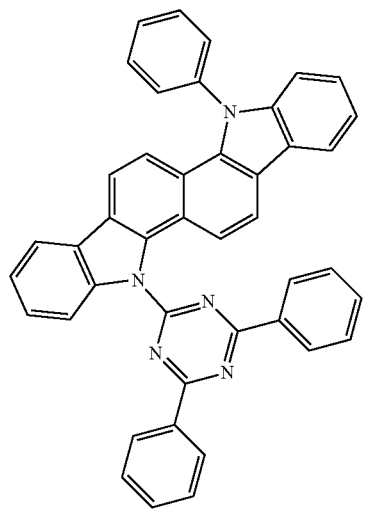
504
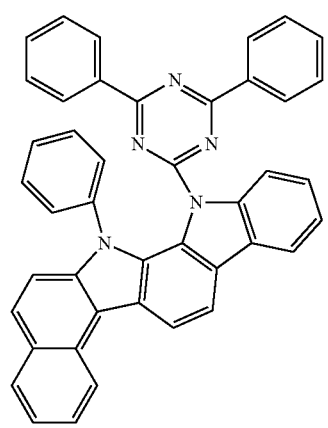
505

-continued

506

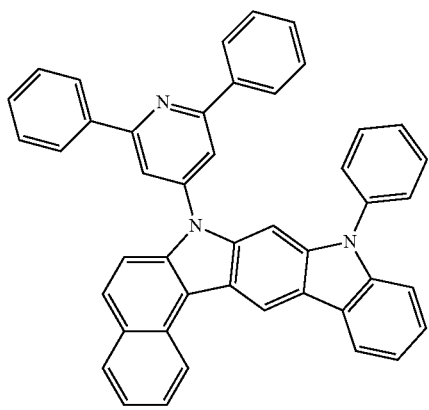

507

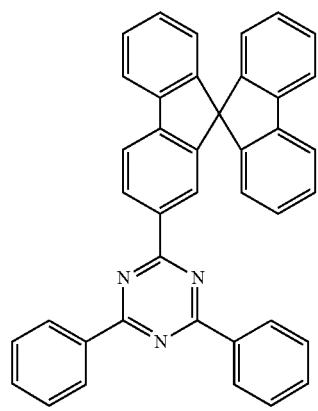

508

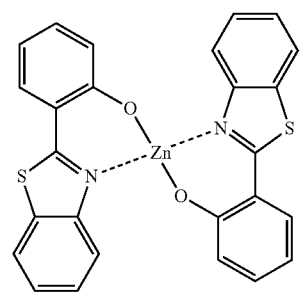

509

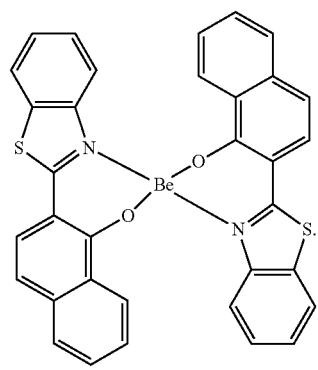

In some embodiments, an anthracene-based compound represented by Formula 400 below is used as another host:

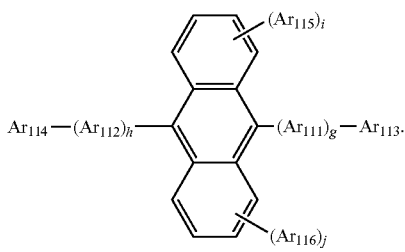

Formula 400

In Formula 400, $Ar_{111}$ and $Ar_{112}$ may be, each independently, a substituted or unsubstituted $C_5$-$C_{60}$ arylene group; $Ar_{113}$ to $Ar_{116}$ may be, each independently, a substituted or unsubstituted $C_1$-$C_{10}$ alkyl group, or a substituted or unsubstituted $C_6$-$C_{60}$ aryl group; and g, h, i and j may be, each independently, an integer of 0 to 4.

For example, in Formula 400 above, $Ar_{111}$ and $Ar_{112}$ may be a phenylene group, a naphthylene group, a phenanthrenylene group, a fluorenyl group, or a pyrenylene group; or a phenylene group, a naphthylene group, a phenanthrenylene group, or a pyrenylene group, each substituted with at least one selected from a phenyl group, a naphthyl group and an anthryl group, but are not limited thereto.

In Formula 400 above, g, h, i and j may be, each independently 0, 1 or 2.

In Formula 400 above, $Ar_{113}$ to $Ar_m$ may be, each independently, a $C_1$-$C_{10}$ alkyl group substituted with at least one selected from a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group and a fluorenyl group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group and a fluorenyl group; and

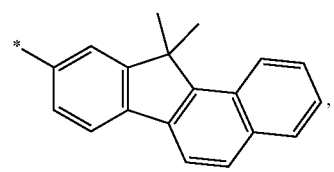 [SMILES: *c1ccc2c(c1)C(C)(C)c1c-2ccc2ccccc12]

but are not limited thereto.

For example, an anthracene-based compound represented by Formula 400 above may be one of the compounds below, but is not limited thereto:

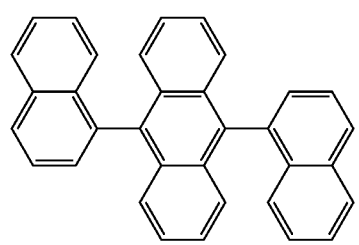

-continued
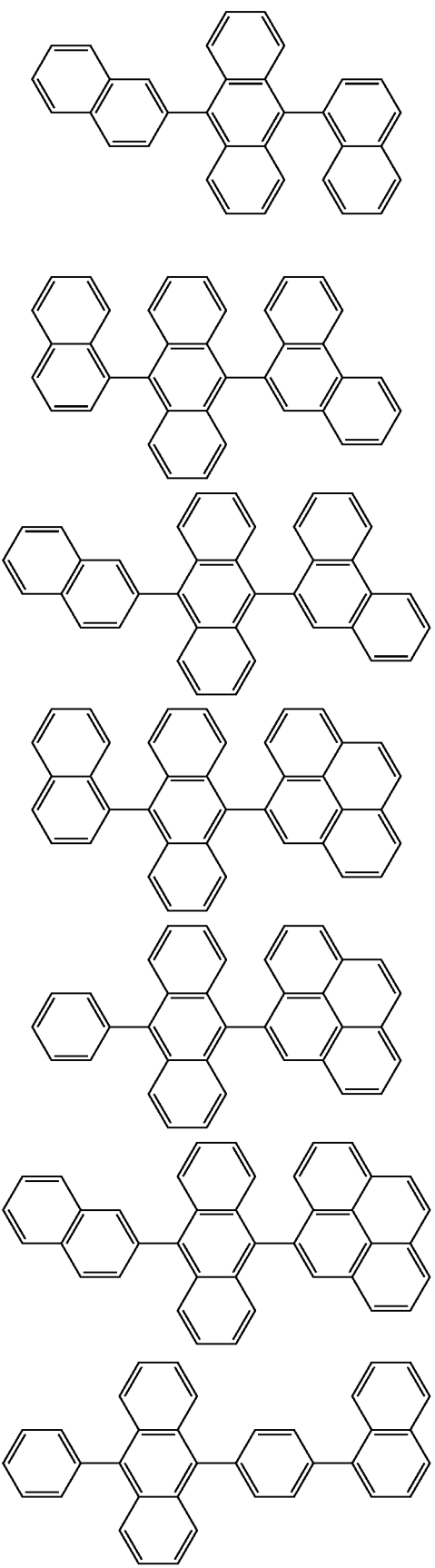
-continued
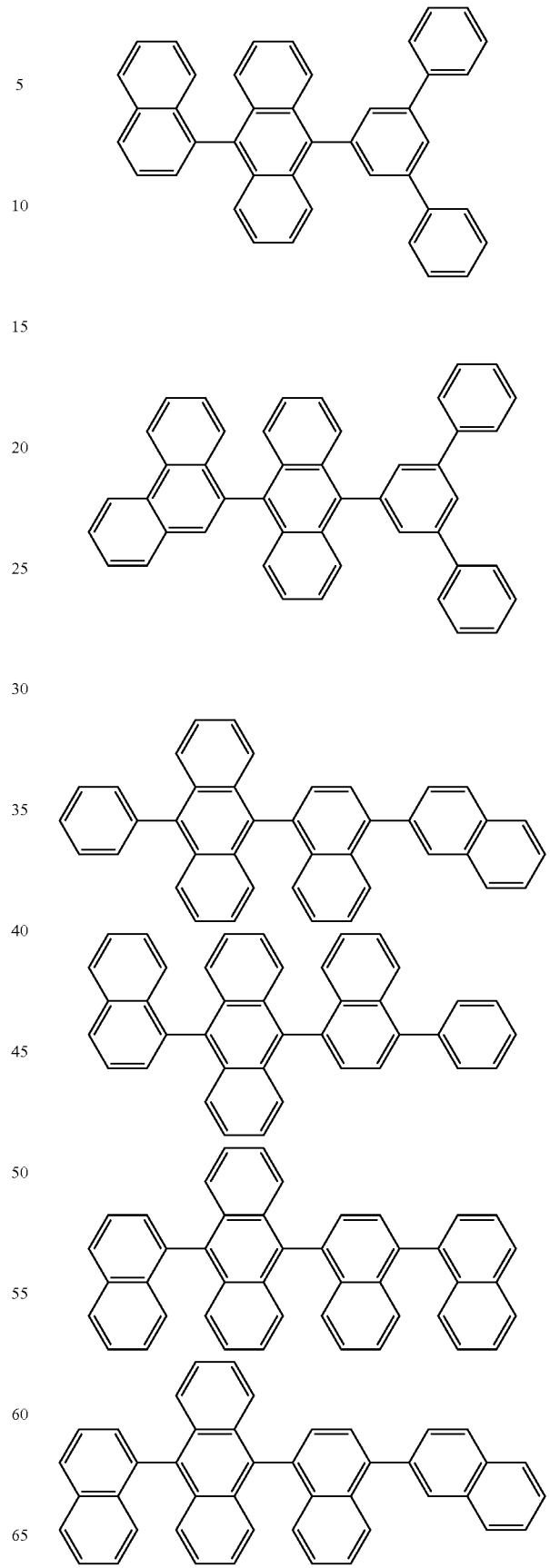

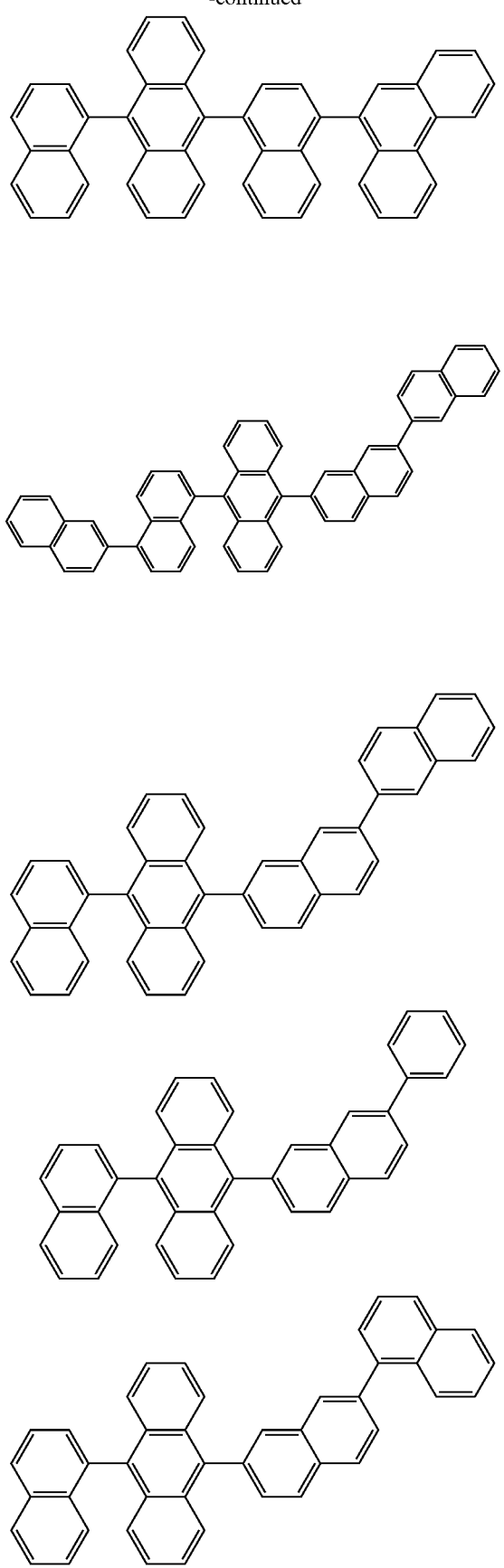
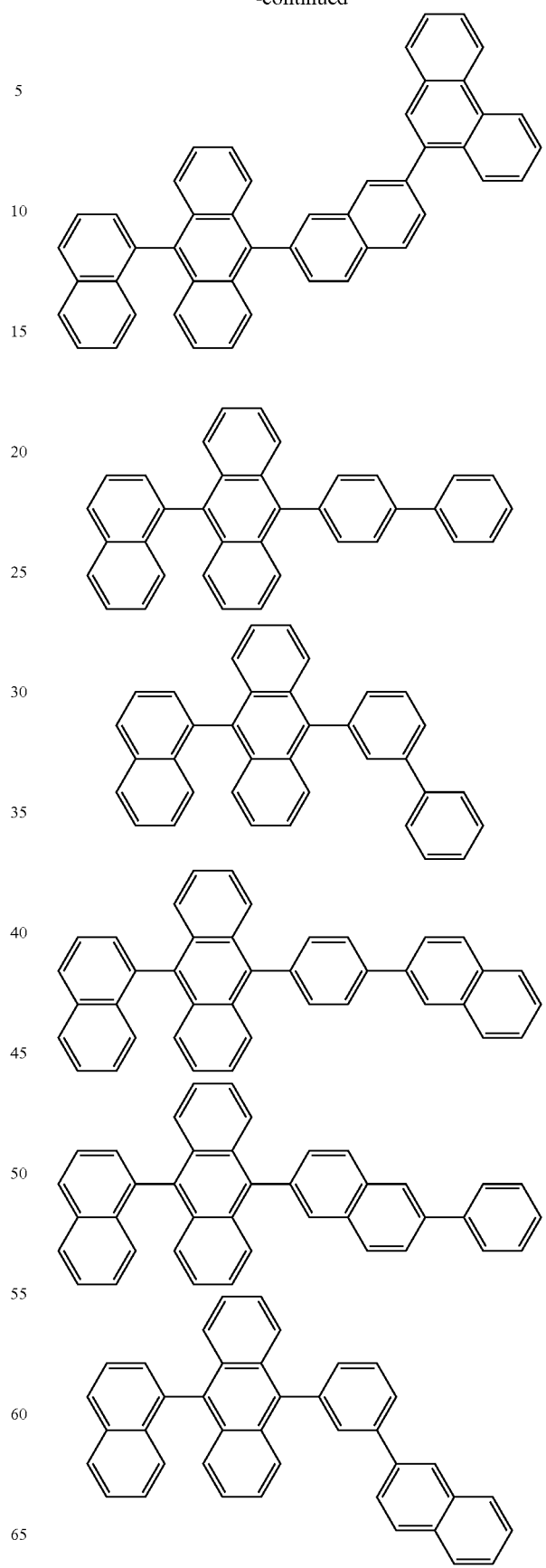

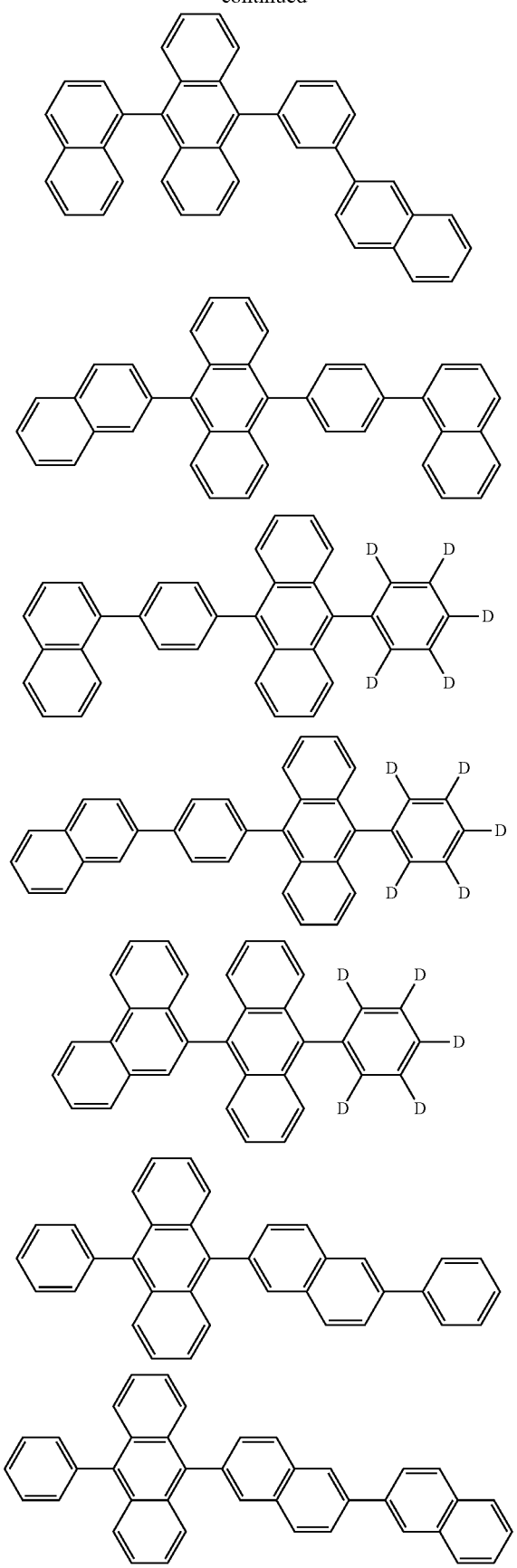

-continued

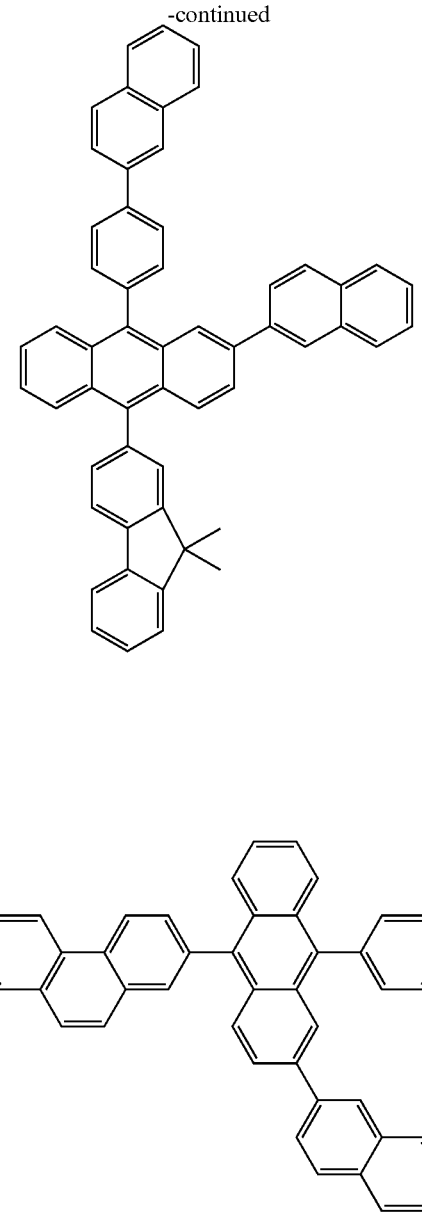

In other embodiments, an anthracene-based compound represented by Formula 401 below is used as another host:

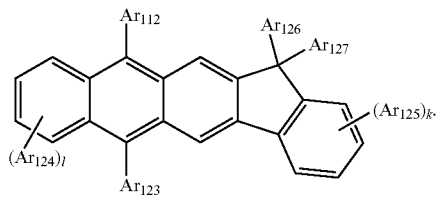

Formula 401

$Ar_{122}$ to $Ar_{125}$ of Formula 401 above are selected from the same groups as $Ar_{113}$ as described in Formula 400 above.

In Formula 401 above, $Ar_{126}$ and $Ar_{127}$ may be, each independently, a $C_1$-$C_{10}$ alkyl group (for example, a methyl group, an ethyl group, or a propyl group).

In Formula 401 above, k and l may be, each independently, an integer of 0 to 4. For example, k and l may be 0, 1, or 2.

For example, the anthracene-based compound represented by Formula 401 may be one compound of the compounds below, but is not limited thereto:

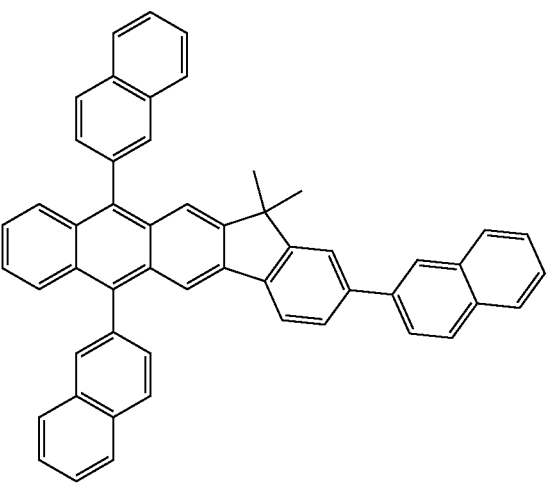

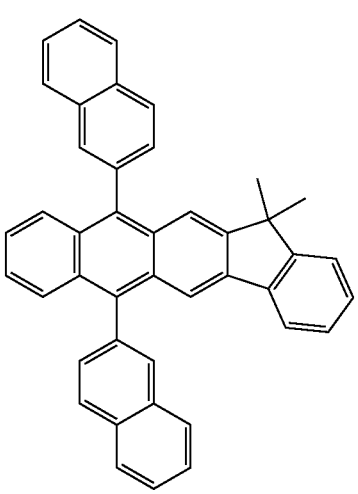

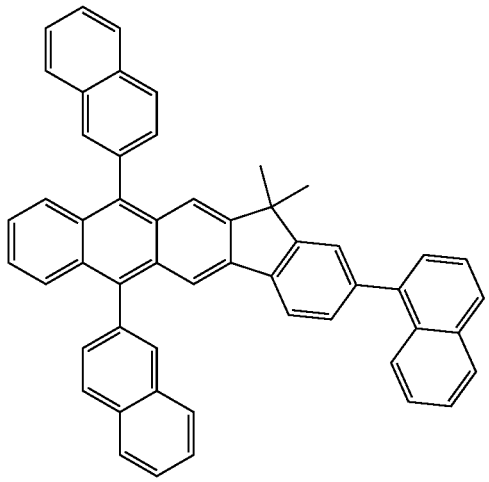

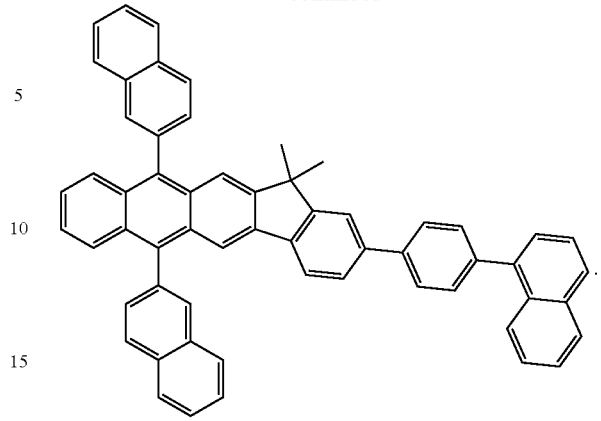

When the organic light-emitting device is a full color organic light-emitting device, the emission layer may be patterned into a red emission layer, a green emission layer, and a blue emission layer.

Also, at least one of the red emission layer, the green emission layer, and the blue emission layer may include a dopant below (ppy=phenylpyridine).

Non-limiting examples of the blue dopant may be compounds represented by the following formulae.

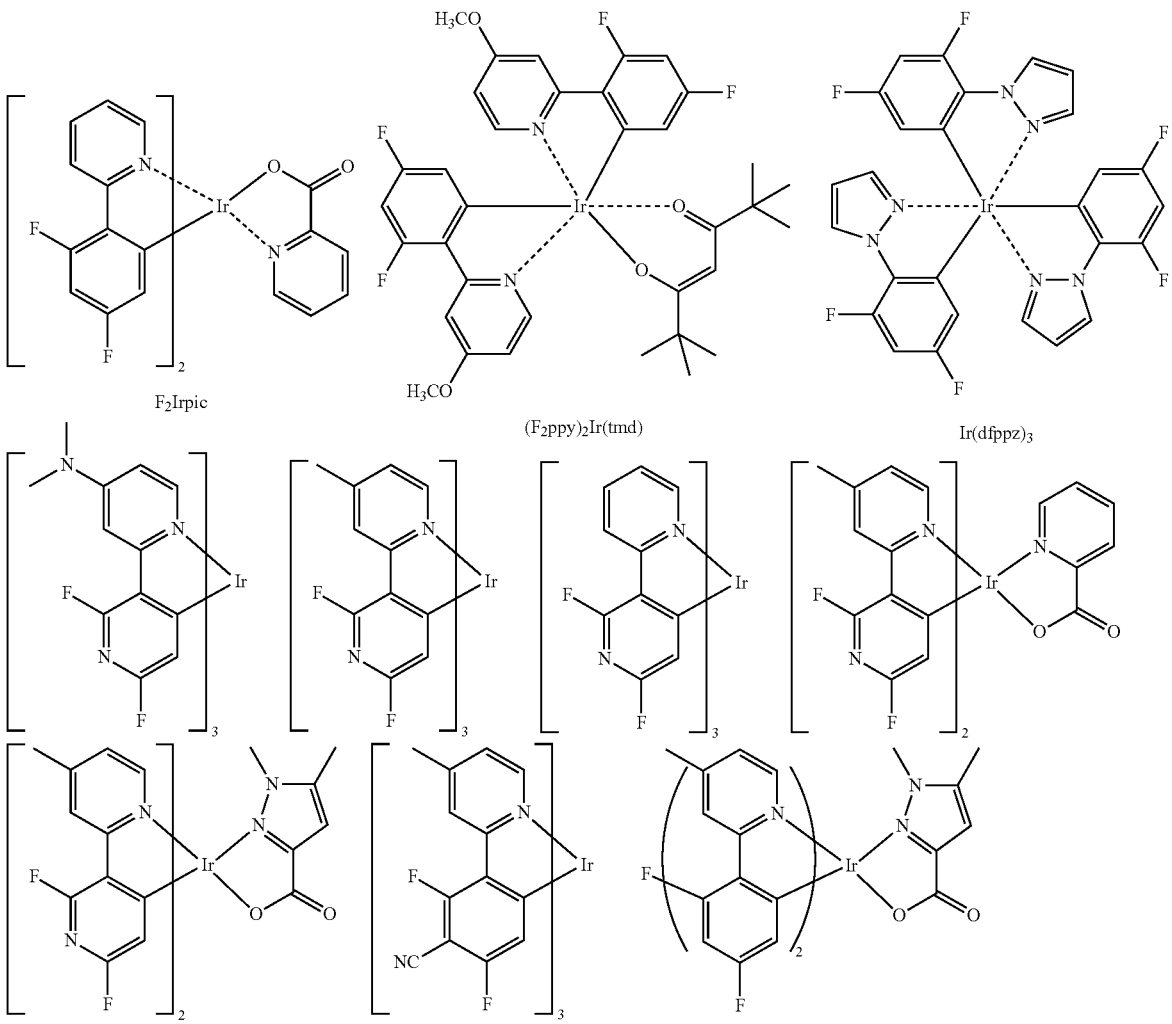

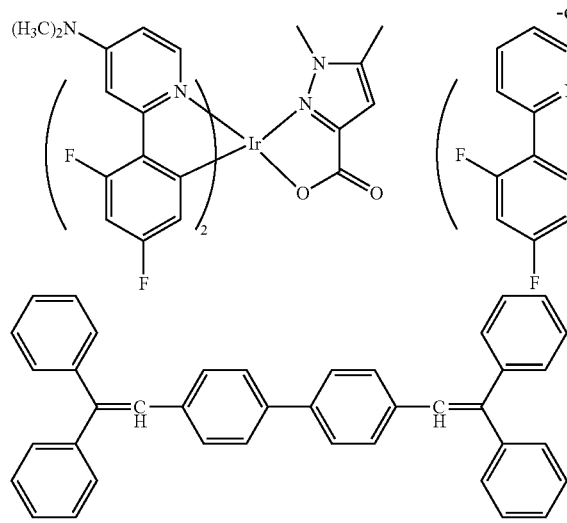
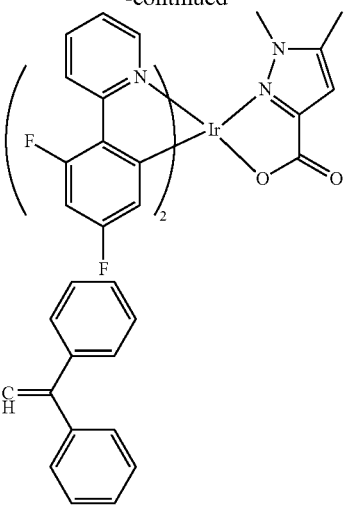
DPVBi
DPAVBi
TBPe
Non-limiting examples of the red dopant may be compounds represented by the following formulae.
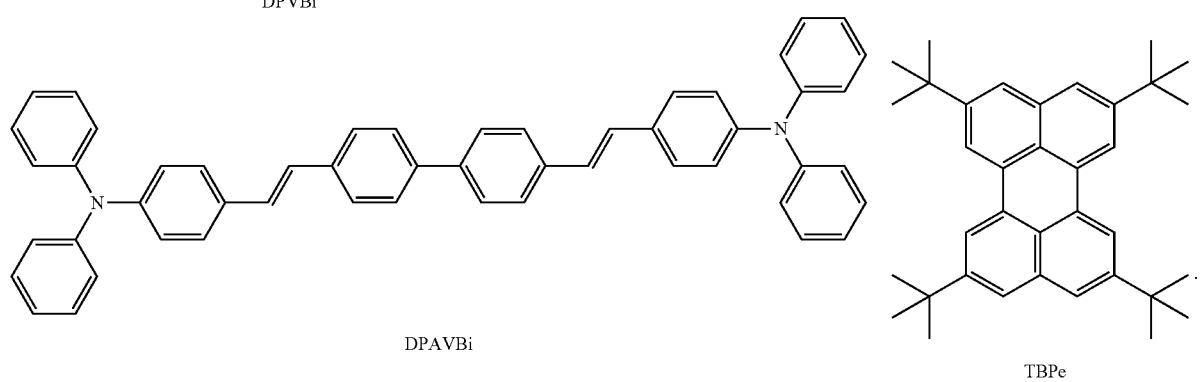
PtOEP
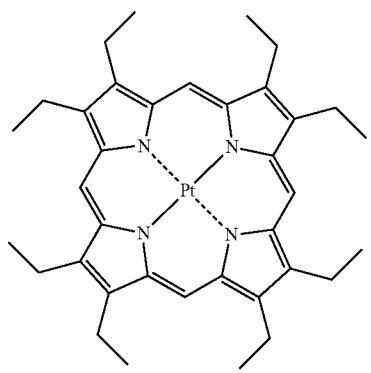
Ir(piq)₃    Btp₂Ir(acac)
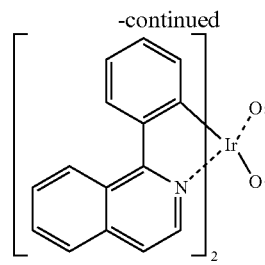
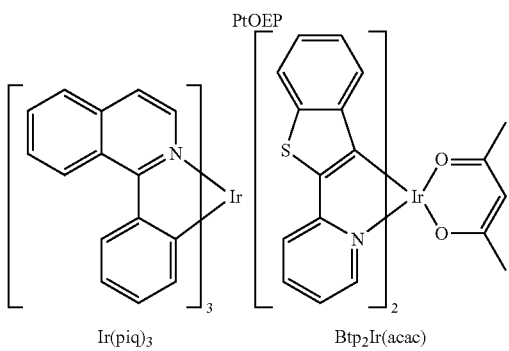
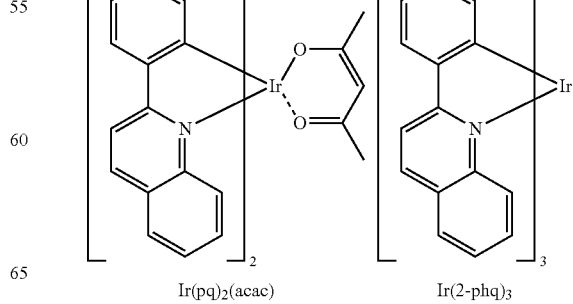
Ir(pq)₂(acac)    Ir(2-phq)₃

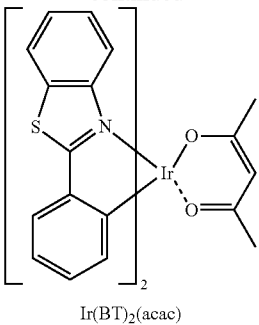
Ir(BT)₂(acac)
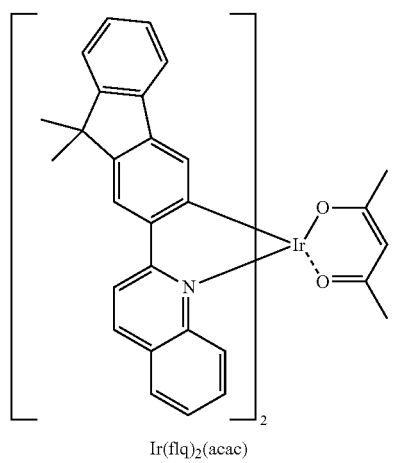
Ir(flq)₂(acac)
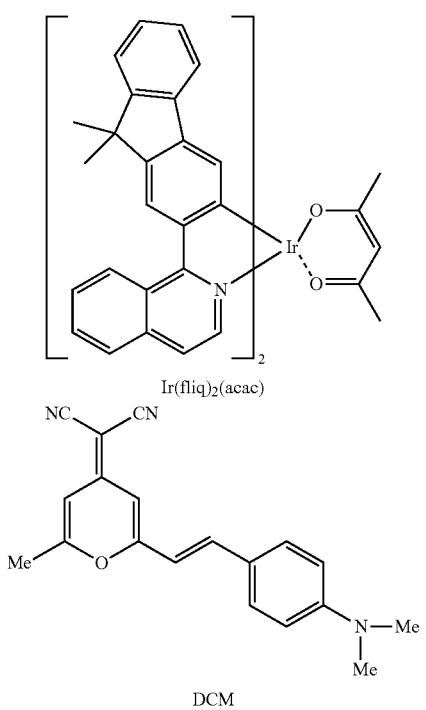
Ir(fliq)₂(acac)
DCM
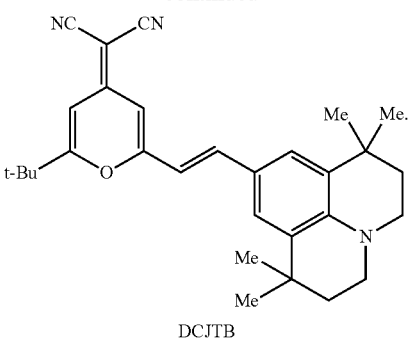 [SMILES: CC(C)(C)C1=CC(=C(C#N)C#N)C=C(/C=C/c2cc3c4c(c2)C(C)(C)CCN4CCC3(C)C)O1]
DCJTB
Non-limiting examples of the green dopant may be compounds represented by the following formulae.
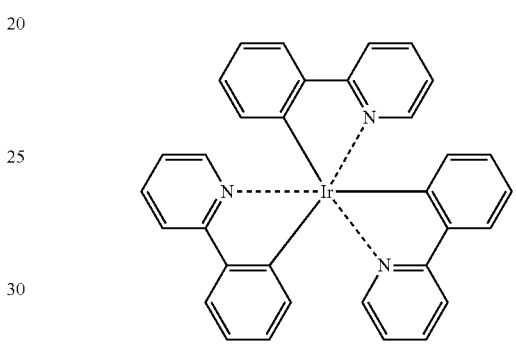
Ir(ppy)₃
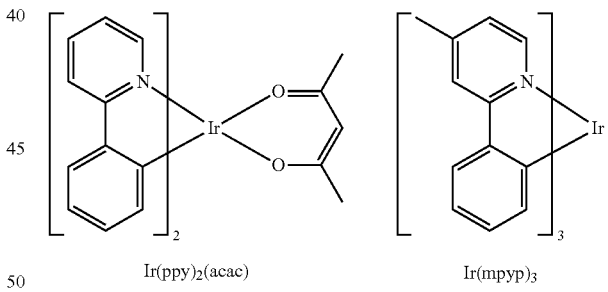
Ir(ppy)₂(acac)          Ir(mpyp)₃
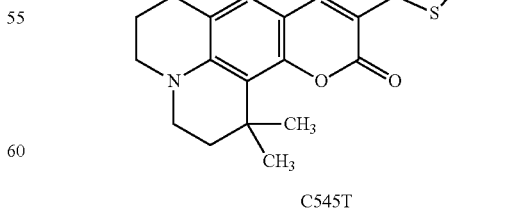
C545T
Also, a dopant that may be included in the emission layer may be a Pd-complex or Pt-complex as described below, but is not limited thereto.

-continued
D1
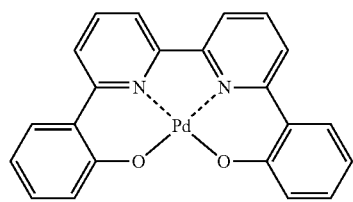
D2
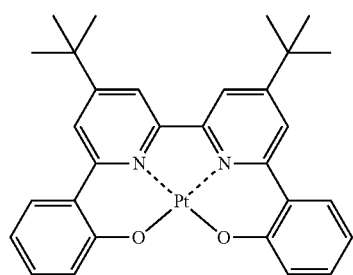
D3
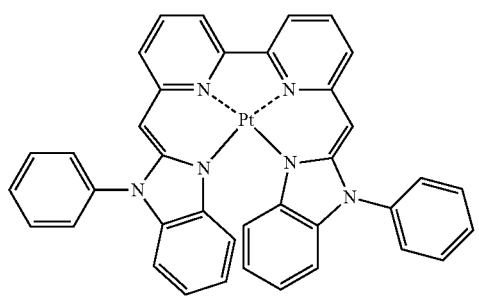
D4
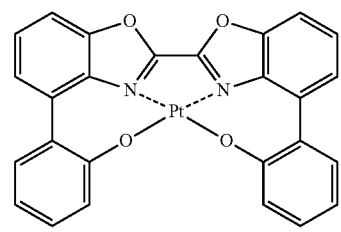
D5
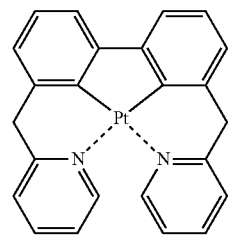
D6
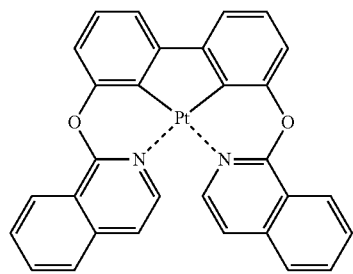
D7
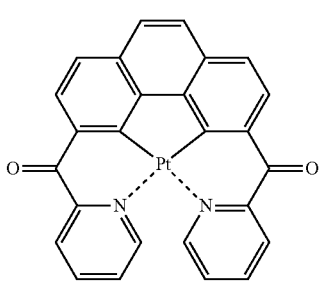
D8
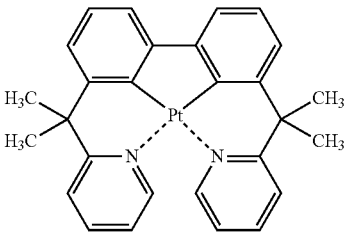
D9
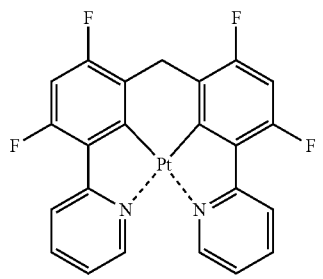
D10
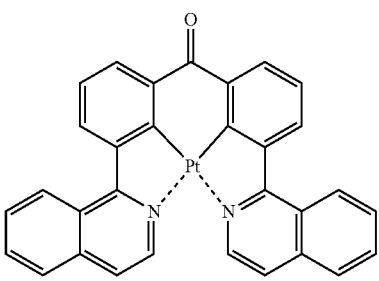
D11
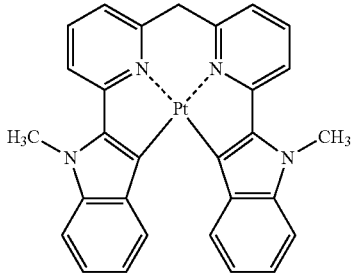
D12
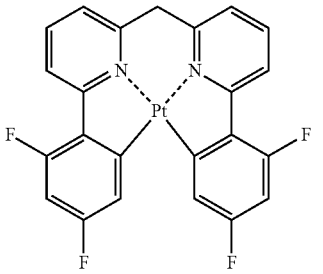

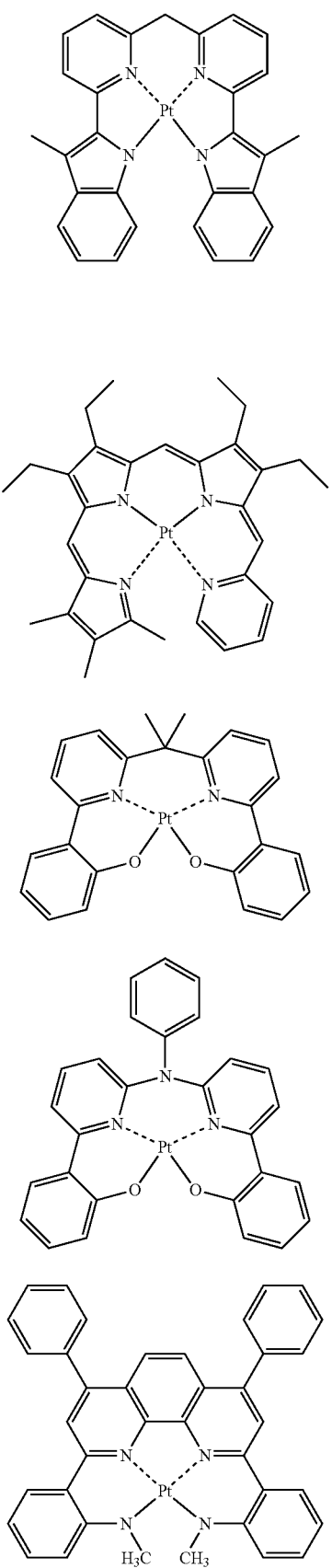
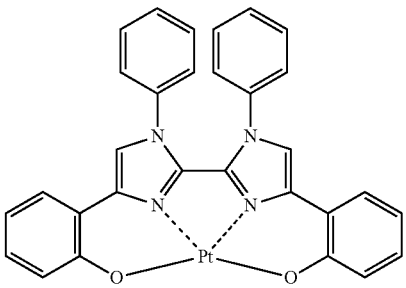
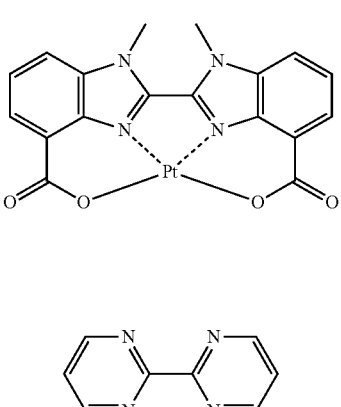
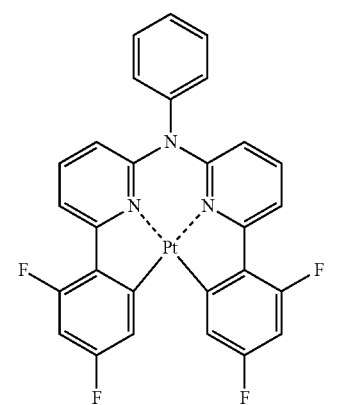
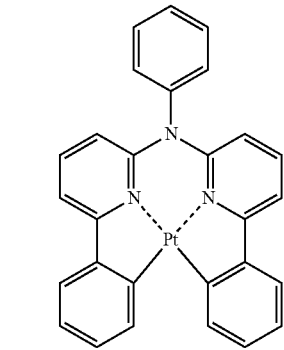

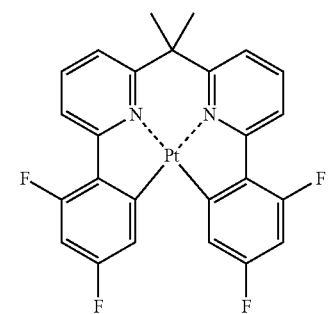
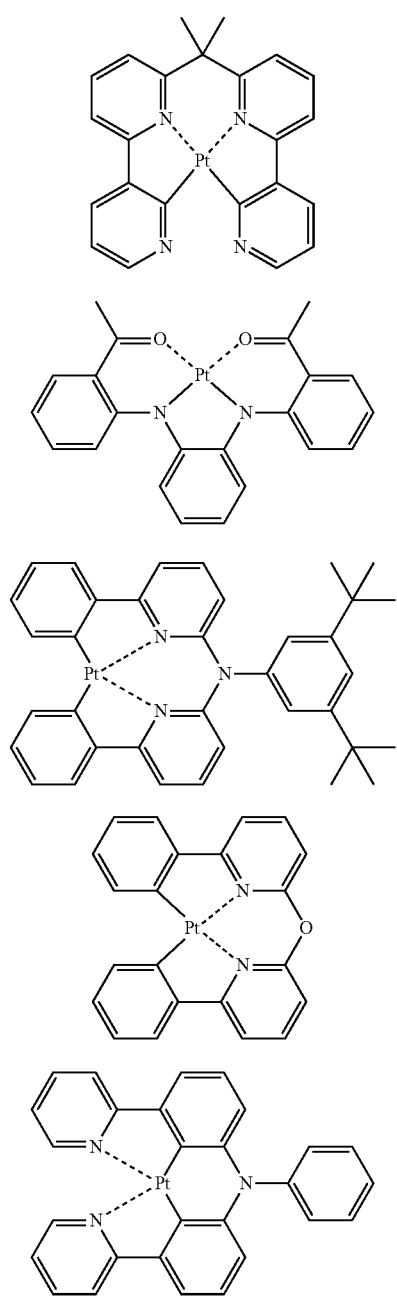
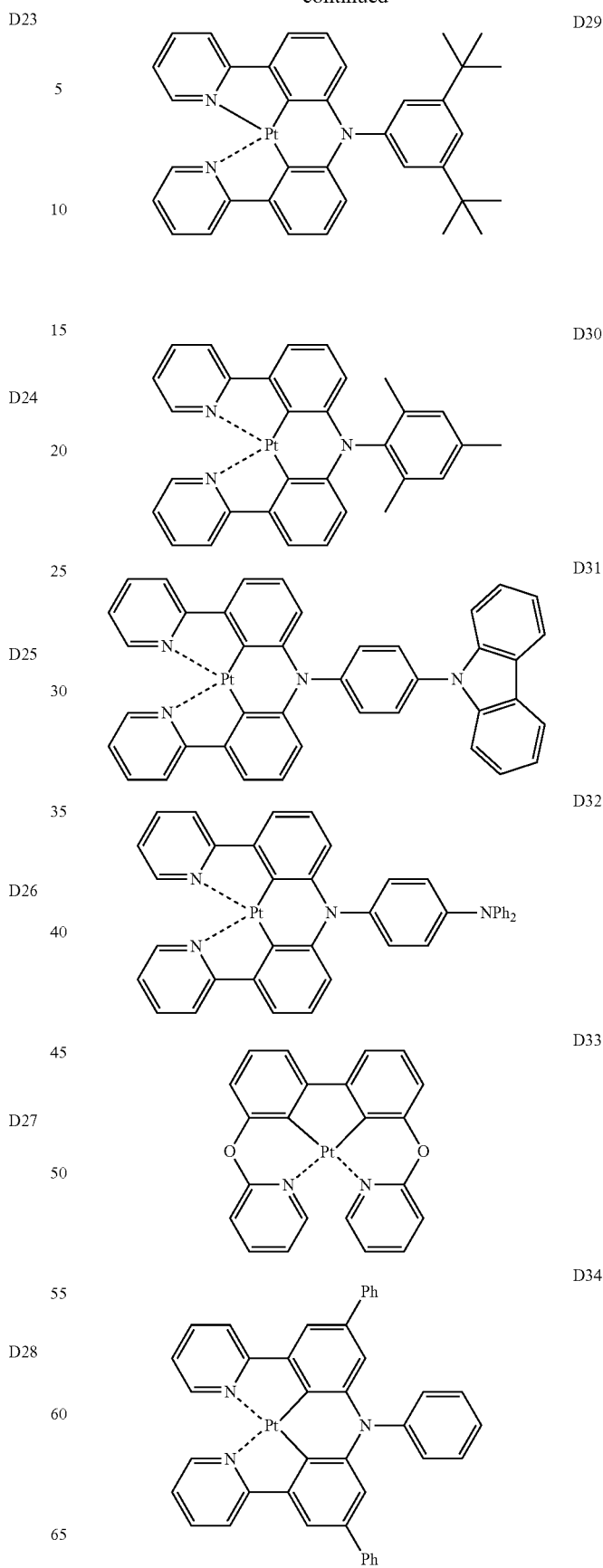

D35 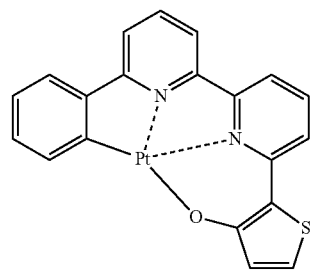
D36 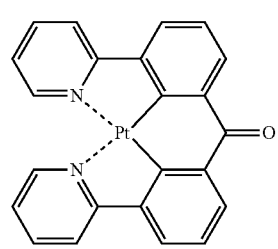
D37 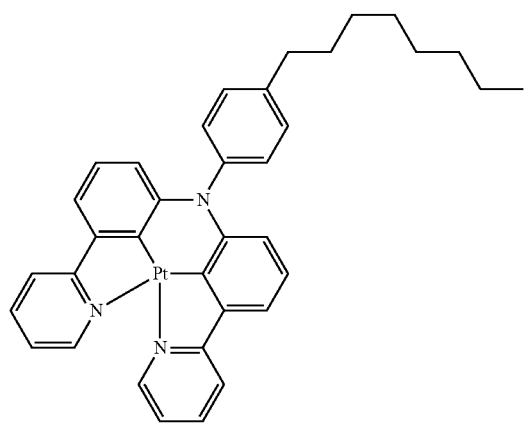
D38 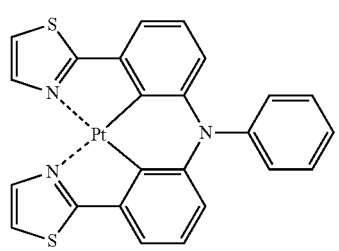
D39 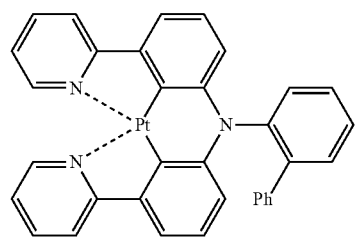
D40 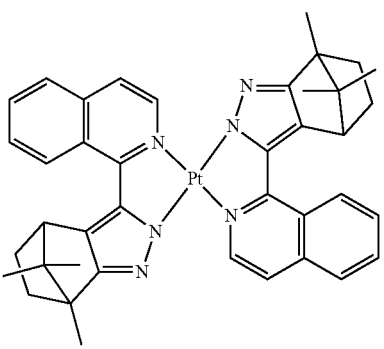
D41 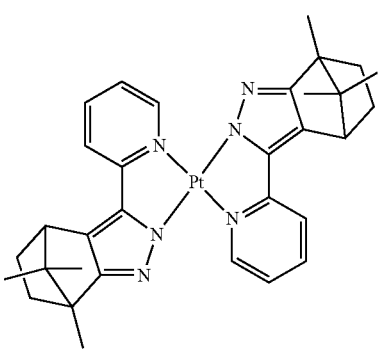
D42 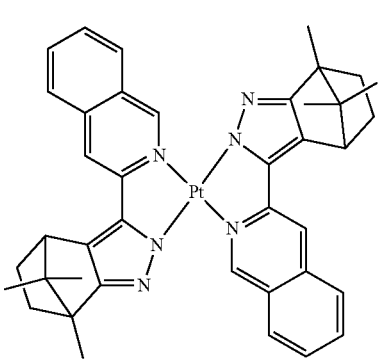
D43 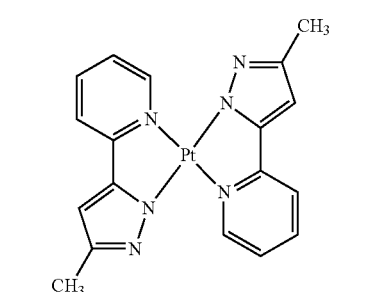
D44 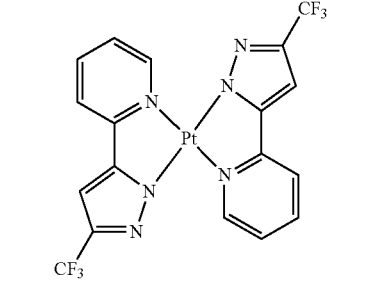

D45 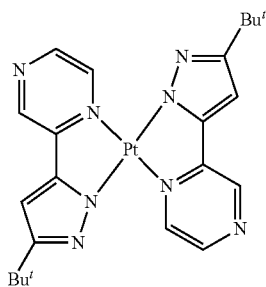
D46 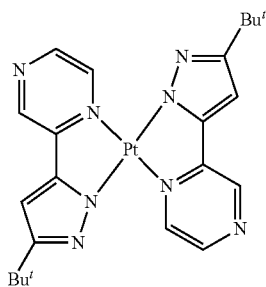
D47 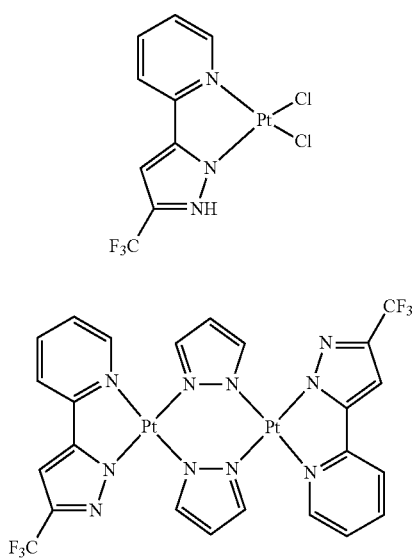
D48 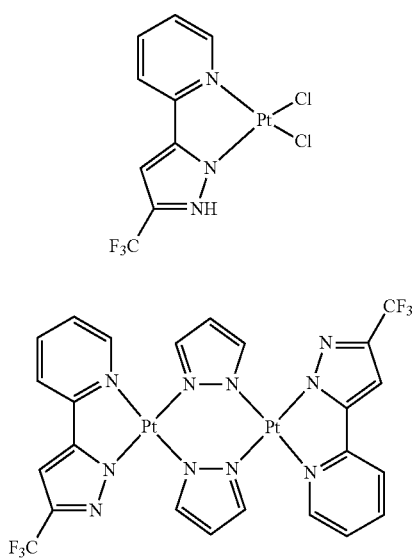
D49 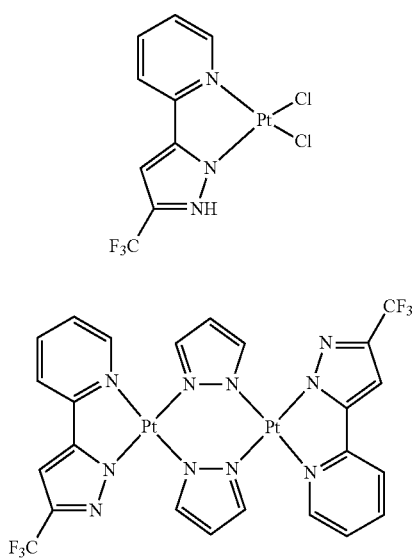
D50 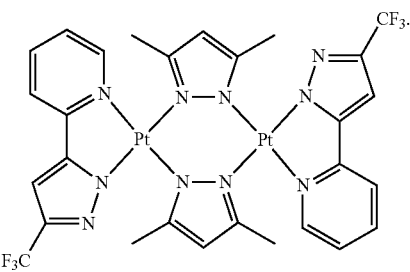
Non-limiting examples of the dopant that may be used in the emission layer may be Os-complexes represented by the following formulae.
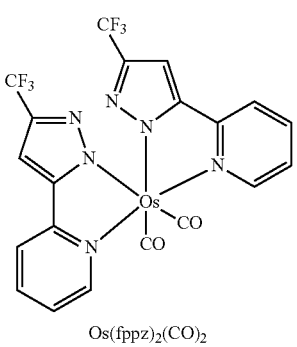
Os(fppz)$_2$(CO)$_2$
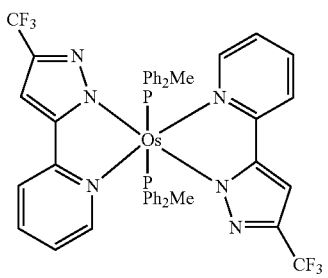
Os(fppz)$_2$(PPh$_2$Me)$_2$
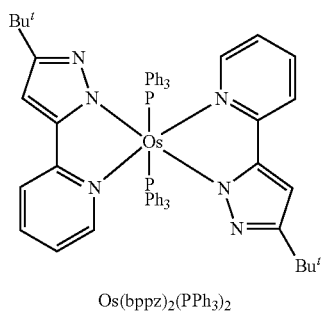
Os(bppz)$_2$(PPh$_3$)$_2$

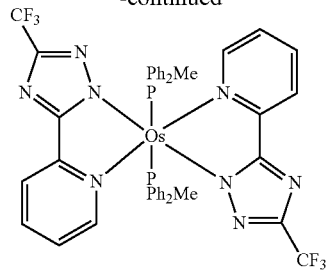

Os(fptz)₂(PPh₂Me)₂

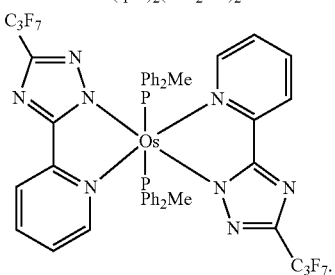

Os(hptz)₂(PPhMe₂)₂

When the emission layer includes both a host and a dopant, the content of the dopant may be from about 0.01 parts by weight to about 15 parts by weight based on 100 parts by weight of the host. However, the content of the dopant is not limited to this range.

The thickness of the emission layer may be from about 100 Å to about 1000 Å, and in some embodiments, is from about 200 Å to about 600 Å. In one embodiment, when the thickness of the emission layer is within these ranges, the emission layer has a good light emitting ability without a substantial increase in driving voltage.

Then, an electron transport layer (ETL) may be formed by any of a variety of methods, for example, vacuum deposition, spin coating, or casting. When the electron transport layer is formed by using vacuum deposition or spin coating, the deposition and coating conditions may be similar to those for the formation of the hole injection layer, though the deposition and coating conditions may vary according to a material that is used to form the electron transport layer. As the electron transporting material, any suitable electron transporting material that can stably transport electrons injected from an electron injecting electrode (cathode) may be used as a material for the electron transport layer. Non-limiting examples of the suitable electron transport materials include quinoline derivatives such as tris(8-quinolinorate)aluminum (Alq3), TAZ, BAlq, beryllium bis(benzoquinolin-10-olate (Bebq2), 9,10-di(naphthalene-2-yl)anthracene (ADN), Compound 201, and Compound 202.

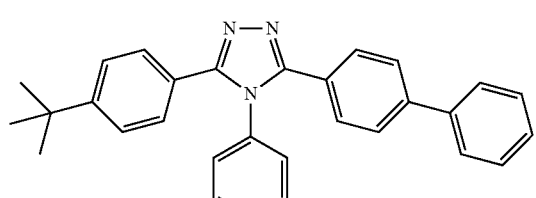

TAZ

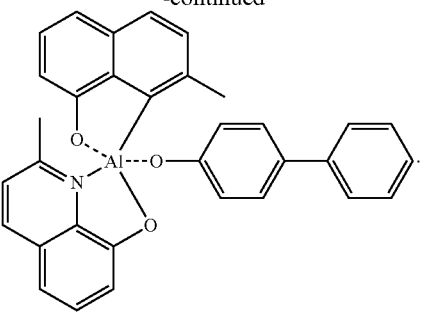

BAlq

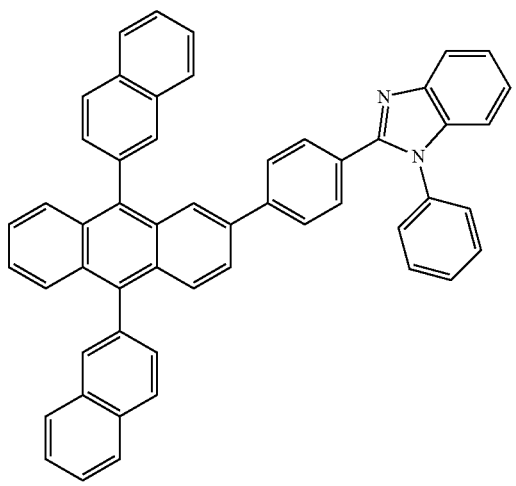

Compound 201

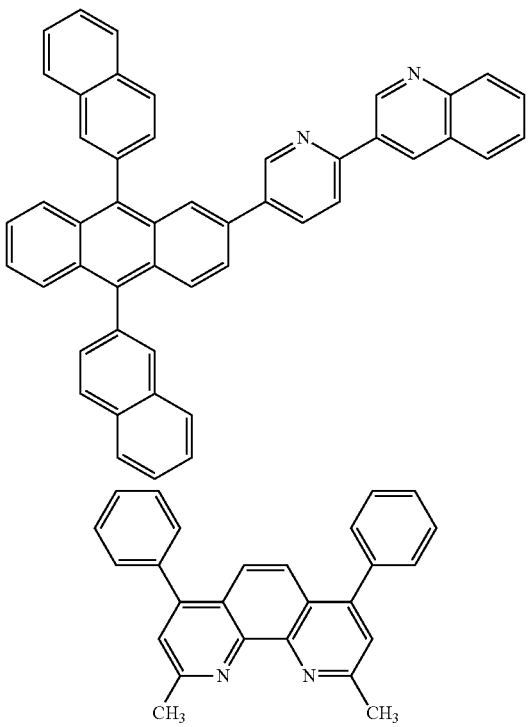

Compound 202

BCP

A thickness of the electron transport layer may be from about 100 Å to about 1,000 Å, and in some embodiments, is from about 150 Å to about 500 Å. In one embodiment, when the thickness of the electron transport layer is within these ranges, the electron transport layer has a satisfactory electron transporting ability without a substantial increase in driving voltage.

In some embodiments, the electron transport layer further includes a metal-containing material, in addition to any suitable electron-transporting organic compound.

The metal-containing material may include a lithium (Li) complex. Non-limiting examples of the Li complex are lithium quinolate (LiQ) and Compound 203 below:

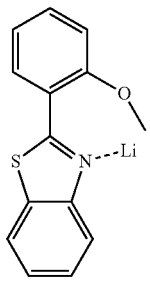

Compound 203

Then, an electron injection layer (EIL), which facilitates injection of electrons from the negative electrode, may be deposited on the electron transport layer. Any suitable electron-injecting material may be used to form the electron injection layer.

Non-limiting examples of the material for forming the electron injection layer are LiF, NaCl, CsF, $Li_2O$, and BaO. The deposition and coating conditions for forming the electron injection layer may be similar to those for the formation of the hole injection layer, though the deposition and coating conditions may vary according to the material that is used to form the electron injection layer.

A thickness of the electron injection layer may be from about 1 Å to about 100 Å, and in some embodiments, is from about 3 Å to about 90 Å. In one embodiment, when the thickness of the electron injection layer is within these ranges, the electron injection layer has a satisfactory electron injection ability without a substantial increase in driving voltage.

The second electrode is provided on the organic layer. The second electrode may be a cathode that is an electron injection electrode. A material for forming the second electrode may be a metal, an alloy, an electro-conductive compound, which have a low work function, or a mixture thereof. In this regard, lithium (Li), magnesium (Mg), aluminum (Al), aluminum-lithium (Al—Li), calcium (Ca), magnesium-indium (Mg—In), magnesium-silver (Mg—Ag), or the like may be formed into a thin film to obtain a transmission electrode. In some embodiments, various changes are possible for manufacturing a top-emission light-emitting device, such as forming the transmission electrode of indium tin oxide (ITO) or indium zinc oxide (IZO).

Although the organic light-emitting device of the drawing is described above, the present invention is not limited thereto.

When a phosphorescent dopant is also used in the emission layer, a hole blocking layer may be formed between the electron transport layer and the emission layer or between the E-functional layer and the emission layer by using vacuum deposition, spin coating, casting, LB deposition, or the like, to prevent diffusion of triplet excitons or holes into the electron transport layer. When the hole blocking layer is formed by using vacuum deposition or spin coating, the conditions for deposition and coating may be similar to those for the formation of the hole injection layer, although the conditions for deposition and coating may vary according to the material that is used to form the hole blocking layer. Suitable hole blocking layer materials such as oxadiazole derivatives, triazole derivatives, or phenanthroline derivatives may be used. For example, materials such as BCP below may be used as the hole blocking layer material.

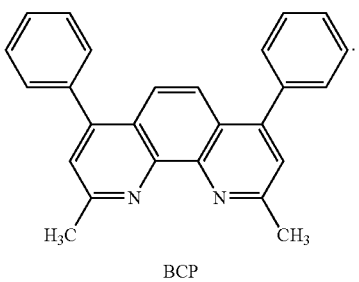 [SMILES: Cc1cc(-c2ccccc2)c2ccc3c(-c4ccccc4)cc(C)nc3c2n1 ; "BCP"]

BCP

A thickness of the hole blocking layer may be from about 20 Å to about 1000 Å, and in some embodiments, is from about 30 Å to about 300 Å. In one embodiment, when the thickness of the hole blocking layer is within these ranges, the hole blocking layer has improved a hole blocking ability without a substantial increase in driving voltage.

The organic light emitting device according to the present invention may be included in various flat display devices, for example, a passive matrix organic light emitting display device, or an active matrix organic light emitting display device. More particularly, when the organic light emitting device is included in the active matrix organic light emitting display device, the first electrode disposed on the substrate may be electrically connected to the source electrode or to a drain electrode of the thin film transistor as a pixel electrode. Also, the organic light emitting device may be included in a flat display device capable of displaying images on both sides.

Also, the organic light emitting device according to an embodiment of the present invention is formed through a deposition method by using the compounds according to an embodiment of the present invention, or is formed through a wet method of coating the compounds according to an embodiment of the present invention.

Hereinafter, the organic light emitting device according to an embodiment of the present inventive concept will be described in greater detail with reference to the following Synthesis Examples and Examples. However, these examples are for illustrative purposes only and are not intended to limit the scope of the present invention.

EXAMPLE

Synthesis Example 1

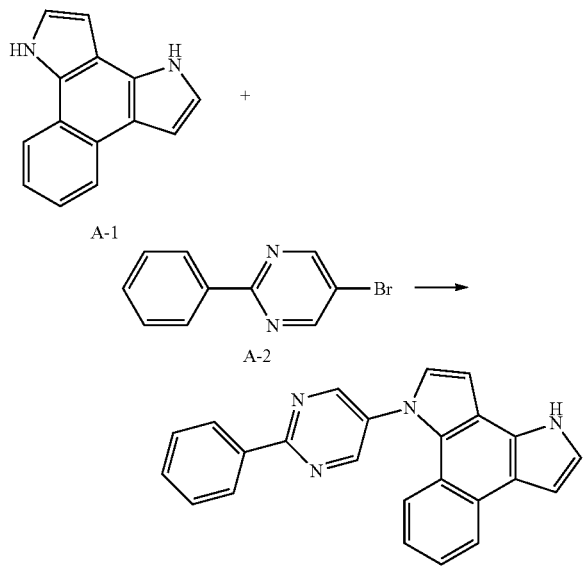

Synthesis of Intermediate A-3

10 g (1 eq, 0.048 mol) of A-1 and 14.06 g (1.1 eq, 0.049 mol) of A-2 were added to a flask and dissolved in 700 ml of toluene. 0.08 g (0.03 eq, 0.000144 mmol) of Pd$_2$(dba)$_3$, 4.27 g (1.2 eq, 0.057 mol) of Na(t-bu)O, and 0.07 g (0.06 eq, 0.00288 mmol) of P(t-Bu)$_3$ were added to the flask and dissolved in 150 ml of additional toluene to prepare a mixture, and the mixture was thermally agitated for 12 hours to prepare a reaction solution. The reaction solution was filtered through Celite and then subjected to a column chromatography to obtain 14.7 g (yield rate=84.2%) of Compound 1.

Elemental Analysis for C24H16N4: calcd C, 79.98; H, 4.47; N, 15.55.

HRMS for C24H16N4 [M]+: calcd 360.14. found 360.

Synthesis of Compound 1

8 g (1 eq, 0.022 mol) of A-3 and 7.84 g (1.1 eq, 0.0242 mol) of A-4 were added to a flask and dissolved in 500 ml of Toluene. 0.08 g (0.03 eq, 0.000144 mmol) of Pd$_2$(dba)$_3$, 4.27 g (1.2 eq, 0.057 mol) of Na(t-bu)O, and 0.07 g (0.06 eq, 0.00288 mmol) of P(t-Bu)$_3$ were added to the flask and dissolved in 150 ml of additional toluene to prepare a mixture, and the mixture was thermally agitated for 12 hours to prepare a reaction solution. The reaction solution was filtered through Celite and then subjected to a column chromatography to obtain 11.1 g (yield rate=84%) of Compound 1.

Elemental Analysis for C42H27N5: calcd C, 83.84; H, 4.52; N, 11.64.

HRMS for C42H27N5 [M]+: calcd 601.23. found 601.

Synthesis Example 2

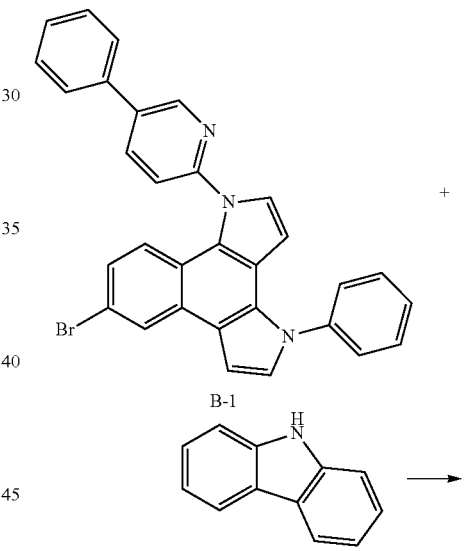

2

Synthesis of Compound 2

10 g (1 eq, 0.019 mol) of B-1 and 3.58 g (1.1 eq, 0.0214 mol) of B-2 were added to a flask and dissolved in 450 ml of Toluene. 0.52 g (0.03 eq, 0.00057 mmol) of Pd$_2$(dba)$_3$, 3.79 g (1.2 eq, 0.022 mol) of Na(t-bu)O, and 1.57 g (0.06 eq, 0.0114 mmol) of P(t-Bu)$_3$ were added to the flask and dissolved in 150 ml of additional toluene to prepare a mixture, and the mixture was thermally agitated for 12 hours to prepare a reaction solution. The reaction solution was filtered through Celite and then subjected to a column chromatography to obtain 9.0 g (yield rate=79%) of Compound 2.

Elemental Analysis for C43H28N4: calcd C, 85.98; H, 4.70; N, 9.33.

HRMS for C43H28N4 [M]+: calcd 600.23. found 600.

Synthesis Example 3

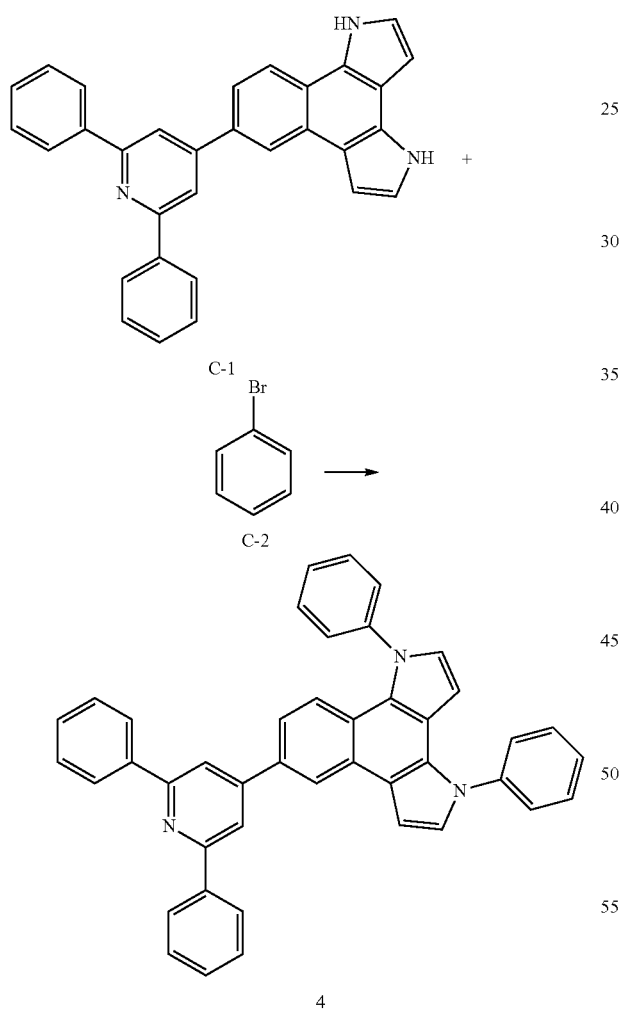

10 g (1 eq, 0.022 mol) of C-1 and 7.8 g (2.2 eq, 0.05 mol) of C-2 were added to a flask and dissolved in 300 ml of Toluene. 0.64 g (0.03 eq, 0.00066 mmol) of Pd$_2$(dba)$_3$, 6.59 g (2.2 eq, 0.05 mol) of Na(t-bu)O, and 1.22 g (0.06 eq, 0.0132 mmol) of P(t-Bu)$_3$ were added to the flask and dissolved in 150 ml of additional toluene to prepare a mixture, and the mixture was thermally agitated for 12 hours to prepare a reaction solution. The reaction solution was filtered through Celite and then subjected to a column chromatography to obtain 10.9 g (yield rate=85%) of Compound 4.

Elemental Analysis for C43H29N3: calcd C, 87.88; H, 4.97; N, 7.15.

HRMS for C43H29N3 [M]+: calcd 587.24. found 587.

Synthesis Example 4

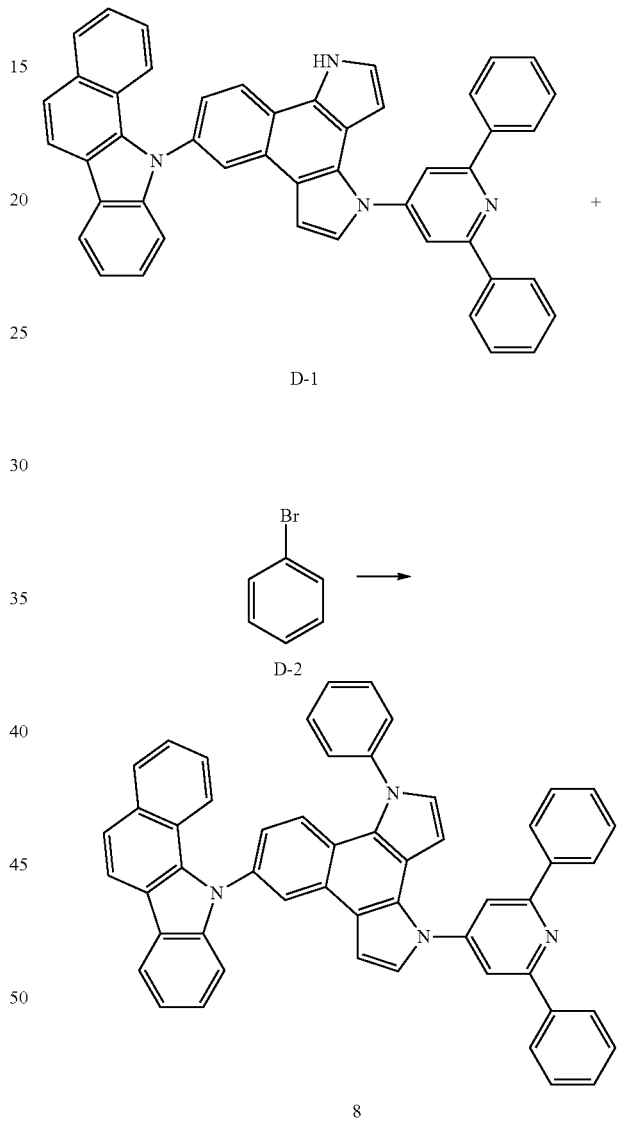

10 g (1 eq, 0.015 mol) of D-1 and 0.239 g (1.1 eq, 0.0153 mol) of D-2 were added to a flask and dissolved in 250 ml of Toluene. 0.32 g (0.03 eq, 0.0003 mmol) of Pd$_2$(dba)$_3$, 3.28 g (1.1 eq, 0.025 mol) of Na(t-bu)O, and 0.61 g (0.06 eq, 0.0006 mmol) of P(t-Bu)$_3$ were added to the flask and dissolved in 100 ml of additional toluene to prepare a mixture, and the mixture was thermally agitated for 12 hours to prepare a reaction solution. The reaction solution was filtered through Celite and then subjected to a column chromatography to obtain 8.8 g (yield rate=81.4%) of Compound 8.

Elemental Analysis for C53H34N4: calcd: C, 87.58; H, 4.71; N, 7.71.

HRMS for C53H34N4 [M]+: calcd 726.28. found 726.

Synthesis Example 5

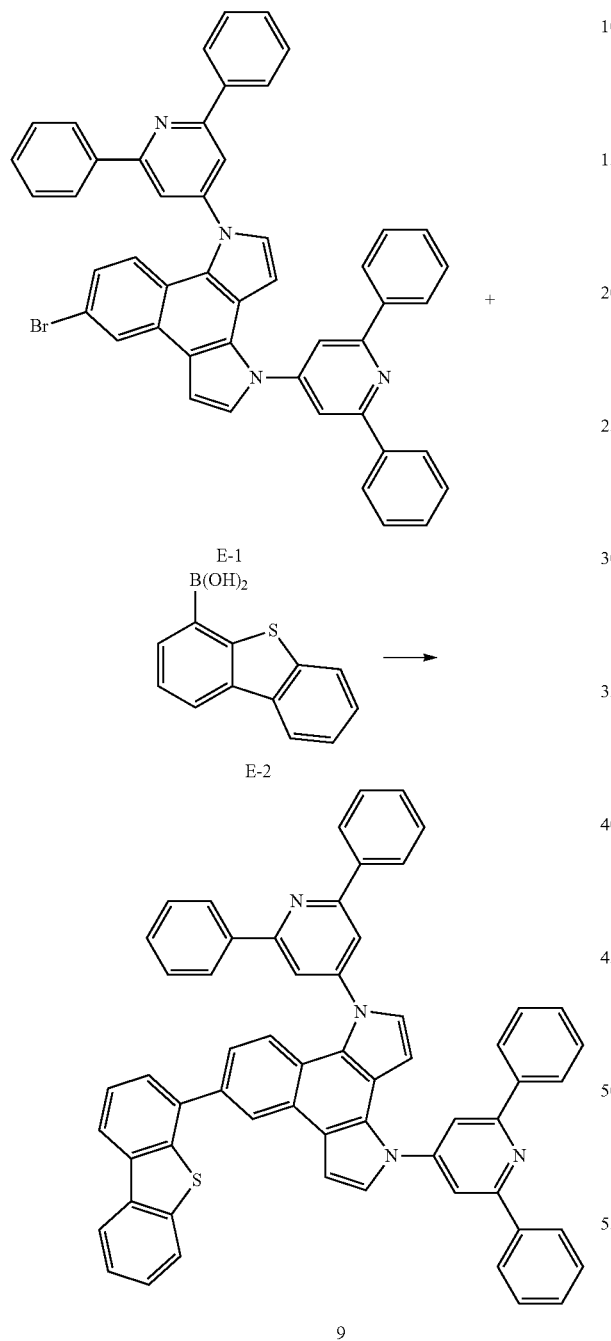

10 g (1 eq, 0.013 mol) of E-1 and 3.37 g (1.1 eq, 0.0148 mol) of E-2 were added to a flask and dissolved in 250 ml of Toluene. 0.3 g (0.02 eq, 0.00026 mmol) of Pd(PPh3)4, and 60 ml of 2 M K2CO3 solution were added to the flask to prepare a mixture, and the mixture was thermally agitated for 12 hours to prepare a reaction solution. The reaction solution was filtered through Celite and then subjected to a column chromatography to obtain 9.09 g (yield rate=82.7%) of Compound 9.

Elemental Analysis for C60H38N4S: calcd: C, 85.08; H, 4.52; N, 6.61; S, 3.79.

HRMS for C60H38N4S [M]+: calcd 846.28. found 846.

Synthesis Example 6

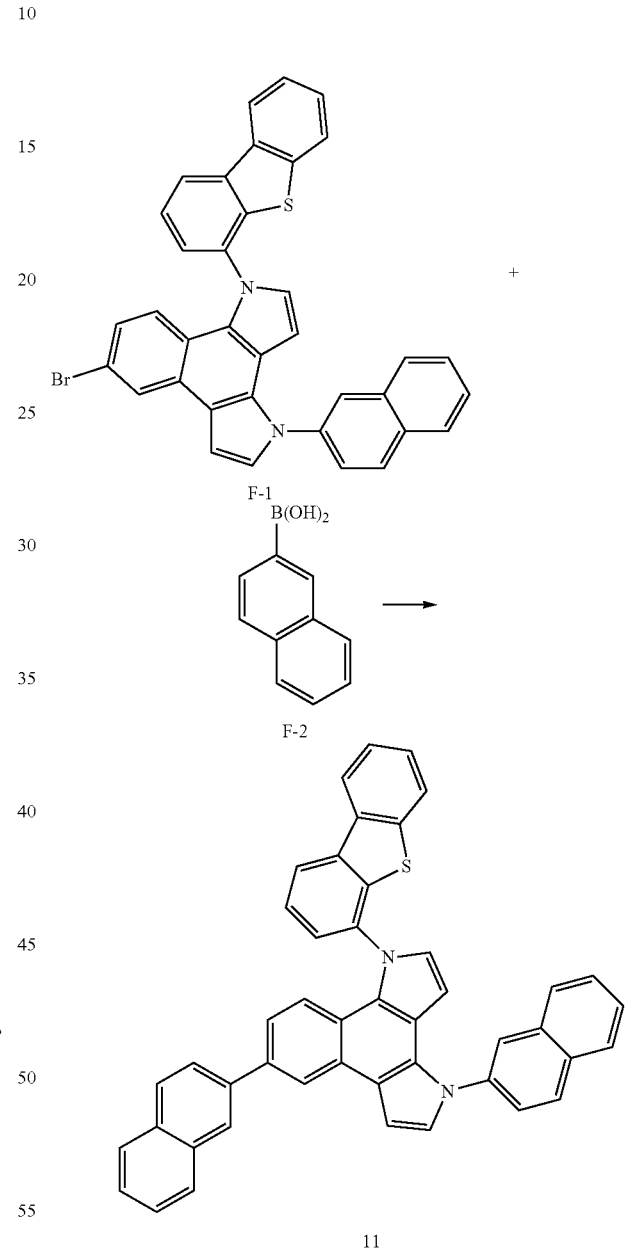

10 g (1 eq, 0.0163 mol) of F-1 and 3.19 g (1.1 eq, 0.018 mol) of F-2 were added to a flask and dissolved in 400 ml of Toluene. 0.37 g (0.02 eq, 0.00032 mmol) of Pd(PPh3)4, and 70 ml of 2 M K2CO3 solution were added to the flask to prepare a mixture, and the mixture was thermally agitated for 12 hours to prepare a reaction solution. The reaction solution was filtered through Celite and then subjected to a column chromatography to obtain 9.2 g (yield rate=88.4%) of Compound 11.

Elemental Analysis for C60H38N4S: calcd: C, 85.08; H, 4.52; N, 6.61; S, 3.79.
HRMS for C60H38N4S [M]+: calcd 846.28. found 846.

Synthesis Example 7

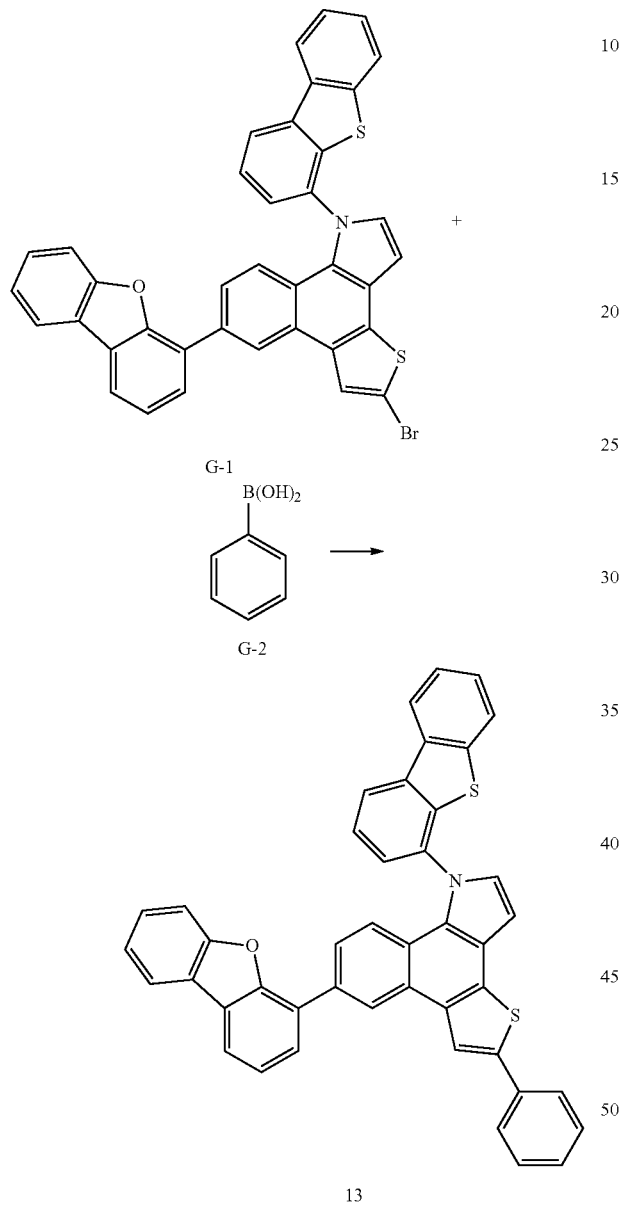

Synthesis Example 8

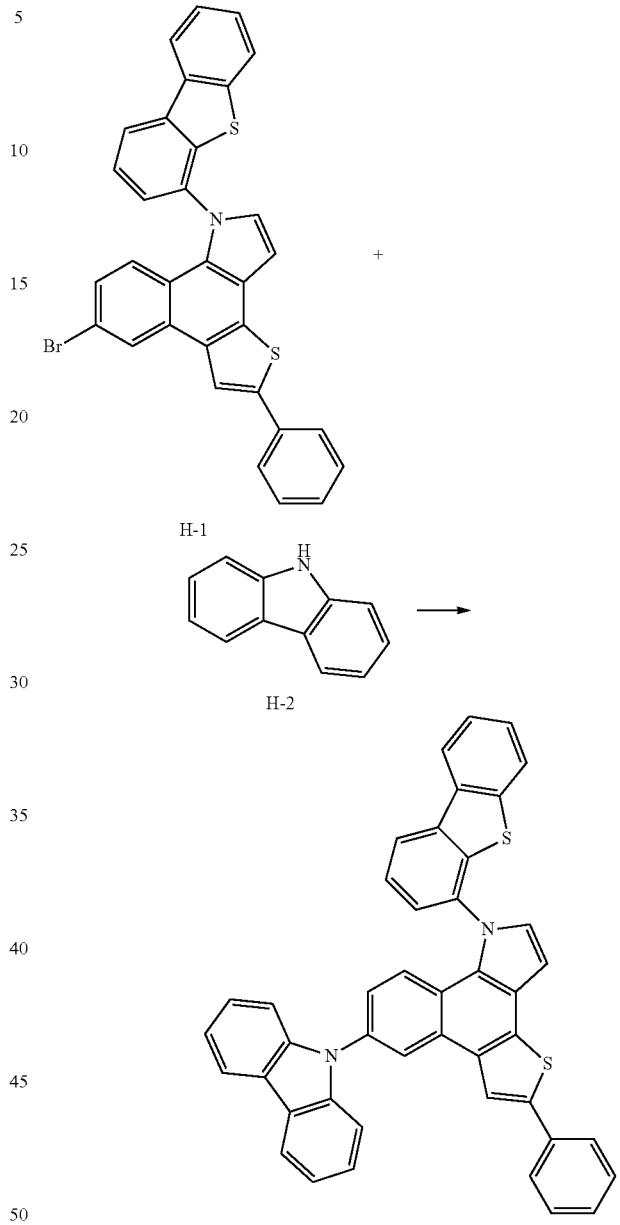

10 g (1 eq, 0.0124 mol) of G-1 and 2.06 g (1.1 eq, 0.0169 mol) of G-2 were added to a flask and dissolved in 600 ml of Toluene. 0.286 g (0.02 eq, 0.000248 mmol) of Pd(PPh$_3$)$_4$, and 70 ml of 2 M K$_2$CO$_3$ solution were added to the flask to prepare a mixture, and the mixture was thermally agitated for 12 hours to prepare a reaction solution. The reaction solution was filtered through Celite and then subjected to a column chromatography to obtain 6.6 g (yield rate=82.3%) of Compound 13.

Elemental Analysis for C44H25NOS2: calcd: C, 81.58; H, 3.89; N, 2.16; O, 2.47; S, 9.90.
HRMS for C44H25NOS2 [M]+: calcd 647.14. found 647.

10 g (1 eq, 0.017 mol) of H-1 and 3.28 g (1.1 eq, 0.0196 mol) of H-2 were added to a flask and dissolved in 300 ml of Toluene. 0.42 g (0.03 eq, 0.0005 mmol) of Pd$_2$(dba)$_3$, 2.74 g (1.1 eq, 0.0196 mol) of Na(t-bu)O, and 0.84 g (0.06 eq, 0.001 mmol) of P(t-Bu)$_3$ were added to the flask and dissolved in 100 ml of additional toluene to prepare a mixture, and the mixture was thermally agitated for 12 hours to prepare a reaction solution. The reaction solution was filtered through Celite and then subjected to a column chromatography to obtain 8.6 g (yield rate=79.1%) of Compound 14.

Elemental Analysis for C44H26N2S2: calcd: C, 81.70; H, 4.05; N, 4.33; S, 9.91.
HRMS for C44H26N2S2 [M]+: calcd 646.15. found 646.

Synthesis Example 9

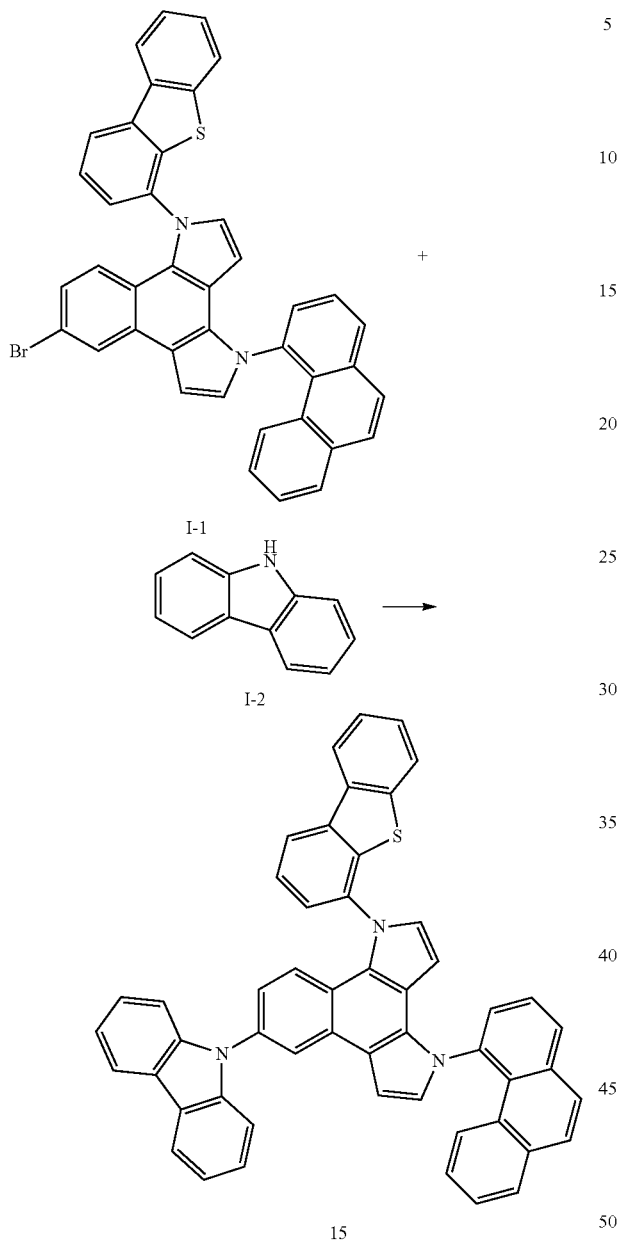

10 g (1 eq, 0.017 mol) of 1-1 and 3.28 g (1.1 eq, 0.0196 mol) of 1-2 were added to a flask and dissolved in 300 ml of Toluene. 0.42 g (0.03 eq, 0.0005 mmol) of $Pd_2(dba)_3$, 2.74 g (1.1 eq, 0.0196 mol) of Na(t-bu)O, and 0.84 g (0.06 eq, 0.001 mmol) of $P(t\text{-}Bu)_3$ were added to the flask and dissolved in 100 ml of additional toluene to prepare a mixture, and the mixture was thermally agitated for 12 hours to prepare a reaction solution. The reaction solution was filtered through Celite and then subjected to a column chromatography to obtain 9.6 g (yield rate=77.9%) of Compound 15.

Elemental Analysis for $C_{52}H_{31}N_3S$: calcd: C, 85.57; H, 4.28; N, 5.76; S, 4.39.

HRMS for $C_{52}H_{31}N_3S$ [M]+: calcd 729.22. found 729.

Synthesis Example 10

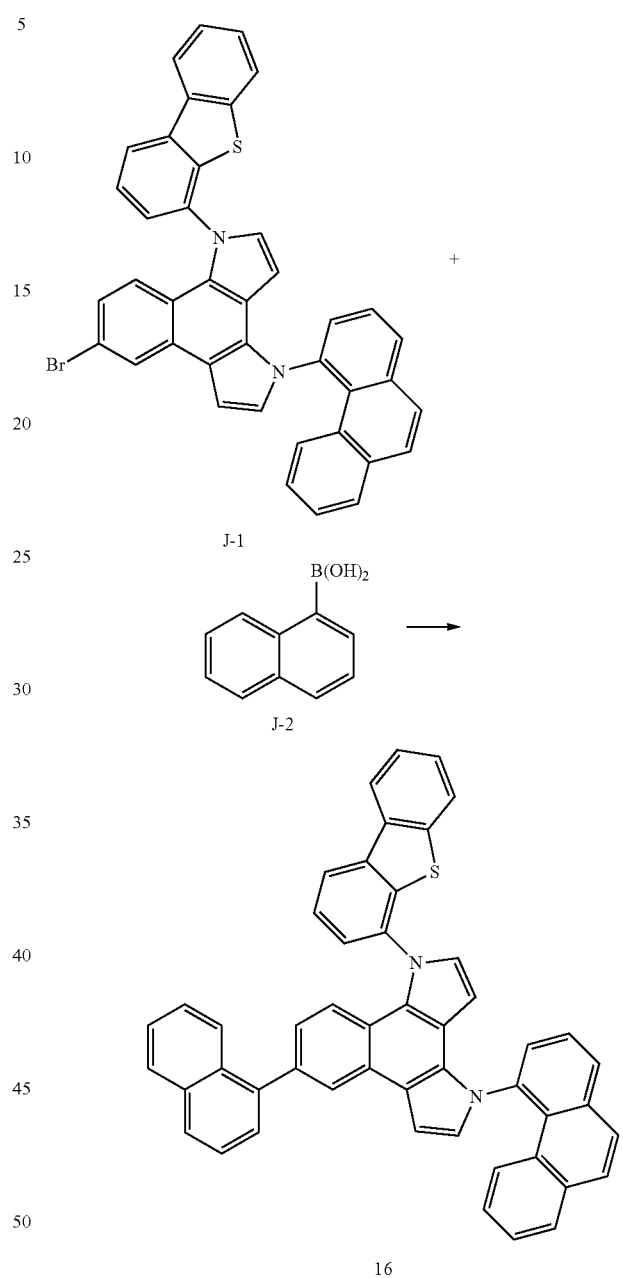

10 g (1 eq, 0.0155 mol) of J-1 and 2.9 g (1.1 eq, 0.0171 mol) of J-2 were added to a flask and dissolved in 550 ml of Toluene. 0.35 g (0.02 eq, 0.00031 mmol) of $Pd(PPh_3)_4$, and 50 ml of 2 M $K_2CO_3$ solution were added to the flask to prepare a mixture, and the mixture was thermally agitated for 12 hours to prepare a reaction solution. The reaction solution was filtered through Celite and then subjected to a column chromatography to obtain 8.8 g (yield rate=83%) of Compound 16.

Elemental Analysis for $C_{50}H_{30}N_2S$: calcd: C, 86.93; H, 4.38; N, 4.05; S, 4.64.

HRMS for $C_{50}H_{30}N_2S$ [M]+: calcd 690.21. found 690.

Synthesis Example 11

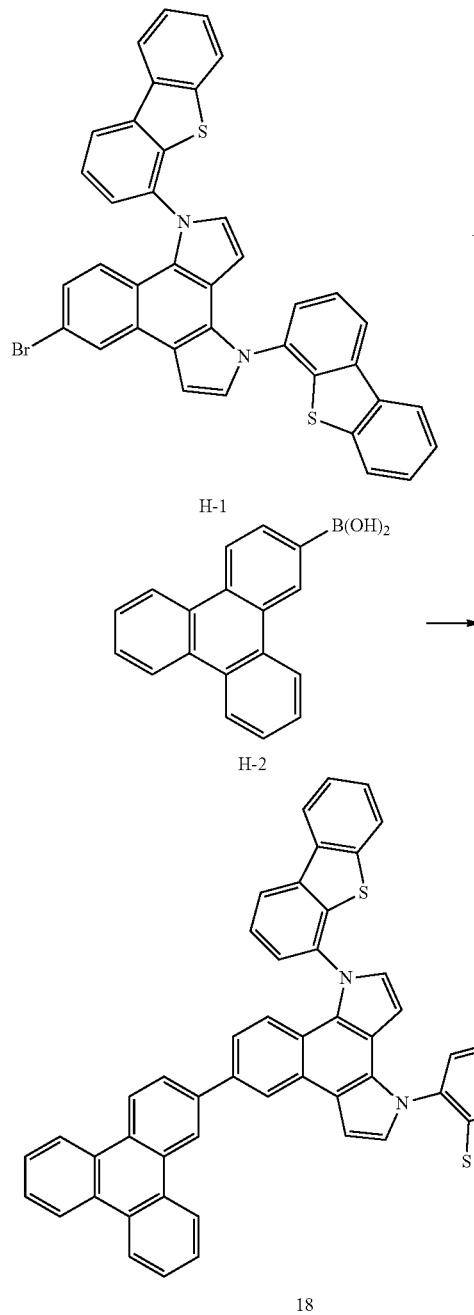

10 g (1 eq, 0.0154 mol) of H-1 and 4.6 g (1.1 eq, 0.0169 mol) of H-2 were added to a flask and dissolved in 450 ml of Toluene. 0.35 g (0.02 eq, 0.00031 mmol) of Pd(PPh$_3$)$_4$, and 45 ml of 2 M K$_2$CO$_3$ solution were added to the flask to prepare a mixture, and the mixture was thermally agitated for 12 hours to prepare a reaction solution. The reaction solution was filtered through Celite and then subjected to a column chromatography to obtain 10.59 g (yield rate=86.4%) of Compound 18.

Elemental Analysis for C$_{56}$H$_{32}$N$_2$S$_2$: calcd: C, 84.39; H, 4.05; N, 3.51; S, 8.05.

HRMS for C$_{56}$H$_{32}$N$_2$S$_2$ [M]+: calcd 796.2. found 796.

Example 1

As an anode, a Corning 15 Ω/cm$^2$ (500 Å) ITO glass substrate was cut into a size of 50 mm×50 mm×0.5 mm and the ITO glass substrate was ultrasonically washed using isopropyl alcohol and distilled water for 10 minutes, followed by irradiation of UV and exposure to ozone for cleaning for about 10 minutes. The ITO glass substrate was then loaded onto a vacuum deposition device. 2-TNATA, a suitable material as a hole injecting material was vacuum deposited on the substrate to form an hole injection layer in a thickness of 600 Å, and 4,4'-bis[N-(1-naphthyl)-N-phenyl amino]biphenyl (NPB), a suitable material as a hole transport compound was vacuum deposited thereto to form a hole transport layer in a thickness of 300 Å.

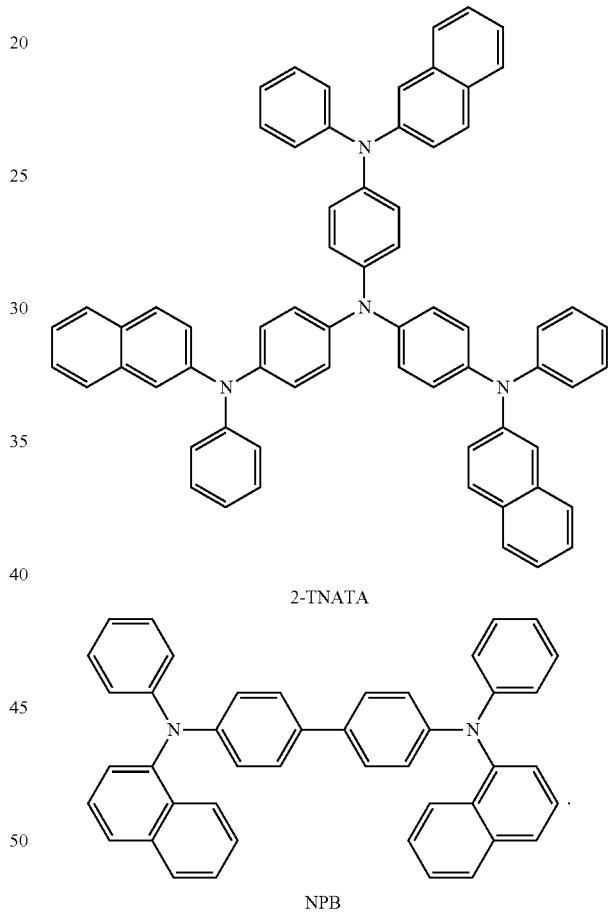

A phosphorescent dopant, Ir(ppy)$_3$ and Compound 1 were concurrently or simultaneously deposited on the hole transport layer in a weight ratio of 13:87 to form an emission layer having a thickness of 300 Å. Thereafter, Alq$_3$ was deposited in a thickness of 300 Å as an electron transport layer on the emission layer, and then Al was vacuum deposited in a thickness of 1200 Å (a cathode electrode) to manufacture an OLED.

The OLED showed a driving voltage of 4.8 V at a current density of 6.1 mA/ad, emission efficiency of 16.5 cd/A at a luminescence brightness of 1000 cd/m$^2$, and showed a green light emission.

Example 2

An OLED was manufactured in the same manner as in Example 1, except for using Compound 2 instead of Compound 1 when forming an emission layer.

The OLED showed a driving voltage of 5.2 V at a current density of 6.7 mA/cm², emission efficiency of 17.4 cd/A at a luminescence brightness of 1000 cd/m², and showed a green light emission.

Example 3

An OLED was manufactured in the same manner as in Example 1, except for using Compound 4 instead of Compound 1 when forming an emission layer.

The OLED showed a driving voltage of 5.5 V at a current density of 5.8 mA/ad, emission efficiency of 14.7 cd/A at a luminescence brightness of 1000 cd/d, and showed a green light emission.

Example 4

An OLED was manufactured in the same manner as in Example 1, except for using Compound 8 instead of Compound 1 when forming an emission layer.

The OLED showed a driving voltage of 5.7 V at a current density of 5.5 mA/ad, emission efficiency of 12.5 cd/A at a luminescence brightness of 1000 cd/m², and showed a green light emission.

Example 5

An OLED was manufactured in the same manner as in Example 1, except for using Compound 9 instead of Compound 1 when forming an emission layer.

The OLED showed a driving voltage of 6.0 V at a current density of 6.9 mA/ad, emission efficiency of 15.9 cd/A at a luminescence brightness of 1000 cd/d, and showed a green light emission.

Example 6

An OLED was manufactured in the same manner as in Example 1, except for using Compound 11 instead of Compound 1 when forming an emission layer.

The OLED showed a driving voltage of 6.1 V at a current density of 6.2 mA/ad, emission efficiency of 13.9 cd/A at a luminescence brightness of 1000 cd/m², and showed a green light emission.

Example 7

An OLED was manufactured in the same manner as in Example 1, except for using Compound 13 instead of Compound 1 when forming an emission layer.

The OLED showed a driving voltage of 5.0 V at a current density of 5.2 mA/cm², emission efficiency of 13.1 cd/A at a luminescence brightness of 1000 cd/m², and showed a green light emission.

Example 8

An OLED was manufactured in the same manner as in Example 1, except for using Compound 14 instead of Compound 1 when forming an emission layer.

The OLED showed a driving voltage of 6.9 V at a current density of 6.6 mA/cm', emission efficiency of 16.4 cd/A at a luminescence brightness of 1000 cd/d, and showed a green light emission.

Example 9

An OLED was manufactured in the same manner as in Example 1, except for using Compound 15 instead of Compound 1 when forming an emission layer.

The OLED showed a driving voltage of 5.1 V at a current density of 6.7 mA/cm², emission efficiency of 17.0 cd/A at a luminescence brightness of 1000 cd/m², and showed a green light emission.

Example 10

An OLED was manufactured in the same manner as in Example 1, except for using Compound 16 instead of Compound 1 when forming an emission layer.

The OLED showed a driving voltage of 5.9 V at a current density of 7.1 mA/cm², emission efficiency of 15.1 cd/A at a luminescence brightness of 1000 cd/m², and showed a green light emission.

Example 11

An OLED was manufactured in the same manner as in Example 1, except for using Compound 18 instead of Compound 1 when forming an emission layer.

The OLED showed a driving voltage of 6.7 V at a current density of 5.29 mA/cm², emission efficiency of 16.3 cd/A at a luminescence brightness of 1000 cd/d, and showed a green light emission.

Comparative Example

An OLED was manufactured in the same manner as in Example 1, except for using CBP as an EML host, and bis(2-methyl-8-quinolato)(p-phenylphenolato)aluminum (III) (BAlq) as an hole blocking layer.

The OLED showed a driving voltage of 7.8 V at a current density of 5.5 mA/ad, emission efficiency of 11.2 cd/A at a luminescence brightness of 1000 cd/m², and showed a green light emission.

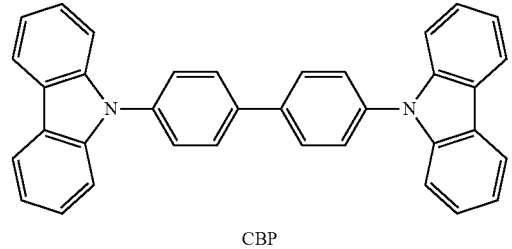 [SMILES: c1ccc2c(c1)c1ccccc1n2-c1ccc(-c2ccc(-n3c4ccccc4c4ccccc43)cc2)cc1 ; "CBP"]

CBP

As a result of using the Compounds according to the embodiments of the present invention as a host in a phosphorescent device in the emission layers of the OLEDs, all of the OLEDs showed about 15% to about 20% reduction in a driving voltage compared to when CBP was used, showed an excellent I-V-L characteristic having a substantially improved efficiency, and more particularly showed an effective improvement in lifespan. Results regarding lifespan of the OLEDs are summarized in Table 1 below.

TABLE 1

| | Emission material | T97 lifespan (hr @100 mA/cm$^2$) |
|---|---|---|
| Example 1 | Compound 1 | 970 |
| Example 2 | Compound 2 | 921 |
| Example 3 | Compound 4 | 943 |
| Example 4 | Compound 8 | 921 |
| Example 5 | Compound 9 | 991 |
| Example 6 | Compound 11 | 937 |
| Example 7 | Compound 13 | 897 |
| Example 8 | Compound 14 | 911 |
| Example 9 | Compound 15 | 956 |
| Example 10 | Compound 16 | 971 |
| Example 11 | Compound 18 | 923 |
| Comparative Example 1 | CBP | 675 |

The compound having Formula 1 above has excellent emission characteristics, and is useful for green phosphorescence. By using the compound, an OLED manufactured according to embodiments of the present invention has high efficiency, low voltage, high brightness, and long lifespan.

While the present inventive concept has been particularly shown and described with reference to example embodiments thereof, it will be understood by those of ordinary skill in the art that various changes in form and details may be made therein without departing from the spirit and scope of the present inventive concept as defined by the following claims, and equivalents thereof.

It should be understood that the example embodiments described therein should be considered in a descriptive sense only and not for purposes of limitation. Descriptions of features or embodiments within each embodiment should typically be considered as available for other similar features or embodiments in other embodiments.

What is claimed is:

1. A compound represented by Formula 1 below:

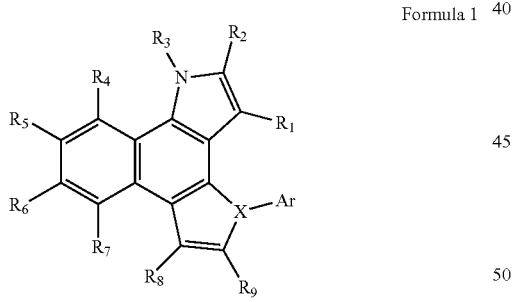

Formula 1 wherein in Formula 1 above, $R_1$ to $R_9$ are, each independently, a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_6$-$C_{60}$ aryl group, a substituted or unsubstituted $C_3$-$C_{60}$ heteroaryl group, a $C_6$-$C_{60}$ arylsilyl group, or a substituted or unsubstituted $C_6$-$C_{60}$ condensed polycyclic group;

Ar is a non-bonding electron pair, a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group; and X is N or S.

2. The compound of claim 1, wherein $R_3$ of Formula 1 is any one of structures 2a to 2e below:

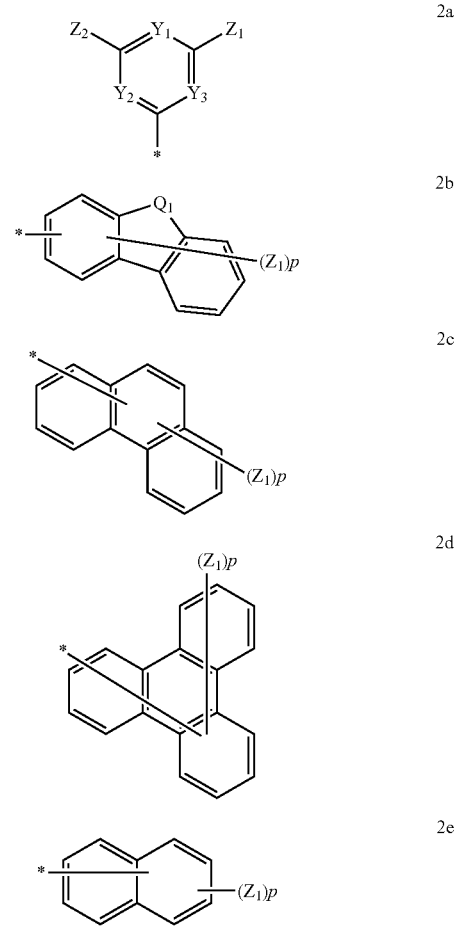

in Formulae 2a to 2e above, $Y_1$, $Y_2$, and $Y_3$ are, each independently, CH or N;

$Q_1$ is a connecting group represented by —$CR_{50}R_{51}$— or —S—;

$Z_1$, $Z_2$, $R_{50}$ and $R_{51}$ are, each independently, a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group, a $C_3$-$C_{20}$ heteroaryl group, a halogen group, a cyano group, a nitro group, a hydroxy group, or a carboxy group;

p is an integer of 1 to 11; and

* represents a binding site.

3. The compound of claim 1, wherein $R_6$ of Formula 1 is any one of the structures 3a to 3g below:

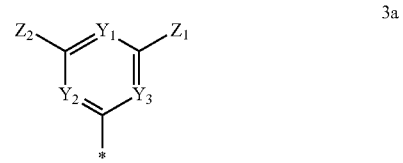

3a

-continued

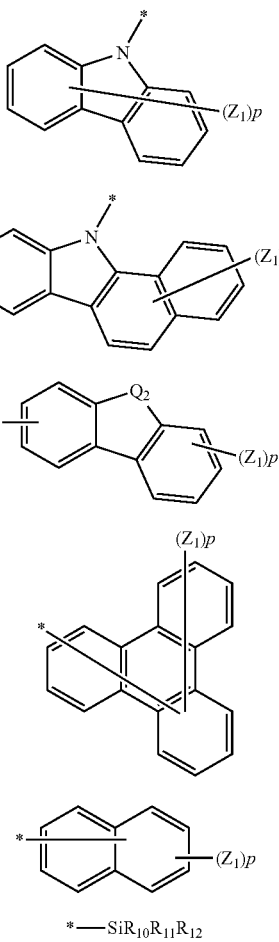

3b

3c

3d

3e

3f

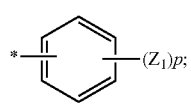

3g in Formulae 3a to 3g above, $Y_1$, $Y_2$, and $Y_3$ are, each independently, CH or N;

$Q_2$ is a connecting group represented by —O— or —S—;

$Z_1$, $Z_2$, $R_{10}$, $R_{11}$ and $R_{12}$ are, each independently, a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group, a $C_3$-$C_{20}$ heteroaryl group, a halogen group, a cyano group, a nitro group, a hydroxy group, or a carboxy group;

p is an integer of 1 to 11; and

* represents a binding site.

4. The compound of claim 1, wherein $R_9$ of Formula 1 is a hydrogen atom, a deuterium atom, or

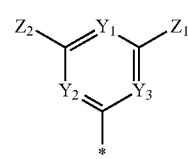

$Z_1$ is a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, amino group substituted with a $C_6$-$C_{20}$ aryl group, a $C_3$-$C_{20}$ heteroaryl group, a halogen group, a cyano group, a nitro group, a hydroxy group, or a carboxy group;

p is an integer of 1 to 5; and

* represents a binding site.

5. The compound of claim 1, wherein Ar of Formula 1 is a non-bonding electron pair, or any one of structures 4a to 4e below:

4a

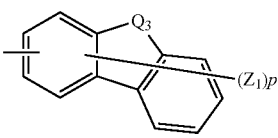

4b

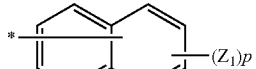

4c

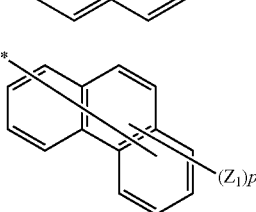

4d

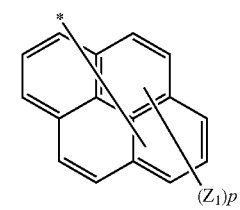

4e in Formulae 4a to 4e above, $Y_1$, $Y_2$, and $Y_3$ are, each independently, CH or N;

$Q_3$ is a connecting group represented by —$CR_{50}R_{51}$—, —$NR_{52}$—, or —S—;

$Z_1$, $Z_2$, $R_{50}$, $R_{51}$ and $R_{52}$ are, each independently, a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with $C_6$-$C_{20}$ aryl group, a $C_3$-$C_{20}$ heteroaryl group, a halogen group, a cyano group, a nitro group, a hydroxy group, or a carboxy group;

p is an integer of 1 to 9; and

* represents a binding site.

6. The compound of claim 1, wherein $R_1$, $R_2$, $R_4$, $R_5$, $R_7$ and $R_8$ of Formula 1 above are, each independently, a hydrogen atom or a deuterium atom.

7. The compound of claim 1, wherein the compound of Formula 1 above is any one of compounds 1 to 21 below:

1
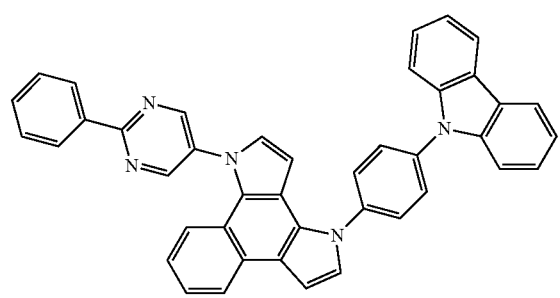
2
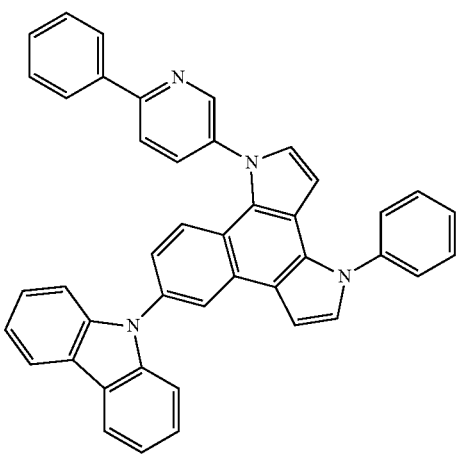
3
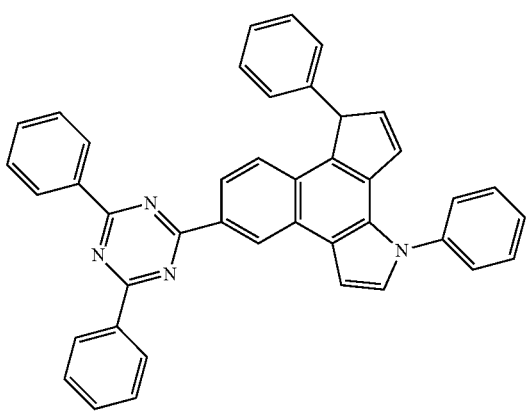
4
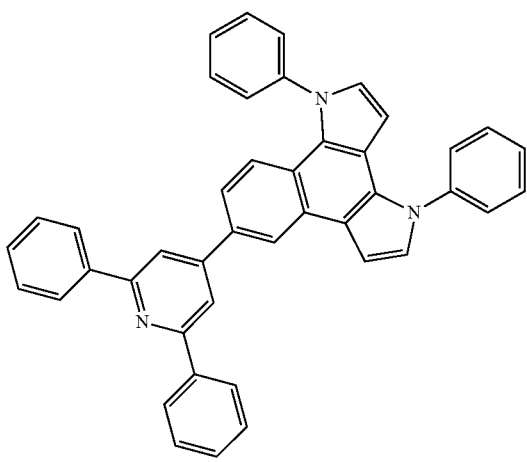
5
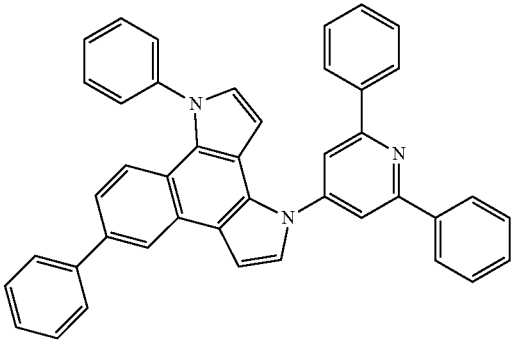
6
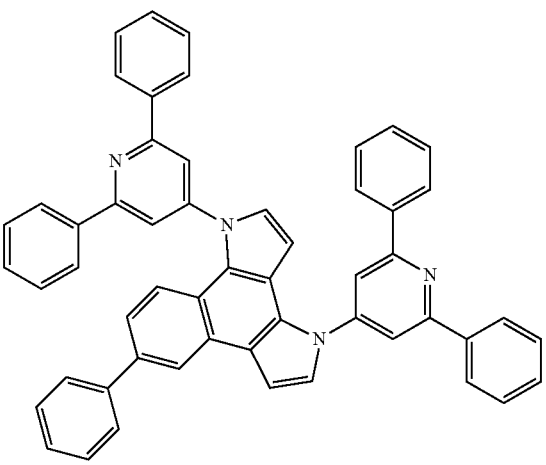
7
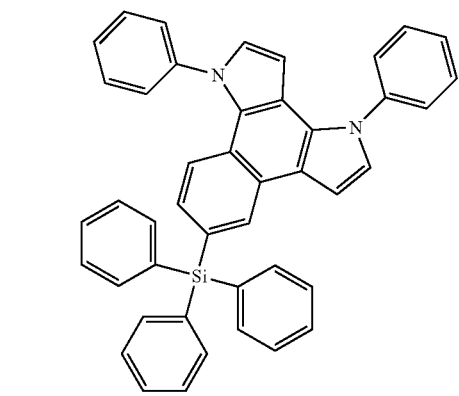
8
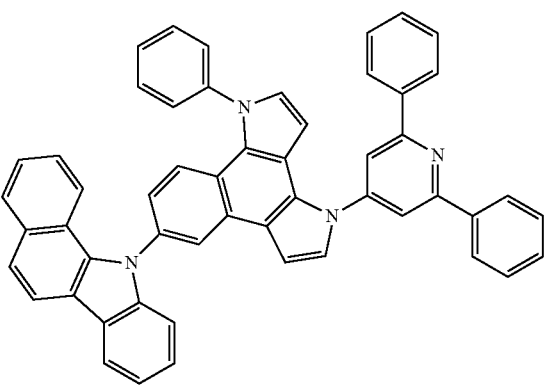

-continued
9
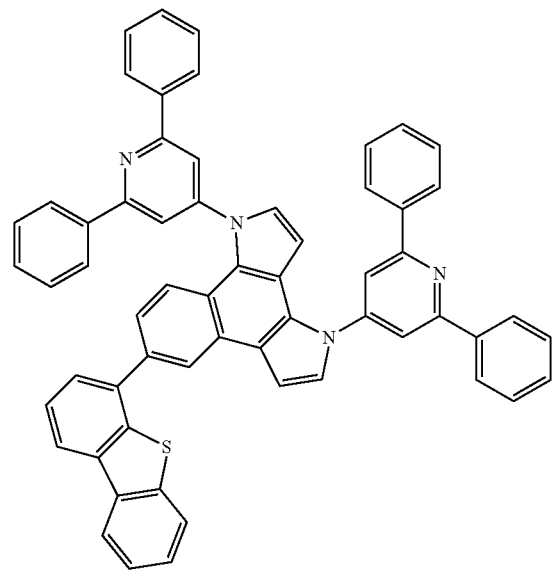
10
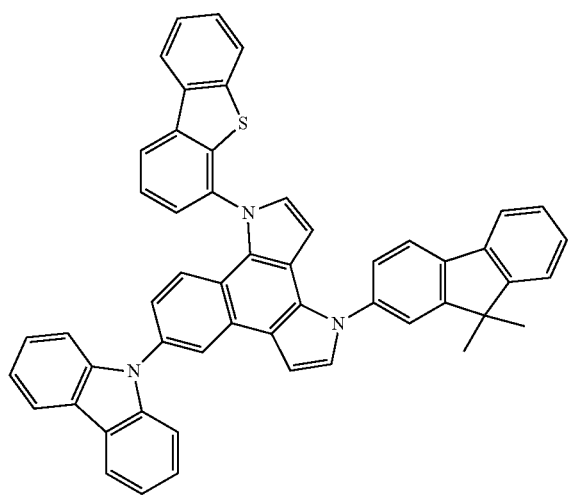
11
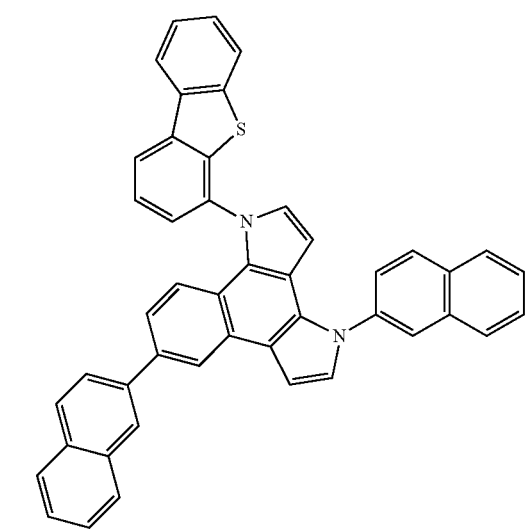
-continued
12
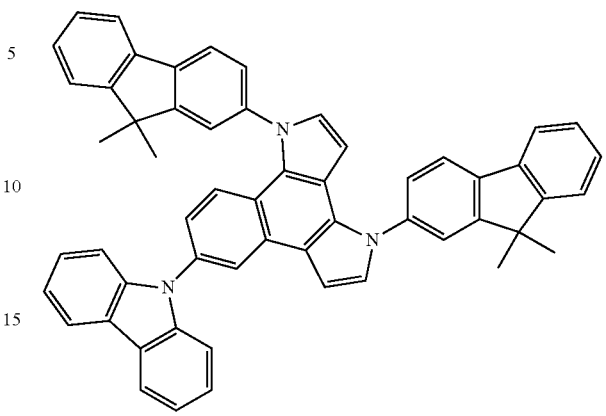
13
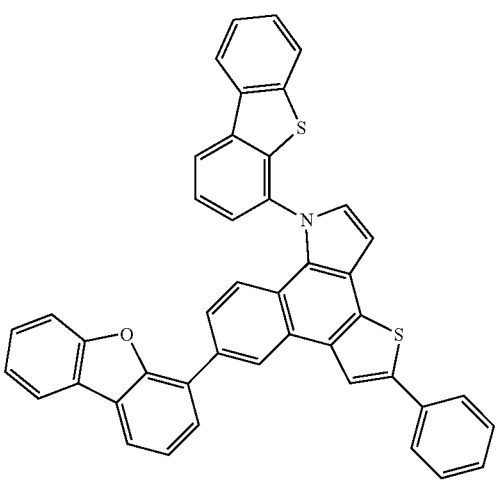
14
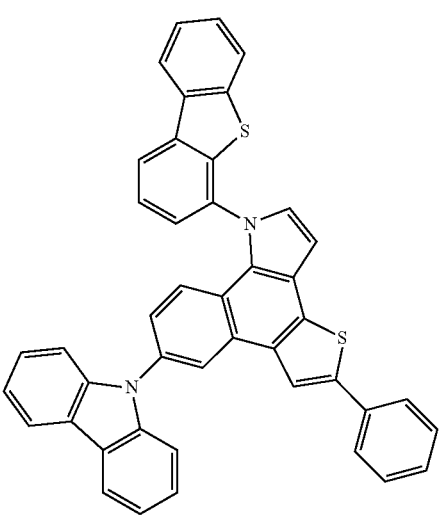

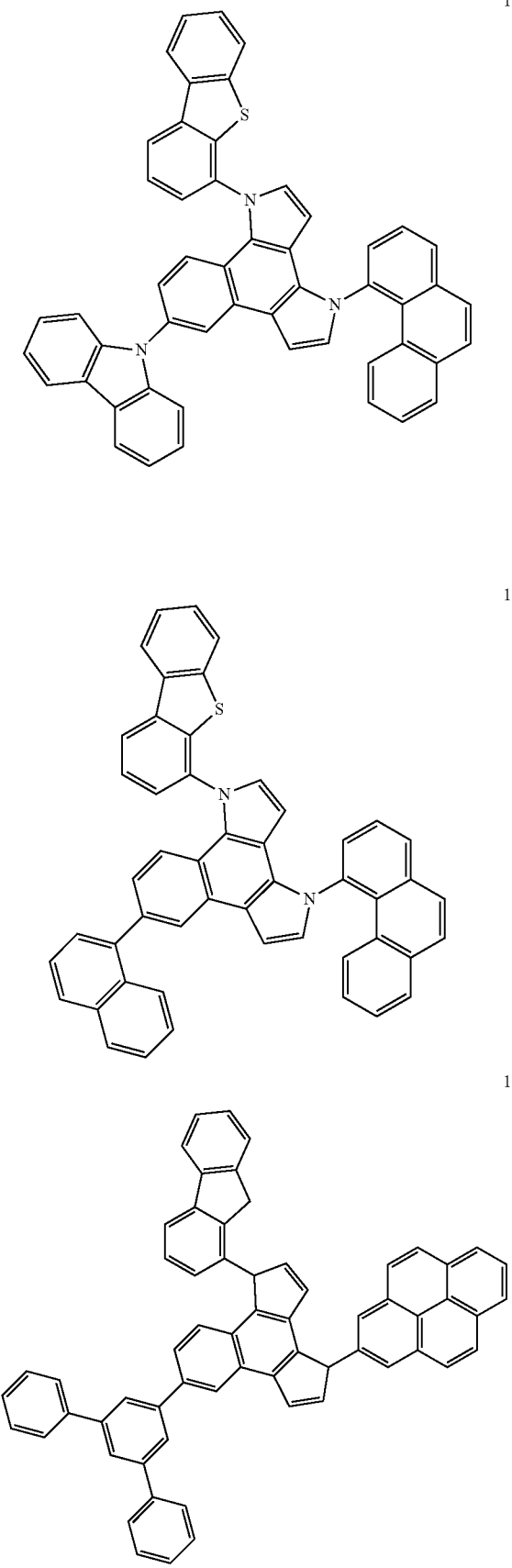
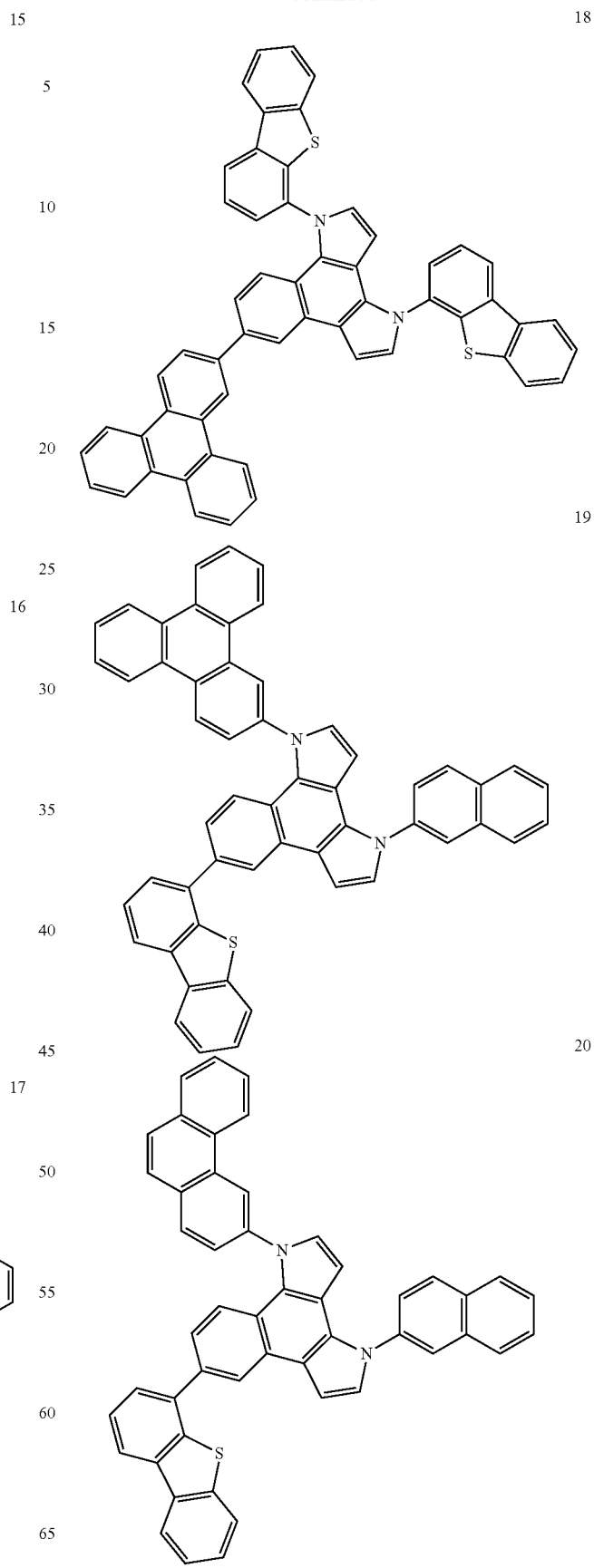

-continued

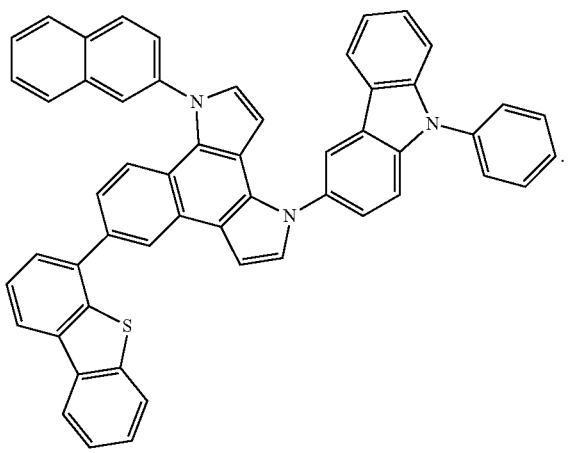

8. An organic light emitting device, comprising:
a first electrode;
a second electrode; and
an organic layer between the first electrode and the second electrode, wherein the organic layer comprises the compound of claim 1.

9. The organic light emitting device of claim 8, wherein the organic layer is an emission layer.

10. The organic light emitting device of claim 8, wherein the organic layer is an emission layer and the compound is used as a host in a phosphorescent device.

11. The organic light emitting device of claim 8, wherein the organic layer comprises an emission layer and further comprises an electron injection layer, an electron transport layer, a hole injection layer, a hole transport layer, or a functional layer having both hole injection and hole transport capabilities, wherein
the emission layer comprises the compound, and an anthracene-based compound.

12. The organic light emitting device of claim 8, wherein the organic layer comprises an emission layer and further comprises an electron injection layer, an electron transport layer, a hole injection layer, a hole transport layer, or a functional layer having both hole injection and hole transport capabilities, wherein
the emission layer comprises the compound and an arylamine-based compound.

13. The organic light emitting device of claim 8, wherein the organic layer comprises an emission layer and further comprises an electron injection layer, an electron transport layer, a hole injection layer, a hole transport layer, or a functional layer having both hole injection and hole transport capabilities, wherein
the emission layer comprises the compound and a styryl-based compound.

14. The organic light emitting device of claim 8, wherein the organic layer comprises an emission layer and further comprises an electron injection layer, an electron transport layer, a hole injection layer, a hole transport layer, or a functional layer having both hole injection and hole transport capabilities, wherein
any one layer of a red layer, a green layer, a blue layer, and a white layer of the emission layer comprises a phosphorescent compound.

15. The organic light emitting device of claim 14, wherein the hole injection layer, the hole transport layer, or the functional layer having both hole injection and hole transport capabilities comprises a charge generating material.

16. The organic light emitting device of claim 15, wherein the charge generating material is a p-dopant; and
the p-dopant is a quinone derivative, a metal oxide, or a cyano group-containing compound.

17. The organic light emitting device of claim 8, wherein the organic layer comprises an electron transport layer, and the electron transport layer comprises an organic compound transporting electron and a metal complex.

18. The organic light emitting device of claim 17, wherein the metal complex is a lithium complex.

19. The organic light emitting device of claim 8, wherein the organic layer is formed through a wet process by using the compound.

20. A flat display device comprising a thin film transistor and the organic light emitting device of claim 8, wherein a first electrode of the organic light emitting device is electrically connected to a source electrode or a drain electrode of the thin film transistor.

* * * * *